(12) United States Patent
Kostrzewski et al.

(10) Patent No.: US 11,540,851 B2
(45) Date of Patent: Jan. 3, 2023

(54) APPARATUS FOR ENDOSCOPIC PROCEDURES

(71) Applicant: Covidien LP, Mansfield, MA (US)

(72) Inventors: Stanislaw Kostrzewski, Newton, CT (US); Ernest Aranyi, Easton, CT (US); Paul Scirica, Huntington, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/495,077

(22) Filed: Oct. 6, 2021

(65) Prior Publication Data

US 2022/0022905 A1    Jan. 27, 2022

Related U.S. Application Data

(60) Continuation of application No. 16/738,076, filed on Jan. 9, 2020, now Pat. No. 11,207,089, which is a
(Continued)

(51) Int. Cl.
*A61B 17/072* (2006.01)
*A61B 17/29* (2006.01)
(Continued)

(52) U.S. Cl.
CPC ........ *A61B 17/29* (2013.01); *A61B 17/00234* (2013.01); *A61B 17/07207* (2013.01); *A61B 17/07292* (2013.01); *A61B 2017/0046* (2013.01); *A61B 2017/00314* (2013.01); *A61B 2017/00327* (2013.01); *A61B 2017/00398* (2013.01); *A61B 2017/00473* (2013.01); *A61B 2017/00685* (2013.01);
(Continued)

(58) Field of Classification Search
CPC ........ A61B 17/07207; A61B 17/07292; A61B 2017/07271; A61B 2017/07278; A61B 2017/07285
USPC ...................................... 227/175.1
See application file for complete search history.

(56) References Cited

U.S. PATENT DOCUMENTS 2,957,353 A   10/1960   Babacz
3,111,328 A   11/1963   Di Rito et al.
(Continued)

FOREIGN PATENT DOCUMENTS

AU   2008229795 A1   4/2009
CA      2451558 A1   1/2003
(Continued)

OTHER PUBLICATIONS

Japanese Office Action (with English translation) dated Nov. 29, 2016, corresponding to Japanese Application No. 2013-082014; 9 total pages.
(Continued)

*Primary Examiner* — Michelle Lopez
(74) *Attorney, Agent, or Firm* — Carter, DeLuca & Farrell LLP

(57) ABSTRACT

An electromechanical surgical system having an instrument housing for connecting with a shaft assembly, a shaft assembly, and an end effector. The end effector is an articulating end effector and the system includes a cable tensioning system for tensioning the articulation cables. The system includes a clutch mechanism for preventing slippage of a drive cable.

17 Claims, 46 Drawing Sheets

Related U.S. Application Data continuation of application No. 15/294,813, filed on Oct. 17, 2016, now Pat. No. 10,568,651, which is a division of application No. 13/891,288, filed on May 10, 2013, now Pat. No. 9,492,146, which is a continuation-in-part of application No. 13/444,228, filed on Apr. 11, 2012, now Pat. No. 8,672,206, which is a continuation-in-part of application No. 13/280,898, filed on Oct. 25, 2011, now Pat. No. 8,899,462, and a continuation-in-part of application No. 13/280,859, filed on Oct. 25, 2011, now Pat. No. 8,657,177.

(60) Provisional application No. 61/779,873, filed on Mar. 13, 2013, provisional application No. 61/672,891, filed on Jul. 18, 2012, provisional application No. 61/659,116, filed on Jun. 13, 2012.

(51) Int. Cl.
*A61B 17/00* (2006.01)
*A61B 34/00* (2016.01)
*A61B 90/00* (2016.01)
*A61B 17/32* (2006.01)

(52) U.S. Cl.
CPC .............. *A61B 2017/00734* (2013.01); *A61B 2017/07214* (2013.01); *A61B 2017/07271* (2013.01); *A61B 2017/07278* (2013.01); *A61B 2017/07285* (2013.01); *A61B 2017/2908* (2013.01); *A61B 2017/2923* (2013.01); *A61B 2017/320052* (2013.01); *A61B 2034/715* (2016.02); *A61B 2090/0814* (2016.02)

(56) References Cited

U.S. PATENT DOCUMENTS

| | | |
|---|---|---|
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,489,058 A * | 2/1996 | Plyley .................. A61B 17/064 227/176.1 |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,673,840 A * | 10/1997 | Schulze ........... A61B 17/07207 227/175.1 |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Mesi et al. |
| 5,782,396 A | 7/1998 | Mastri et al. |
| 5,782,397 A | 7/1998 | Koukline |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A * | 9/1999 | Viola ............... A61B 17/07207 227/176.1 |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,077,287 A | 6/2000 | Taylor et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,459,822 B1 | 10/2002 | Hathaway et al. |
| 6,461,372 B1 | 10/2002 | Jensen et al. |
| 6,471,637 B1 | 10/2002 | Green et al. |
| 6,488,197 B1 | 12/2002 | Whitman |
| 6,491,201 B1 | 12/2002 | Whitman |
| 6,517,565 B1 | 2/2003 | Whitman et al. |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |

(56) References Cited

U.S. PATENT DOCUMENTS

| | | |
|---|---|---|
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,823,592 B2 | 11/2010 | Bettuchi et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,938,307 B2 | 5/2011 | Bettuchi |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,492,146 B2 | 11/2016 | Kostrzewski et al. |
| 10,568,651 B2 | 2/2020 | Kostrzewski et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0130677 A1 | 7/2003 | Whitman et al. |

(56) References Cited

U.S. PATENT DOCUMENTS

| | | |
|---|---|---|
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0232195 A1* | 11/2004 | Shelton, IV ..... A61B 17/07207 227/175.1 |
| 2005/0131442 A1 | 6/2005 | Yachia et al. |
| 2006/0025816 A1 | 2/2006 | Shelton |
| 2006/0142656 A1 | 6/2006 | Malackowski et al. |
| 2006/0142740 A1 | 6/2006 | Sherman et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175949 A1* | 8/2007 | Shelton, IV ......... A61B 17/068 227/176.1 |
| 2007/0175950 A1 | 8/2007 | Shelton et al. |
| 2007/0175951 A1 | 8/2007 | Shelton et al. |
| 2007/0175953 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0095790 A1 | 4/2009 | Whitman et al. |
| 2009/0099876 A1 | 4/2009 | Whitman |
| 2009/0101692 A1 | 4/2009 | Whitman et al. |
| 2009/0138006 A1 | 5/2009 | Bales et al. |
| 2009/0145947 A1 | 6/2009 | Scirica et al. |
| 2009/0171147 A1 | 7/2009 | Lee et al. |
| 2009/0179063 A1 | 7/2009 | Milliman et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0072254 A1 | 3/2010 | Aranyi et al. |
| 2010/0076460 A1 | 3/2010 | Taylor et al. |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0243707 A1 | 9/2010 | Olson et al. |
| 2010/0320252 A1 | 12/2010 | Viola et al. |
| 2011/0006101 A1 | 1/2011 | Hall et al. |
| 2011/0017801 A1 | 1/2011 | Zemlok et al. |
| 2011/0040308 A1 | 2/2011 | Cabrera et al. |
| 2011/0071508 A1 | 3/2011 | Duval et al. |
| 2011/0077673 A1 | 3/2011 | Grubac et al. |
| 2011/0082476 A1 | 4/2011 | Furnish et al. |
| 2011/0089220 A1 | 4/2011 | Ingmanson et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0215132 A1 | 9/2011 | Aranyi et al. |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2011/0297731 A1 | 12/2011 | Aranyi et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |

(56) References Cited

U.S. PATENT DOCUMENTS

| | | | |
|---|---|---|---|
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |

FOREIGN PATENT DOCUMENTS

| | | |
|---|---|---|
| CN | 101856251 A | 10/2010 |
| CN | 101912285 A | 12/2010 |
| CN | 101966093 A | 2/2011 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044888 A2 | 4/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2462880 B1 | 6/2012 |
| EP | 2491872 A1 | 8/2012 |
| EP | 2586381 A1 | 5/2013 |
| EP | 2586382 A2 | 5/2013 |
| EP | 2606812 A1 | 6/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 08038488 | 2/1996 |
| JP | 2005125075 A | 5/2005 |
| JP | 2007216012 A | 8/2007 |
| JP | 2008520362 A | 6/2008 |
| JP | 2009500147 A | 1/2009 |
| JP | 2009066400 A | 4/2009 |
| JP | 2009189830 A | 8/2009 |
| JP | 2010053644 A | 3/2010 |
| JP | 2010240390 A | 10/2010 |
| JP | 2011509715 A | 3/2011 |
| JP | 2011115594 A | 6/2011 |
| JP | 2011520564 A | 7/2011 |
| JP | 2012505718 A | 3/2012 |
| KR | 20120022521 A | 3/2012 |
| WO | 9915086 A1 | 4/1999 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03030743 A2 | 4/2003 |
| WO | 03065916 A1 | 8/2003 |
| WO | 03077769 A1 | 9/2003 |
| WO | 03090630 A2 | 11/2003 |
| WO | 2004107989 A1 | 12/2004 |
| WO | 2006042210 A2 | 4/2006 |
| WO | 2007008669 A2 | 1/2007 |
| WO | 2007016290 A2 | 2/2007 |
| WO | 2007/026354 A1 | 3/2007 |
| WO | 2007026354 A1 | 3/2007 |
| WO | 2007137304 A2 | 11/2007 |
| WO | 2008045361 A2 | 4/2008 |
| WO | 2008131362 A2 | 10/2008 |
| WO | 2008133956 A2 | 11/2008 |
| WO | 2009039506 A1 | 3/2009 |
| WO | 2007014355 A3 | 4/2009 |
| WO | 2009132359 A2 | 10/2009 |
| WO | 2009143092 A1 | 11/2009 |
| WO | 2009149234 A1 | 12/2009 |
| WO | 2010045425 A1 | 4/2010 |
| WO | 2010049031 A1 | 5/2010 |
| WO | 2011108840 A2 | 9/2011 |
| WO | 2012/040984 A1 | 4/2012 |
| WO | 2012040984 A1 | 4/2012 |
| WO | 2012052712 A2 | 4/2012 |

OTHER PUBLICATIONS

Australian Patent Examination Report No. 1, dated Jan. 7, 2016, corresponding to Australian Patent Application No. 2014204542; 4 pages.
International Search Report corresponding to PCT/US2005/027266, completed May 30, 2008 and dated Jun. 18, 2008; (2 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Partial European Search Report corresponding to EP 12 18 6177.7, completed Jan. 30, 2013 and dated Feb. 12, 2013; (6 pp.).
Extended European Search Report corresponding to EP 08 25 2703.7, completed Oct. 23, 2008 and dated Oct. 31, 2008; (7 pp.).
Extended European Search Report corresponding to EP No. 13 16 3033.7, completed Jun. 27, 2013 and dated Jul. 15, 2013; (8 pp).
Extended European Search Report corresponding to EP No. 11 17 8021.9, dated Jun. 4, 2013; (3 pp).
Extended European Search Report corresponding to EP No. 12 18 6177.7, completed Aug. 14, 2013 and dated Aug. 23, 2013; (8 pp).
Partial European Search Report corresponding to EP No. 13 17 2400.7, completed Sep. 18, 2013 and dated Oct. 1, 2013; (7 pp).
Partial European Search Report corresponding to EP No. 13 17 1742.3, completed Sep. 17, 2013 and dated Sep. 25, 2013; (8 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 08 25 2703.7, completed Oct. 23, 2008 and dated Oct. 31, 2008; (7 pp).

(56) References Cited

OTHER PUBLICATIONS

Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
Extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
Extended European Search Report corresponding to European Application No. 12186170.2, dated Sep. 3, 2014; 3 pages.
Extended European Search Report corresponding to EP 06 78 8914.7, completed May 3, 2012 and dated May 11, 2012; (8 pp.).
European Communication dated Nov. 17, 2015, corresponding to European Application No. 12 186 177.7; 3 pages.
Chinese Office Action corresponding to counterpart Int'l Appln. No. CN 201310125449.6, dated Feb. 3, 2016; and English Translation.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 15 9056.2 dated Oct. 26, 2015.
European Office Action corresponding to International Application No. EP 14 18 4882.0 dated Apr. 25, 2016.
Extended European Search Report corresponding to International Application No. EP 14 19 6704.2 dated Sep. 24, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
International Search Report and Written Opinion corresponding to Int'l Appln. No. PCT/US2015/051837, dated Dec. 21, 2015.
Australian Examination Report No. 1, dated Aug. 8, 2016, corresponding to Australian Application No. 2012227315; 3 pages.
Australian Examination Report No. 1, dated Sep. 13, 2016, corresponding to Australian Application No. 2012227309; 4 pages.
Extended European Search Report dated Oct. 6, 2016, corresponding to European Application No. 16157090.8; 13 pages.
European Communication dated Dec. 23, 2016, corresponding to European Applicaiton No. 12 186 170.2; 3 pages.
Australian Examination Report No. 1, dated Mar. 6, 2017, corresponding to Australian Application No. 2013206098; 3 pages.
Japanese Office Action (with English translation), dated Mar. 8, 2017, corresponding to Japanese Application No. 2013-123772; 7 total pages.
Japanese Office Action (with English tranlsation), dated Nov. 15, 2017, corresponding to Japanese Application No. 2013-123772; 6 total pages.
Japanese Office Action (with English Summary Form), dated Nov. 29, 2017, corresponding to Japanese Application 2017-034831; 5 total pages.
European Communication dated Jan. 29, 2018, corresponding to Europeaen Appliaction No. 12186177.7; 4 pages.
Japanese Office Action (with English Summary Form) dated Mar. 16, 2018, corresponding to Japanese Counterpart Application No. 2013-123772; 5 total pages.
Japanese Office Action (with English translation) dated Oct. 24, 2018, corresponding to Japanese Application No. 2018-026764; 5 total pages.
International Search Report from the corresponding EP Application No. 12186177.7 dated Aug. 23, 2013.
European Search Report corresponding to European Application EP 10 25 2037.6; completed Mar. 1, 2011 and dated Mar. 9, 2011; 3 pages.
Canadian Office Action, dated May 30, 2018, corresponding to Canadian Patent Application No. 2,790,622.
Canadian Office Action, dated May 30, 2018, corresponding to Canadian Patent Application No. 2,790,528.
Partial European Search Report corresponding to EP 13 17 1742.3, completed Sep. 17, 2013 and dated Sep. 25, 2013; (8 pp).
Extended European Search Report corresponding to European Application No. 12186170.2, dated Sep. 3, 2014; 8 pages.
European Communication dated Jan. 29, 2018, corresponding to European Application No. 12186177.7; 4 pages.
The extended European Search Report from Application No. EP 13177163.6 dated Feb. 6, 2014.
Extended European Search Report corresponding to EP No. 13 16 30317, completed Jun. 27, 2013 and dated Jul. 15, 2013; (8 pp).
European Search Report for EP 12186177.7 date of completion is Jan. 30, 2013 (6 pages).
Extended European Search Report corresponding to EP 13 16 3033.7, completed Jun. 27, 2013, and dated Jul. 15, 2013; (8 pp).
Extended European Search Report corresopnding to European Application No. 12186170.2, dated Sep. 3, 2014; 8 pages.
European Search Report for EP 10252037.6 date of completion is Mar. 1, 2011 (3 pages).
European Search Report for EP 12186177.7 date of completion is Aug. 14, 2013 (10 pages).

* cited by examiner

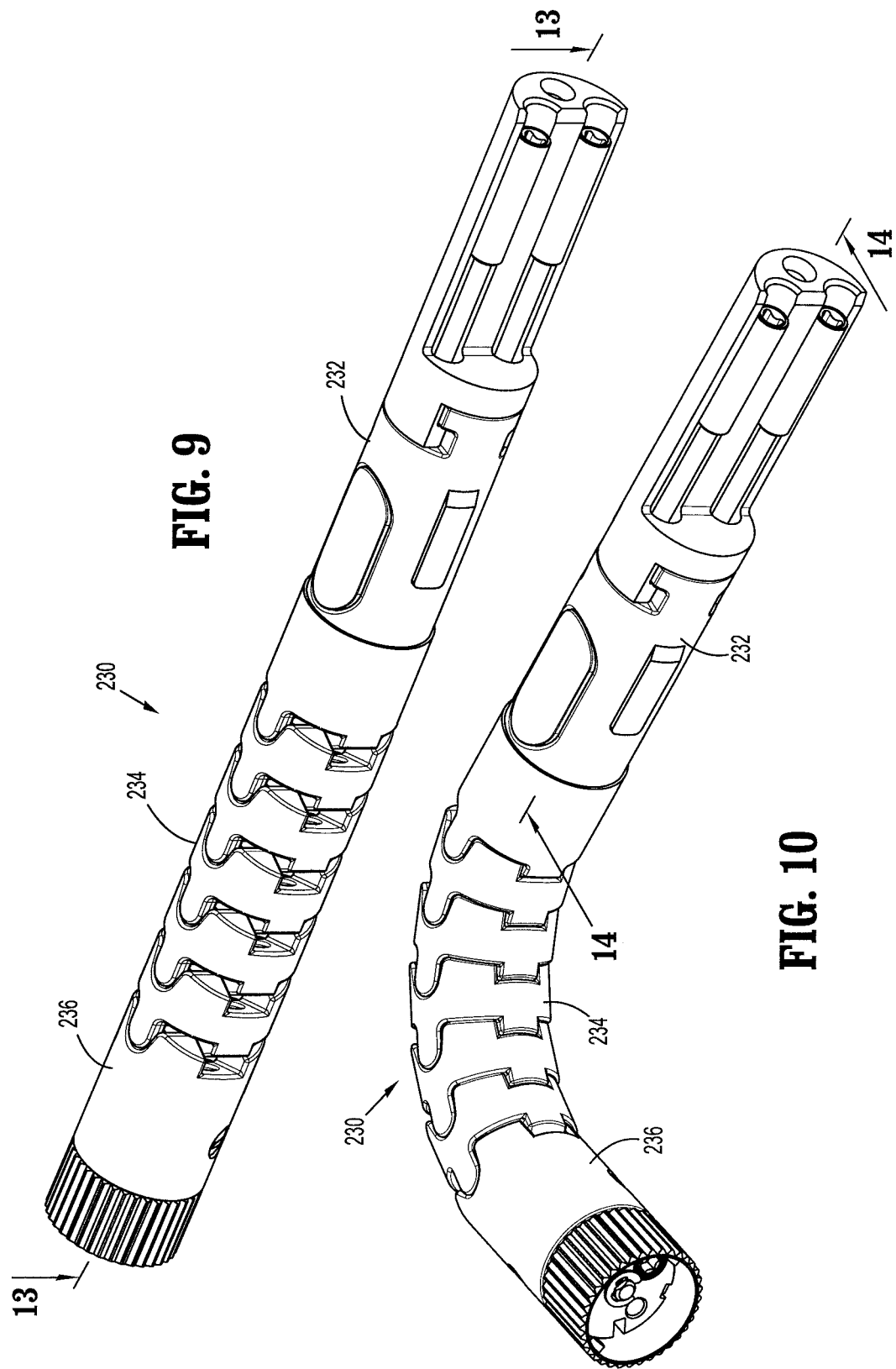

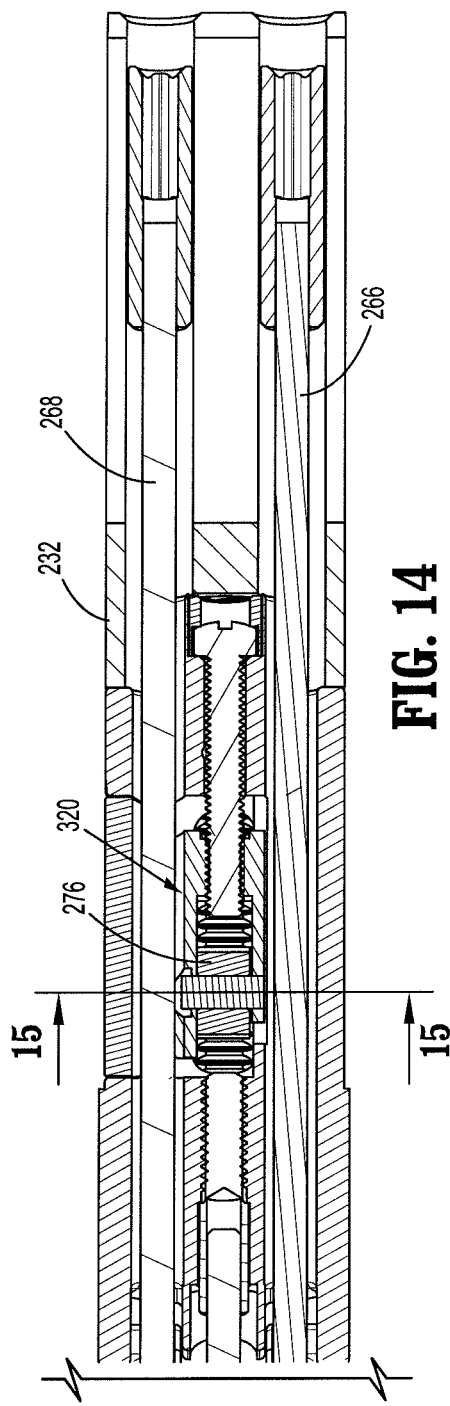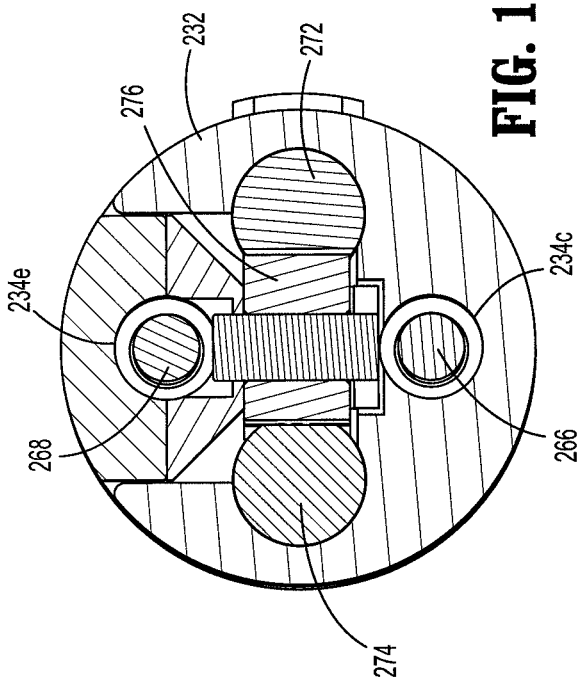

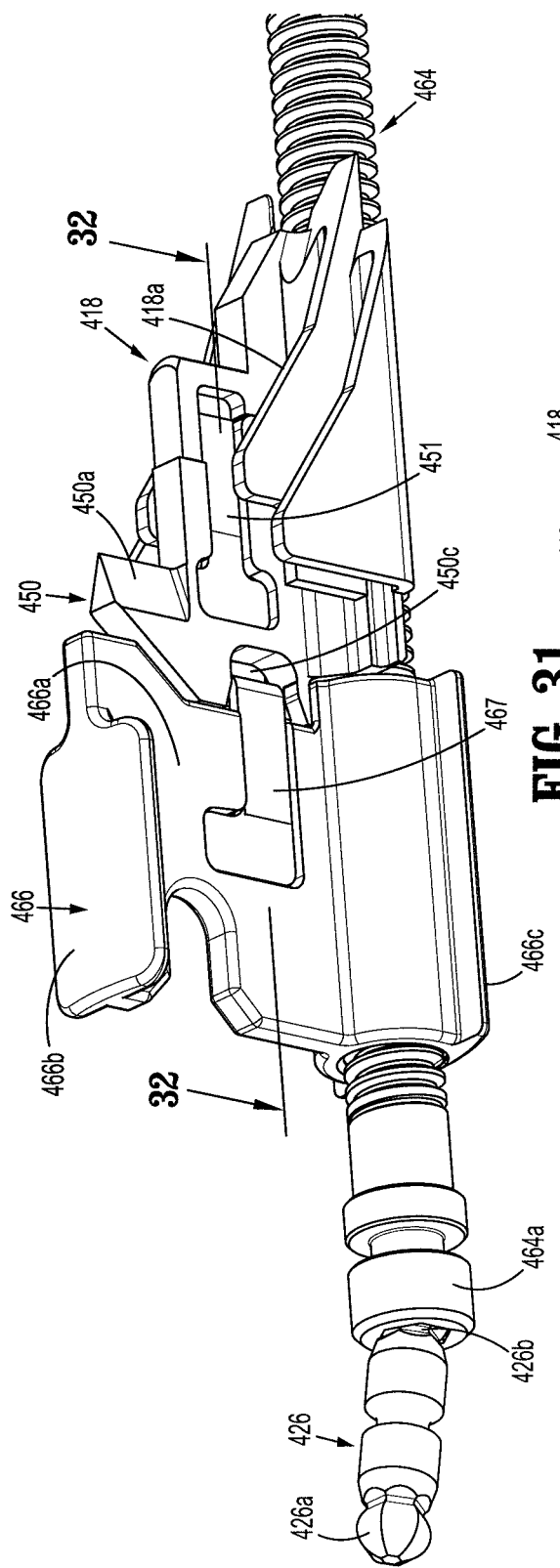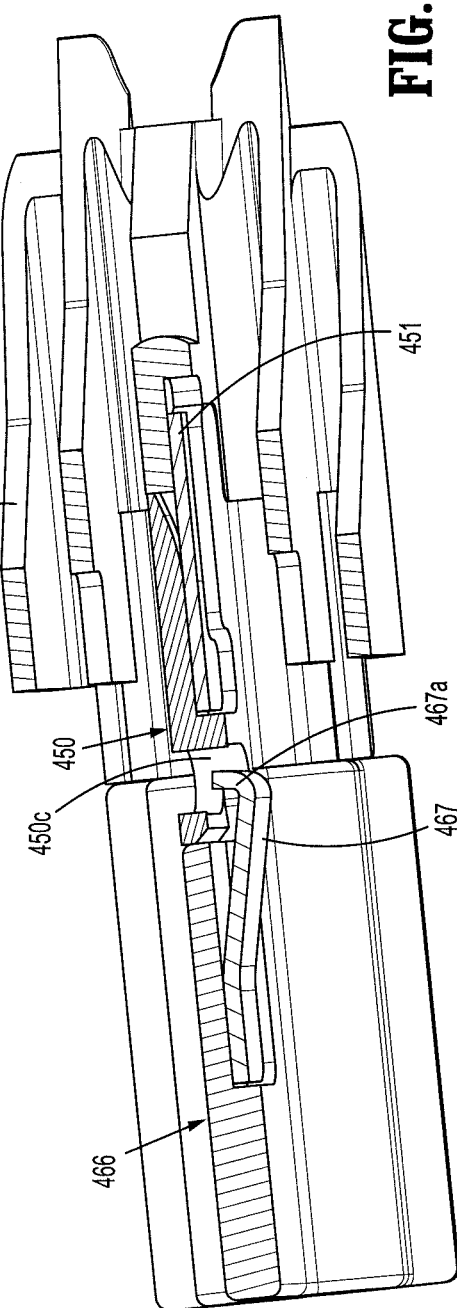

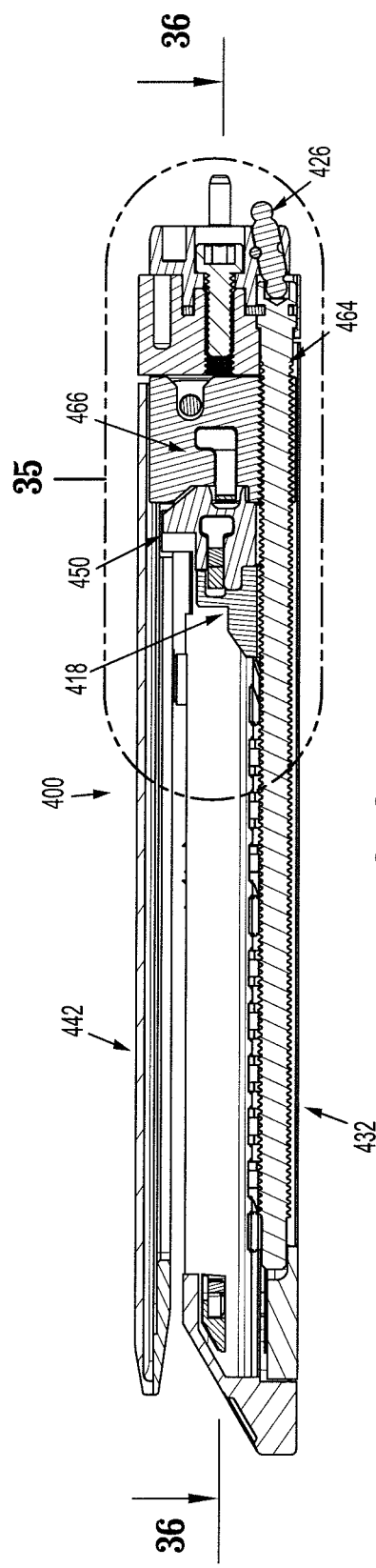
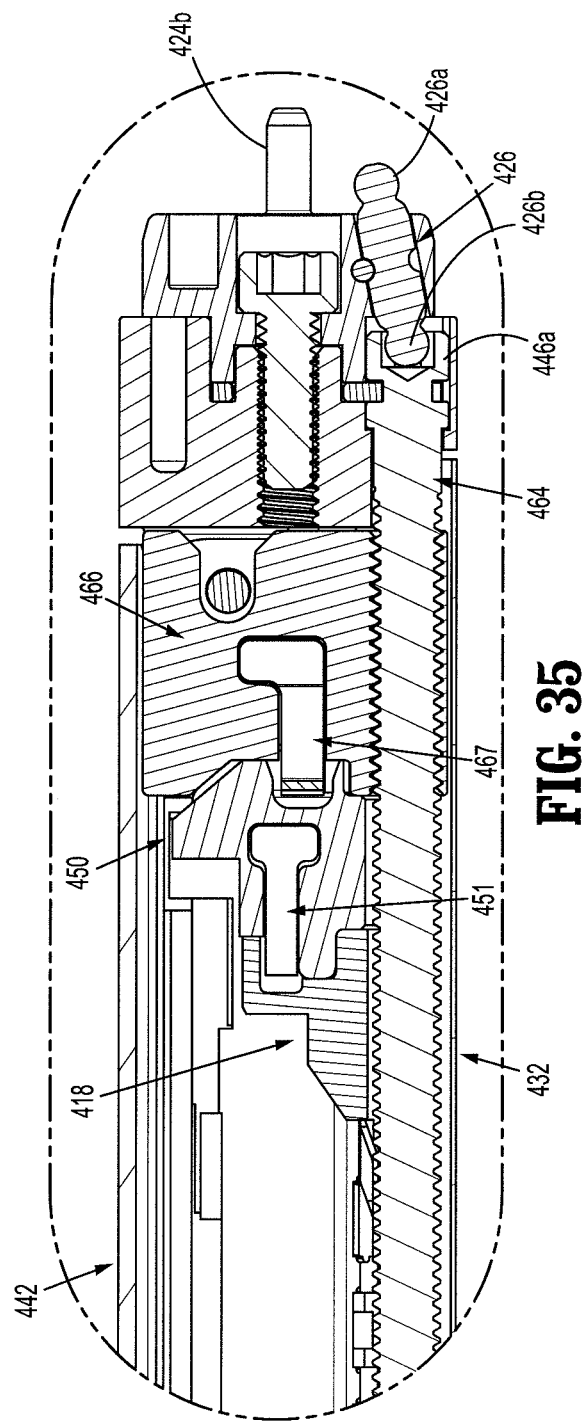
FIG. 34
FIG. 35

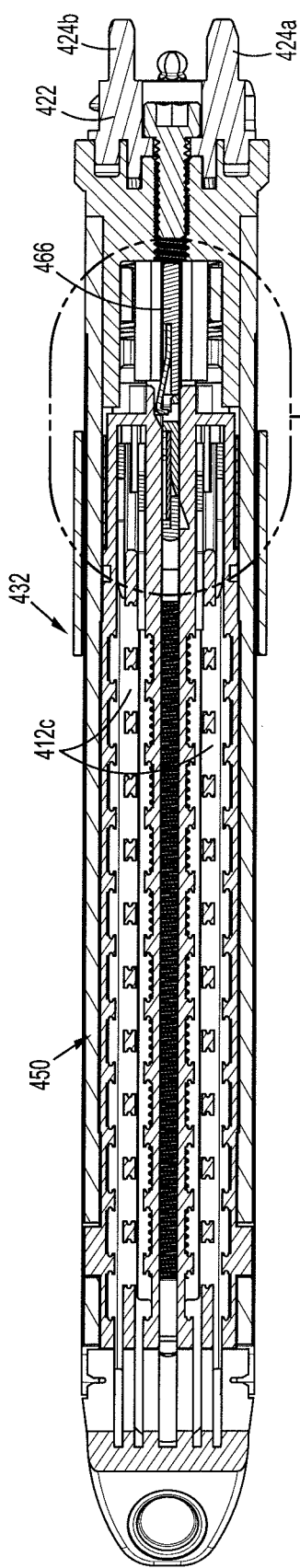

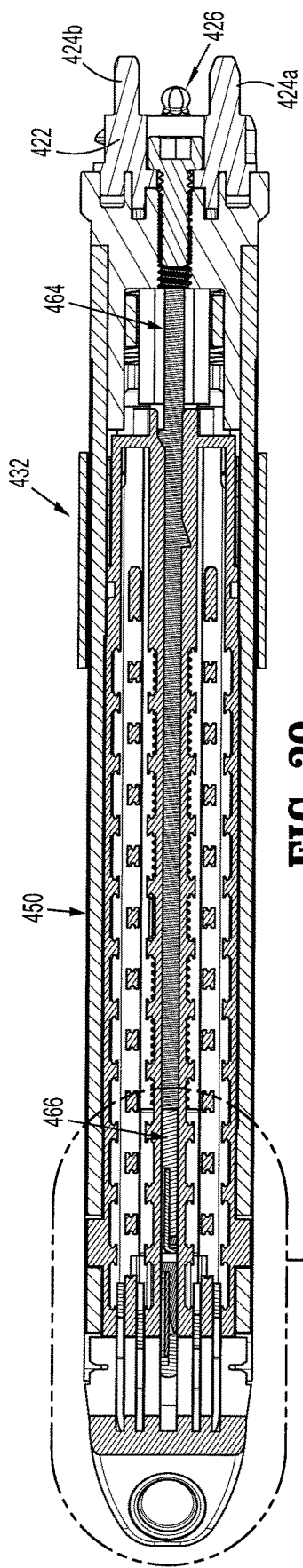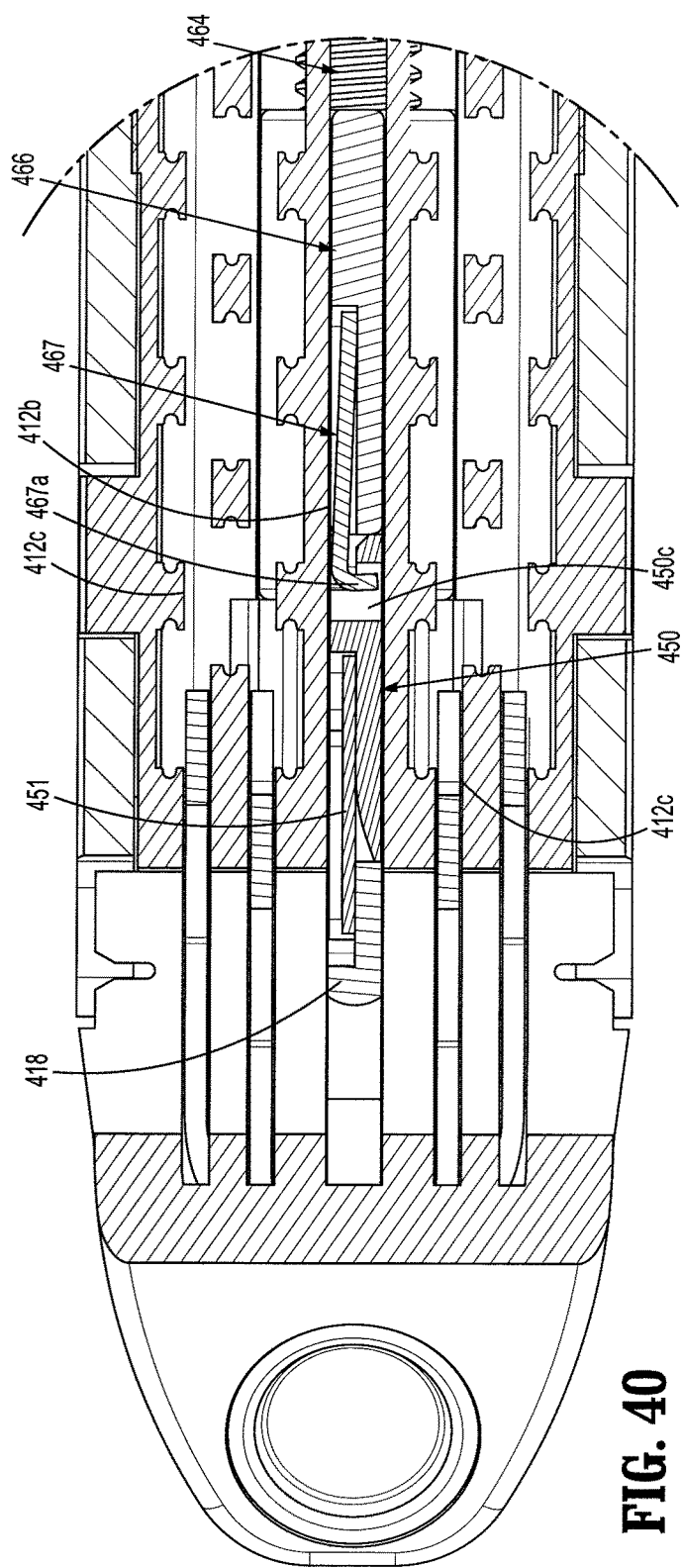

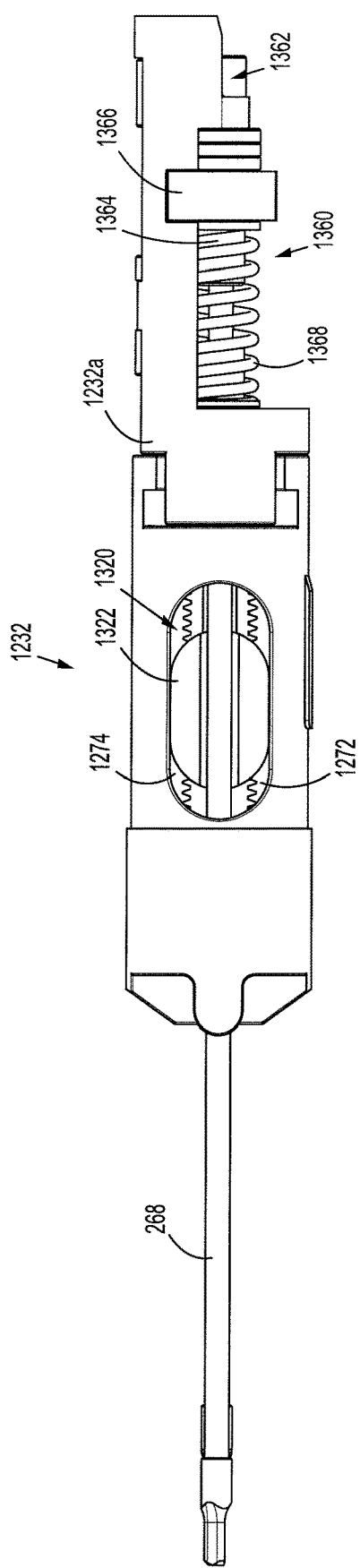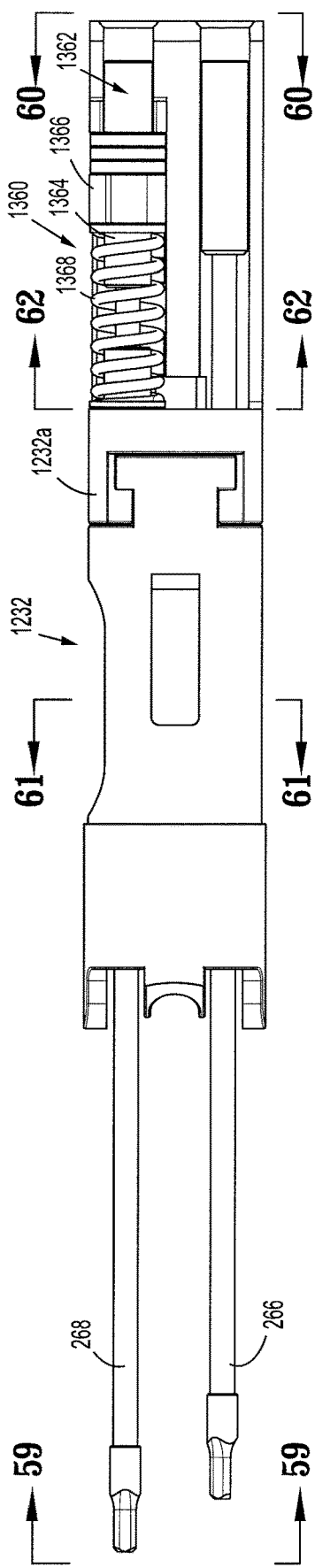
FIG. 52
FIG. 53

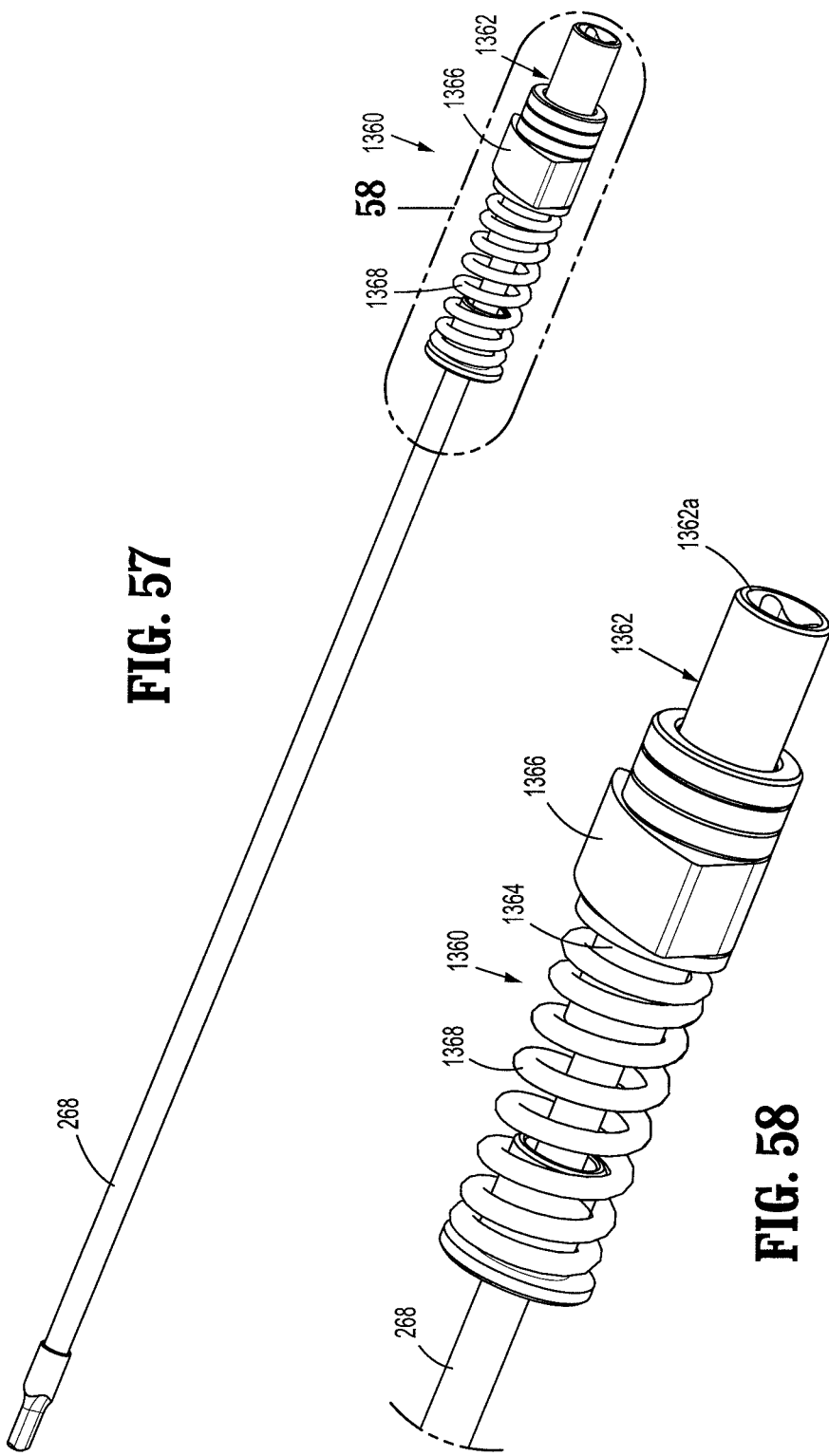

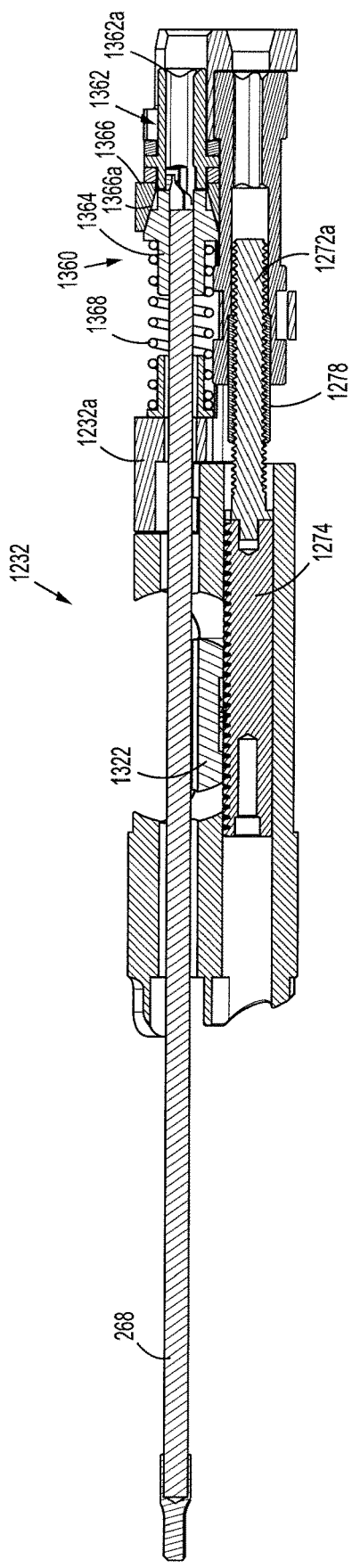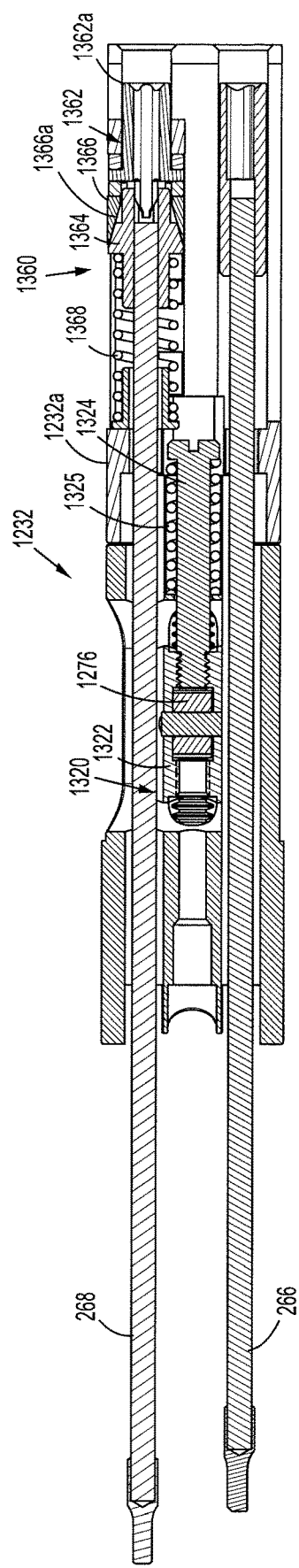

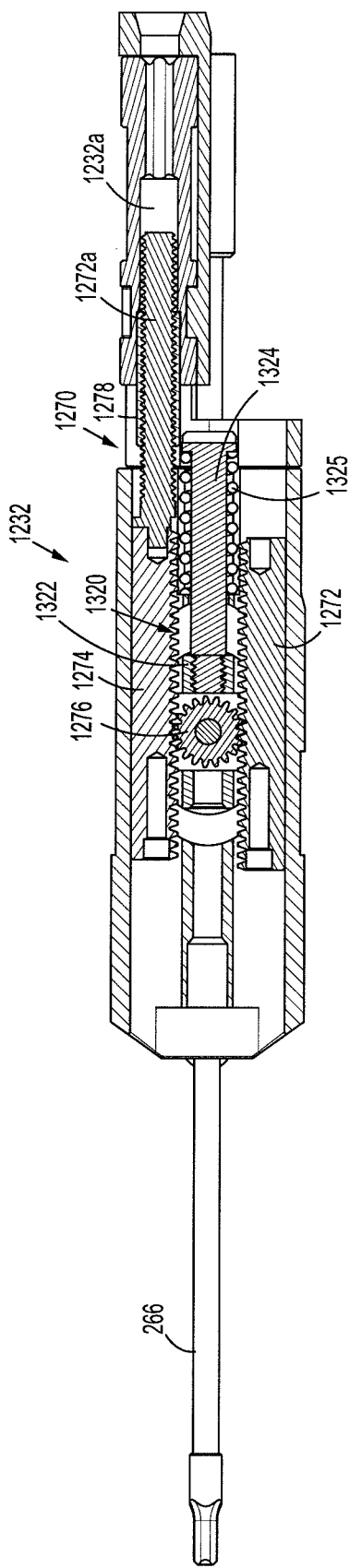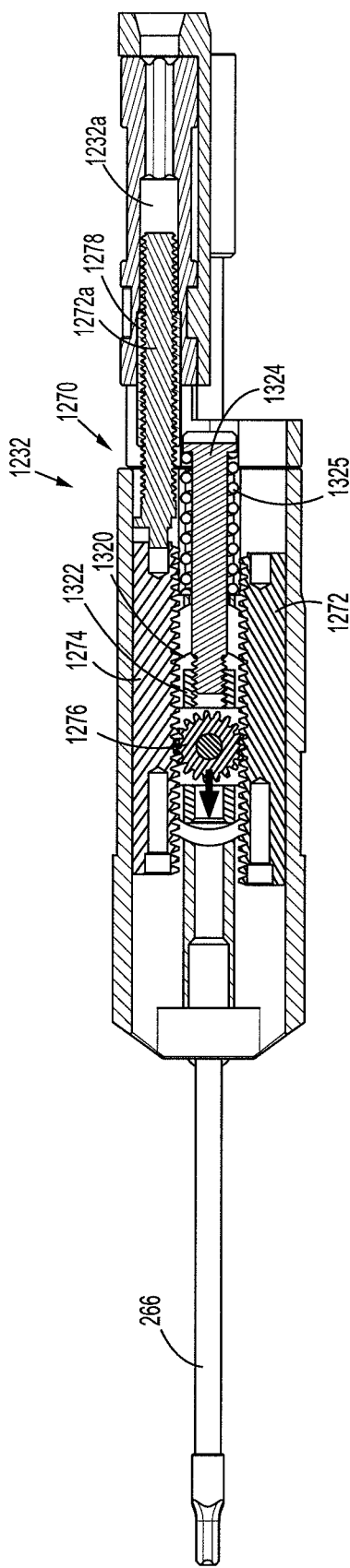

APPARATUS FOR ENDOSCOPIC PROCEDURES

CROSS-REFERENCE TO RELATED APPLICATIONS

This application is a continuation claiming the benefit of and priority to U.S. patent application Ser. No. 16/738,076, filed Jan. 9, 2020, which is a continuation claiming the benefit of and priority to U.S. patent application Ser. No. 15/294,813, filed on Oct. 17, 2016, (now U.S. Pat. No. 10,568,651), which is a divisional claiming the benefit of and priority to U.S. patent application Ser. No. 13/891,288, filed on May 10, 2013 (now U.S. Pat. No. 9,492,146), which is a continuation-in-part claiming the benefit of and priority to U.S. patent application Ser. No. 13/444,228, filed on Apr. 11, 2012 (now U.S. Pat. No. 8,672,206), which is a continuation-in-part claiming the benefit of and priority to each of U.S. patent application Ser. No. 13/280,898, filed on Oct. 25, 2011 (now U.S. Pat. No. 8,899,462) and U.S. patent application Ser. No. 13/280,859, filed on Oct. 25, 2011 (U.S. Pat. No. 8,657,177), the entire contents of each of which are incorporated by reference herein.

U.S. patent application Ser. No. 13/891,288, filed on May 10, 2013 (now U.S. Pat. No. 9,492,146), also claims the benefit of and priority to each of U.S. Provisional Patent Application No. 61/779,873, filed on Mar. 13, 2013, U.S. Provisional Patent Application 61/672,891, filed on Jul. 18, 2012, and U.S. Provisional Patent Application 61/659,116, filed on Jun. 13, 2012, the entire contents of each of which are incorporated by reference herein.

BACKGROUND

1. Technical Field

The present disclosure relates to surgical apparatus, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating electromechanical surgical devices. Some electromechanical surgical devices include a handle assembly, which is reusable, and replaceable loading units and/or single use loading units or the like that are selectively connected to the handle assembly prior to use and then disconnected from the handle assembly following use, in order to be disposed of or in some instances sterilized for re-use.

Many of these electromechanical surgical devices are relatively expensive to manufacture, purchase and/or operate. There is a desire by manufactures and end users to develop electromechanical surgical devices that are relatively inexpensive to manufacture, purchase and/or operate.

Accordingly, a need exists for electromechanical surgical apparatus, devices and/or systems that are relatively economical to develop and manufacture, to store and ship, as well as economical and convenient to purchase and use from the end user's perspective.

SUMMARY

According to an aspect of the present disclosure, an electromechanical surgical system comprises an instrument housing defining a connecting portion for selectively connecting with a shaft assembly, and having at least one rotatable drive member. An end effector is configured to perform at least one function, and the shaft assembly is arranged for selectively interconnecting the end effector and the instrument housing, the shaft assembly including at least one rotatable drive member and at least one link for allowing articulation of the end effector. First and second diametrically opposed articulation cables extend at least partially along the at least one link. Each articulation cable includes a distal end anchored to the at least one link, and a proximal end being secured to a respective first and second axially displaceable rack, each rack being operatively connected to one another by a spur gear. The spur gear is attached to a clevis. The system includes a cable tensioning assembly attached to the spur gear and including a screw and a biasing member between the screw and the clevis, and a clutch mechanism attached to at least one of the at least one drive member of the shaft assembly.

In certain embodiments, the shaft assembly further includes: a threaded rod extending proximally from the first rack; and wherein rotation of the at least one drive member of the shaft assembly imparts rotation to the threaded rod and to move the first rack and articulate the end effector. The shaft assembly may further include: a distal neck housing supported at a distal end of the at least one link, a first articulation cable including a distal end secured to the at least one link and a proximal end secured to the first rack; and a second articulation cable including a distal end secured to the at least one link and a proximal end secured to the second rack, the first and second articulation cables diametrically opposed to one another.

Rotation of threaded rod may translate the first rack to axially displace the first articulation cable to articulate the end effector. The clevis can be axially slidable and rotatably supporting the spur gear. Axial displacement of the clevis can result in axial displacement of the spur gear and, in turn, the first rack and the second rack.

The clevis is desirably biased in a proximal direction. The clevis is connected to the screw to axially displace the clevis upon a rotation of the adjustment screw. The clutch mechanism can have a plunger member with camming surfaces and a coupling member with camming surfaces. In certain embodiments, the clutch mechanism includes a biasing member engaged with the plunger member to press the plunger member against the coupling member so that the camming surfaces of the plunger member are in engagement with the camming surfaces of the coupling member.

In certain embodiments, the clutch mechanism includes a coupler defining an angled inner-annular surface for mating with an angled outer annular profile of the plunger member.

In a further aspect of the present disclosure, an electromechanical surgical system comprises an instrument housing defining a connecting portion for selectively connecting with a shaft assembly, the surgical instrument having at least one rotatable drive member, an end effector configured to perform at least one function and having a rotation hub, and the shaft assembly is arranged for selectively interconnecting the end effector and the instrument housing, the shaft assembly including at least one drive member, the at least one drive member of the shaft assembly being connectable to the rotation hub when the shaft assembly is connected to the end effector. The shaft assembly has a clutch mechanism attached to at least one of the at least one drive member of the shaft assembly.

The clutch mechanism may have a plunger member with camming surfaces and a coupling member with camming surfaces. The clutch mechanism, in certain embodiments, includes a biasing member engaged with the plunger member to press the plunger member against the coupling member so that the camming surfaces of the plunger member are in engagement with the camming surfaces of the coupling member.

Further details and aspects of exemplary embodiments of the present invention are described in more detail below with reference to the appended figures.

BRIEF DESCRIPTION OF THE DRAWINGS

Embodiments of the present disclosure are described herein with reference to the accompanying drawings, wherein:

FIG. 9 is a perspective view of a neck assembly of the shaft assembly, shown in a straight orientation;

FIG. 10 is a perspective view of the neck assembly of FIG. 9, shown in an articulated condition;

FIG. 14 is a cross-sectional view of the neck assembly of FIGS. 9-12, as taken through 14-14 of FIG. 10;

FIG. 15 is a cross-sectional view of the neck assembly of FIGS. 9-12, as taken through 15-15 of FIG. 14;

FIG. 31 is a further perspective view of the drive beam, the knife sled and the actuation sled of the end effector of FIGS. 27-29;

FIG. 32 is a cross-sectional view as taken through 32-32 of FIG. 31;

FIG. 34 is a cross-sectional view of the end effector of FIG. 27, as taken through 34-34 of FIG. 27, illustrating the drive beam, the knife sled and the actuation sled in a proximal-most position;

FIG. 35 is an enlarged view of the indicated area of detail of FIG. 34;

FIG. 36 is a cross-sectional view of the end effector of FIG. 27, as taken through 36-36 of FIG. 34;

FIG. 37 is an enlarged view of the indicated area of detail of FIG. 36;

FIG. 39 is a cross-sectional view of the end effector of FIG. 27, as taken through 34-34 of FIG. 27, illustrating the drive beam, the knife sled and the actuation sled in a distal-most position;

FIG. 40 is an enlarged view of the indicated area of detail of FIG. 39;

FIG. 52 is a top, plan view of the proximal portion of the neck assembly of FIGS. 50 and 51;

FIG. 53 is a side, elevational view of the proximal portion of the neck assembly of FIGS. 50 and 51;

FIG. 57 is a perspective view of a clutch assembly of the neck assembly of FIGS. 50 and 51;

FIG. 58 is an enlarged view of the indicated area of detail of FIG. 57;

FIG. 63 is a cross-sectional view of the proximal portion of the neck assembly of FIGS. 50 and 51, as taken through 63-63 of FIG. 59;

FIG. 64 is a cross-sectional view of the proximal portion of the neck assembly of FIGS. 50 and 51, as taken through 64-64 of FIG. 59;

FIG. 65 is a cross-sectional view of the proximal portion of the neck assembly of FIGS. 50 and 51, as taken through 65-65 of FIG. 59; and FIG. 66 is the cross-sectional view of FIG. 65, showing another position.

DETAILED DESCRIPTION OF EMBODIMENTS

Figure 1:
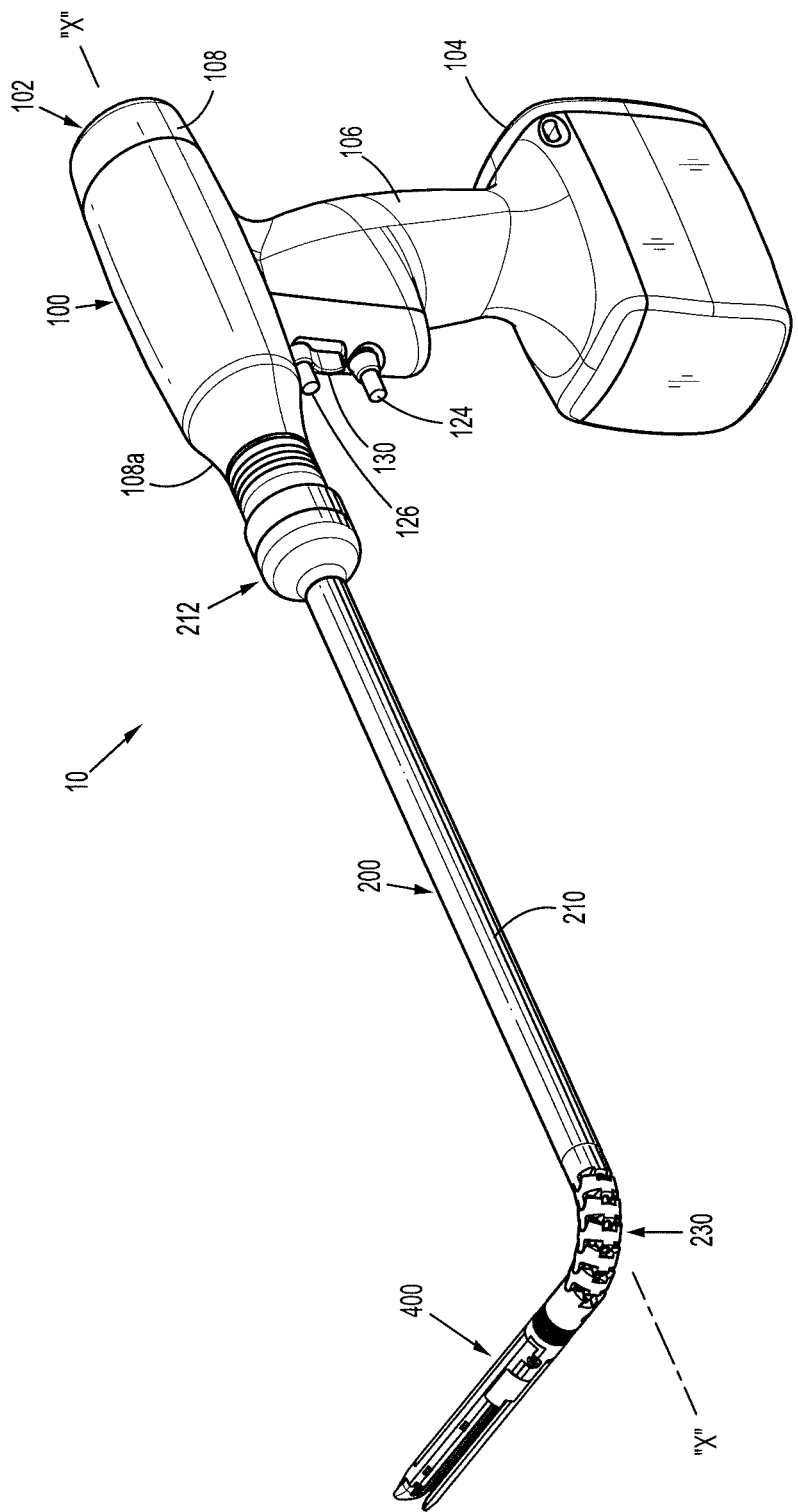
FIG. 1 is a perspective view of an electromechanical surgical system according to an embodiment of the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user.

Figure 2:
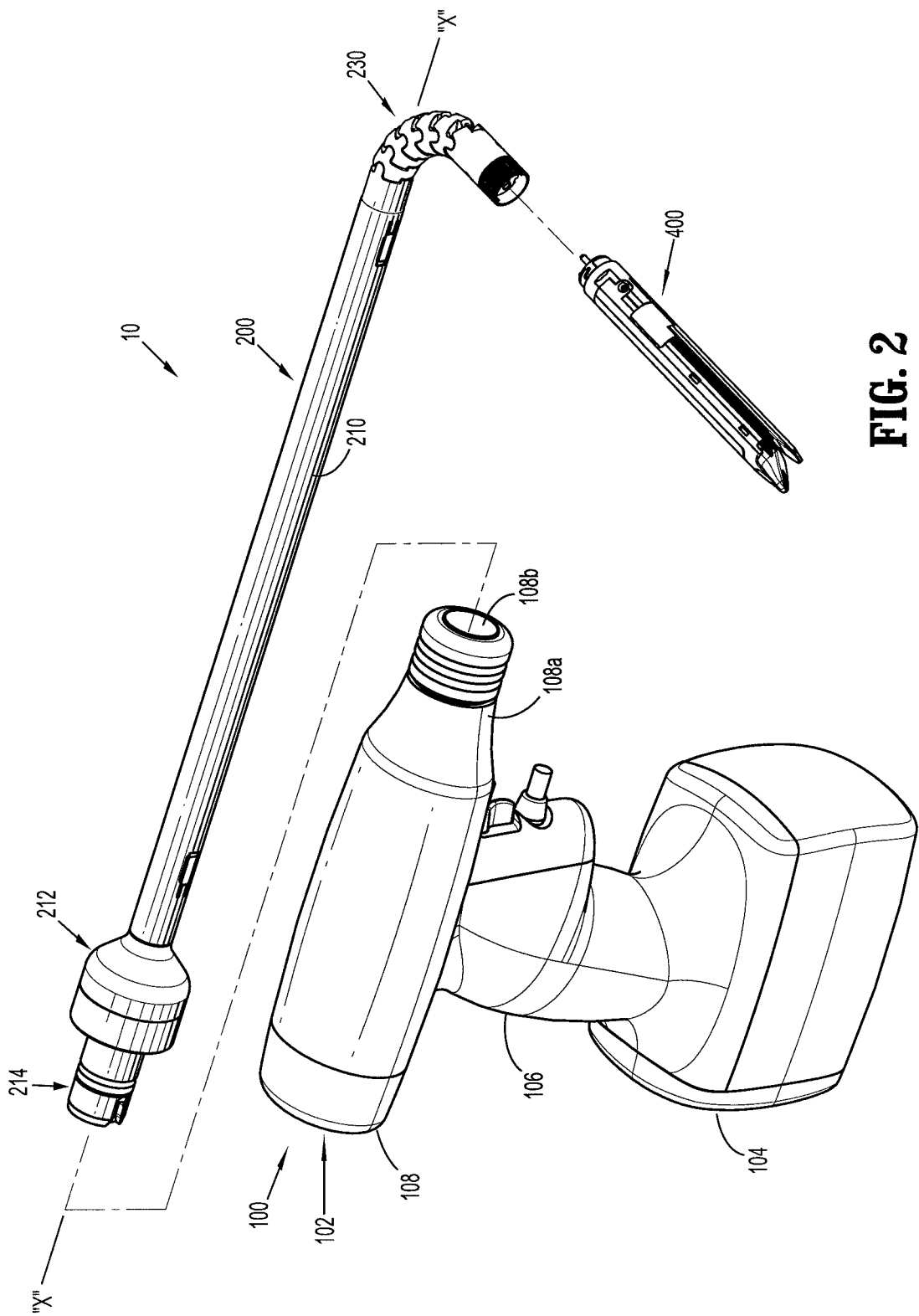
FIG. 2 is a perspective view, with parts separated, of the electromechanical surgical system of FIG. 1.
Figure 3:
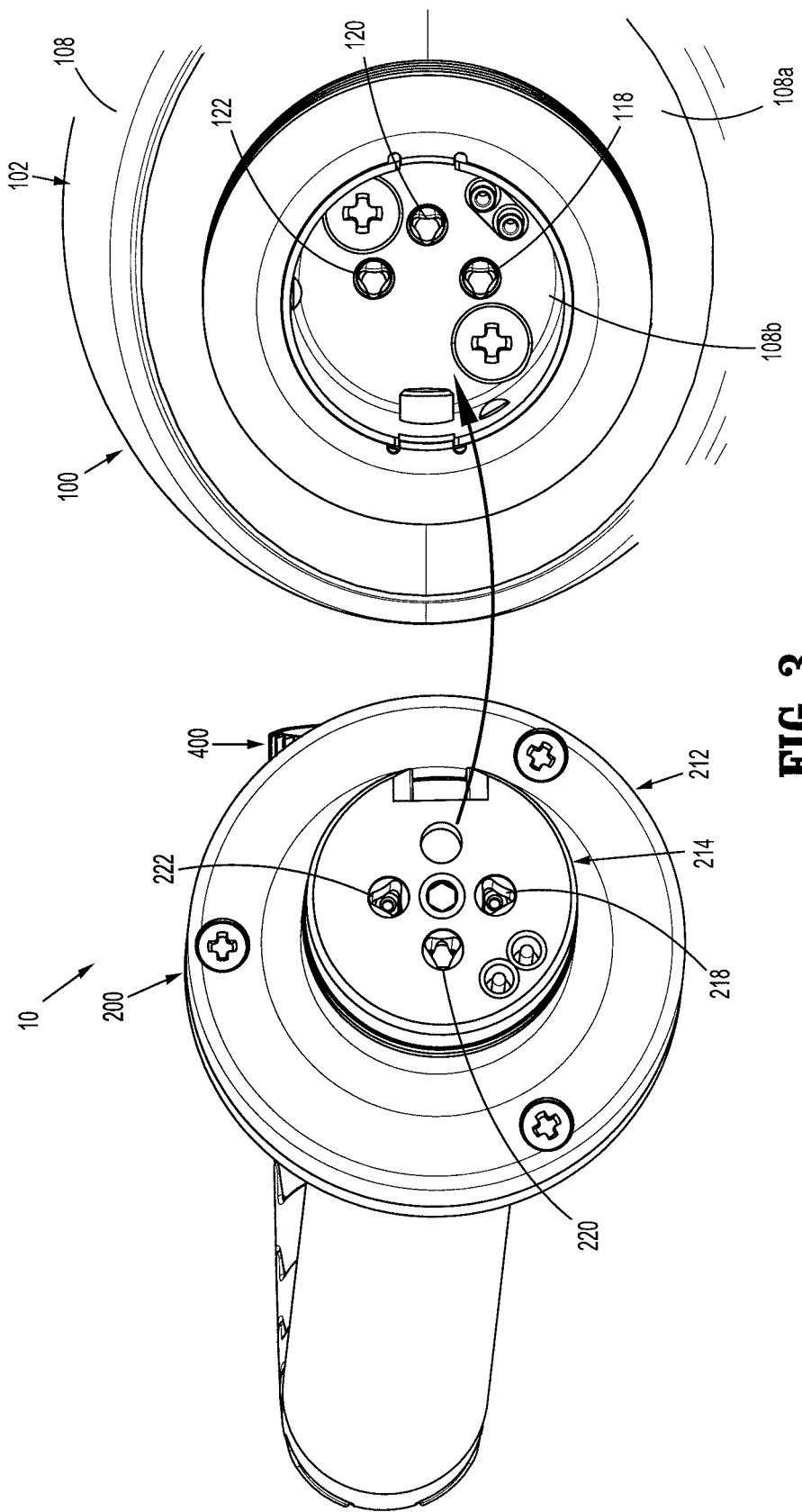
FIG. 3 is a rear, perspective view of a shaft assembly and a powered surgical instrument, of the electromechanical surgical system of FIGS. 1 and 2, illustrating a connection therebetween.

Referring initially to FIGS. 1-3, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 400, via a shaft assembly 200, that are each configured for actuation and manipulation by the electromechanical, hand-held, powered surgical instrument 100. In particular, surgical instrument 100 is configured for selective connection with shaft assembly 200, and, in turn, shaft assembly 200 is configured for selective connection with any one of a plurality of different end effectors 400.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009 (U.S. Patent Publication No. 2011-0121049), the entire content of each of which are hereby incorporated herein by reference, for a detailed description of the construction and operation of exemplary electromechanical, hand-held, powered surgical instrument 100

Generally, as illustrated in FIGS. 1-3, surgical instrument 100 includes an instrument housing 102 having a lower housing portion 104, an intermediate housing portion 106 extending from and/or supported on lower housing portion 104, and an upper housing portion 108 extending from and/or supported on intermediate housing portion 106. The surgical instrument 100 has a controller for controlling certain functions of the surgical system, collecting data, and performing other functions. Instrument housing 102 defines a cavity therein in which a circuit board (not shown) and a drive mechanism (not shown) are situated.

The circuit board is configured to control the various operations of surgical instrument 100, as will be set forth in additional detail below. In accordance with the present disclosure, instrument housing 102 provides a housing in which a rechargeable battery (not shown), is removably situated. The battery is configured to supply power to any of the electrical components of surgical instrument 100.

Upper housing portion 108 of instrument housing 102 defines a nose or connecting portion 108a configured to accept a corresponding shaft coupling assembly 214 of transmission housing 212 of shaft assembly 200. As seen in FIG. 3, connecting portion 108a of upper housing portion 108 of surgical instrument 100 has a cylindrical recess 108b that receives shaft coupling assembly 214 of transmission housing 212 of shaft assembly 200 when shaft assembly 200 is mated to surgical instrument 100. The connecting portion 108a of the surgical instrument 100 has at least one rotatable drive member. In particular, connecting portion 108a houses three rotatable drive members or connectors 118, 120, 122, each independently actuatable and rotatable by the drive mechanism (not shown) housed within instrument housing 102.

Upper housing portion 108 of instrument housing 102 provides a housing in which the drive mechanism (not shown) is situated. The drive mechanism is configured to drive shafts and/or gear components in order to perform the various operations of surgical instrument 100. In particular, the drive mechanism is configured to drive shafts and/or gear components in order to selectively move end effector 400 relative to shaft assembly 200; to rotate anvil assembly 200 and/or end effector 400, about a longitudinal axis "X" (see FIGS. 1 and 2), relative to instrument housing 102; to move an upper jaw or anvil assembly 442 of end effector 400 relative to a lower jaw or cartridge assembly 432 of end effector 400; to articulate and/or rotate the shaft assembly; and/or to fire a stapling and cutting cartridge within cartridge assembly 432 of end effector 400.

The shaft assembly 200 has a force transmitting assembly for interconnecting the at least one drive member of the surgical instrument to at least one rotation receiving member of the end effector. The force transmitting assembly has a first end that is connectable to the at least one rotatable drive member and a second end that is connectable to the at least one rotation receiving member of the end effector. When shaft assembly 200 is mated to surgical instrument 100, each of rotatable drive members or connectors 118, 120, 122 of surgical instrument 100 couples with a corresponding rotatable connector sleeve 218, 220, 222 of shaft assembly 200 (see FIGS. 3 and 5). In this regard, the interface between corresponding first drive member or connector 118 and first connector sleeve 218, the interface between corresponding second drive member or connector 120 and second connector sleeve 220, and the interface between corresponding third drive member or connector 122 and third connector sleeve 222 are keyed such that rotation of each of drive members or connectors 118, 120, 122 of surgical instrument 100 causes a corresponding rotation of the corresponding connector sleeve 218, 220, 222 of shaft assembly 200.

The mating of drive members or connectors 118, 120, 122 of surgical instrument 100 with connector sleeves 218, 220, 222 of shaft assembly 200 allows rotational forces to be independently transmitted via each of the three respective connector interfaces. The drive members or connectors 118, 120, 122 of surgical instrument 100 are configured to be independently rotated by the drive mechanism. In this regard, the controller has a function selection module (not shown) of the drive mechanism selects which drive member or connector 118, 120, 122 of surgical instrument 100 is to be driven by an input drive component (not shown) of the drive mechanism.

Since each of drive members or connectors 118, 120, 122 of surgical instrument 100 has a keyed and/or substantially non-rotatable interface with respective connector sleeves 218, 220, 222 of shaft assembly 200, when shaft assembly 200 is coupled to surgical instrument 100, rotational force(s) are selectively transferred from the drive mechanism of surgical instrument 100 to shaft assembly 200, and on to end effector 400, as will be discussed in greater detail below.

The selective rotation of drive member(s) or connector(s) 118, 120 and/or 122 of surgical instrument 100 allows surgical instrument 100 to selectively actuate different functions of end effector 400. As will be discussed in greater detail below, selective and independent rotation of first drive member or connector 118 of surgical instrument 100 corresponds to the selective and independent opening and closing of end effector 400, and driving of a stapling/cutting component of end effector 400. Also, the selective and independent rotation of second drive member or connector 120 of surgical instrument 100 corresponds to the selective and independent articulation of end effector 400 transverse to longitudinal axis "X" (see FIG. 1). Additionally, the selective and independent rotation of third drive member or connector 122 of surgical instrument 100 corresponds to the selective and independent rotation of end effector 400 about longitudinal axis "X" (see FIG. 1) relative to instrument housing 102 of surgical instrument 100.

In accordance with the present disclosure, the drive mechanism may include a selector gearbox assembly (not shown); a function selection module (not shown), located proximal to the selector gearbox assembly, that functions to selectively move gear elements within the selector gearbox assembly into engagement with a second motor (not shown). The drive mechanism may be configured to selectively drive one of drive members or connectors 118, 120, 122 of surgical instrument 100, at a given time.

As illustrated in FIGS. 1 and 2, instrument housing 102 supports a pair of finger-actuated control buttons 124, 126 and/or rocker device(s) 130 (only one rocker device being shown). Each one of the control buttons 124, 126 and rocker device(s) 130 includes a respective magnet (not shown) that is moved by the actuation of an operator. In addition, the circuit board (not shown) housed in instrument housing 102 includes, for each one of the control buttons 124, 126 and rocker device(s) 130, respective Hall-effect switches (not shown) that are actuated by the movement of the magnets in the control buttons 124, 126 and rocker device(s) 130. In particular, located immediately proximal to the control button 124 is a respective Hall-effect switch (not shown) that is actuated upon the movement of a magnet within the control button 124 upon the operator actuating control button 124. The actuation of Hall-effect switch (not shown), corresponding to control button 124, causes the circuit board to provide appropriate signals to the function selection module and the input drive component of the drive mechanism to close end effector 400 and/or to fire a stapling/cutting cartridge within end effector 400.

Also, located immediately proximal to control button 126 is a respective Hall-effect switch (not shown) that is actuated upon the movement of a magnet (not shown) within control button 126 upon the operator actuating control button 126. The actuation of the Hall-effect switch, corresponding to control button 126, causes the circuit board to provide appropriate signals to the function selection module and the input drive component of the drive mechanism to open/close end effector 400.

In addition, located immediately proximal to rocker device 130 is a respective Hall-effect switch (not shown) that is actuated upon the movement of a magnet (not shown) within rocker device 130 upon the operator actuating rocker device 130. The actuation of the Hall-effect switch, corresponding to rocker device 130, causes the circuit board to provide appropriate signals to the function selection module and the input drive component of the drive mechanism to rotate end effector 400 relative to shaft assembly 200 or rotate end effector 400 and shaft assembly 200 relative to instrument housing 102 of surgical instrument 100. Specifically, movement of rocker device 130 in a first direction causes end effector 400 and/or shaft assembly 200 to rotate relative to instrument housing 102 in a first direction, while movement of rocker device 130 in an opposite, e.g., second, direction causes end effector 400 and/or shaft assembly 200 to rotate relative to instrument housing 102 in an opposite, e.g., second, direction.

Turning now to FIGS. 1-26, shaft assembly 200 will be shown in detail and described. Shaft assembly 200 is configured to communicate the rotational forces of first, second and third rotatable drive members or connectors 118, 120, and 122 of surgical instrument 100 to end effector 400. As mentioned above, shaft assembly 200 is configured for selective connection to surgical instrument 100.

Figure 4:
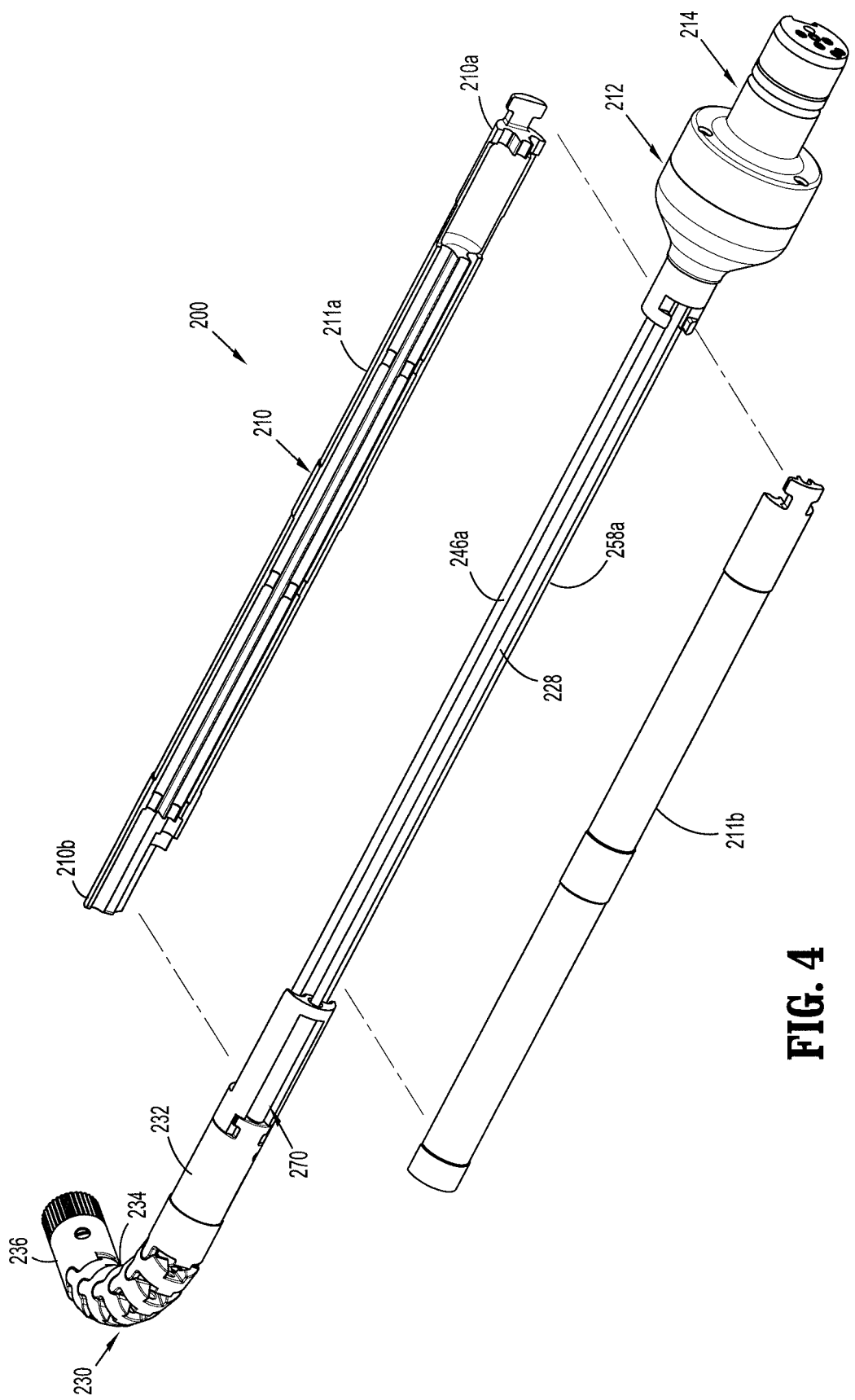
FIG. 4 is a perspective view, with parts separated, of the shaft assembly of FIGS. 1-3.

As seen in FIGS. 1, 2 and 4, shaft assembly 200 includes an elongate, substantially rigid, outer tubular body 210 having a proximal end 210a and a distal end 210b; a transmission housing 212 connected to proximal end 210a of tubular body 210 and being configured for selective connection to surgical instrument 100; and an articulating neck assembly 230 connected to distal end 210b of elongate body portion 210.

Transmission housing 212 is configured to house a pair of gear train systems therein for varying a speed/force of rotation (e.g., increase or decrease) of first, second and/or third rotatable drive members or connectors 118, 120, and/or 122 of surgical instrument 100 before transmission of such rotational speed/force to end effector 400.

Figure 5:
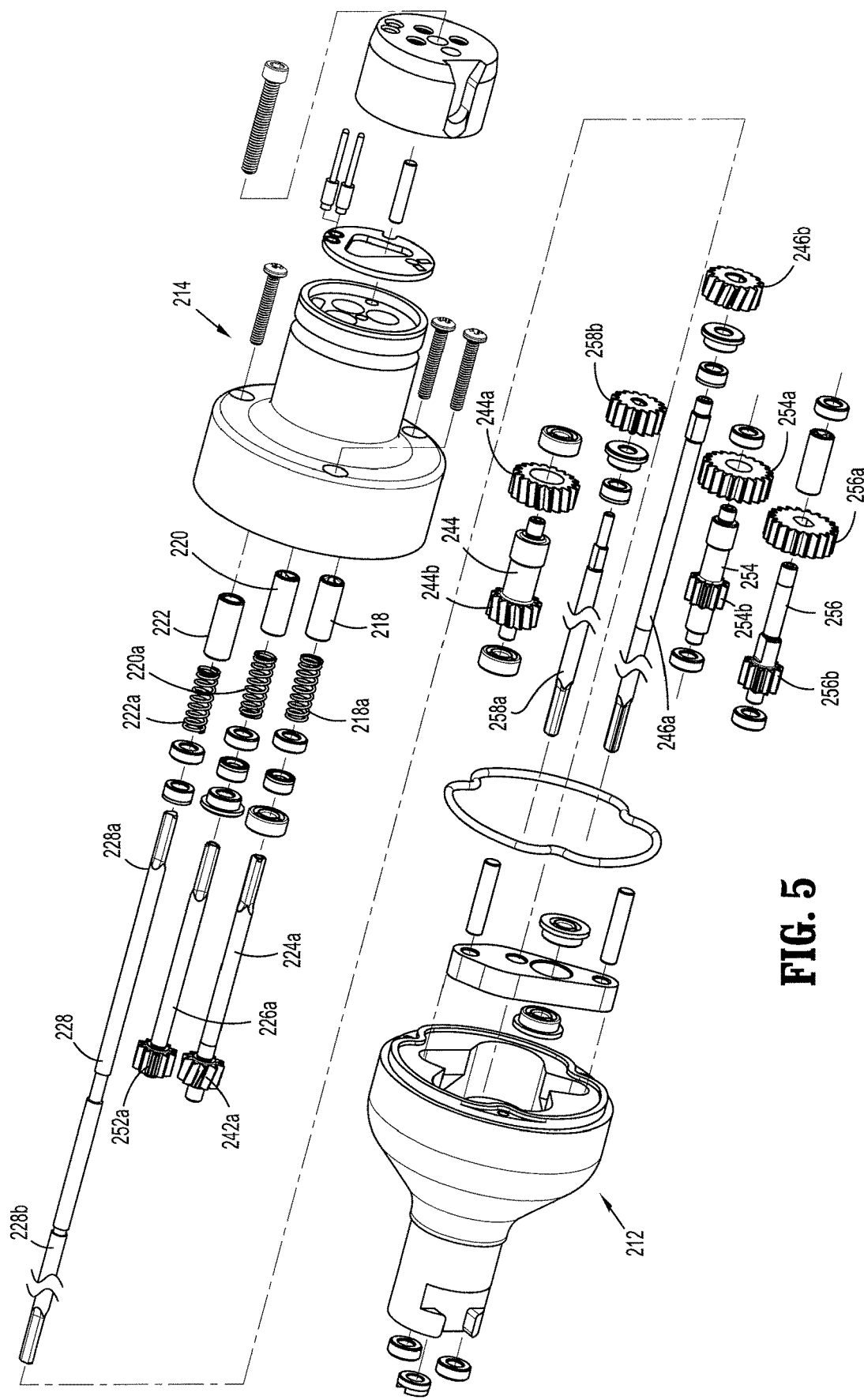
FIG. 5 is a perspective view, with parts separated of a transmission housing of the shaft assembly.

Transmission housing 212 of shaft assembly 200 is configured and adapted to connect to connecting portion 108a of upper housing portion 108 of surgical instrument 100. As seen in FIGS. 3-5, transmission housing 212 of shaft assembly 200 includes a shaft coupling assembly 214 supported at a proximal end thereof.

As seen in FIGS. 5 and 20-25, transmission housing 212 and shaft coupling assembly 214 rotatably support a first proximal or input drive shaft 224a, a second proximal or input drive shaft 226a, and a third drive shaft 228.

Shaft coupling assembly 214 is configured to rotatably support first, second and third connector sleeves 218, 220 and 222, respectively. Each of connector sleeves 218, 220, 222 is configured to mate with respective first, second and third drive members or connectors 118, 120, 122 of surgical instrument 100, as described above. Each of connector sleeves 218, 220, 222 is further configured to mate with a proximal end of respective first input drive shaft 224a, second input drive shaft 226a, and third drive shaft 228.

Shaft drive coupling assembly 214 includes a first, a second and a third biasing member 218a, 220a and 222a disposed distally of respective first, second and third connector sleeves 218, 220, 222. Each of biasing members 218a, 220a and 222a is disposed about respective first proximal drive shaft 224a, second proximal drive shaft 226a, and third drive shaft 228. Biasing members 218a, 220a and 222a act on respective connector sleeves 218, 220 and 222 to help maintain connector sleeves 218, 220 and 222 engaged with the distal end of respective drive rotatable drive members or connectors 118, 120, 122 of surgical instrument 100 when shaft assembly 200 is connected to surgical instrument 100.

In particular, first, second and third biasing members 218a, 220a and 222a function to bias respective connector sleeves 218, 220 and 222 in a proximal direction. In this manner, during connection of shaft assembly 200 to surgical instrument 100, if first, second and or third connector sleeves 218, 220 and/or 222 is/are misaligned with the drive members or connectors 118, 120, 122 of surgical instrument 100, first, second and/or third biasing member(s) 218a, 220a and/or 222a are compressed. Thus, when the drive mechanism of surgical instrument 100 is engaged, drive members or connectors 118, 120, 122 of surgical instrument 100 will rotate and first, second and/or third biasing member(s) 218a, 220a and/or 222a will cause respective first, second and/or third connector sleeve(s) 218, 220 and/or 222 to slide back proximally, effectively coupling drive members or connectors 118, 120, 122 of surgical instrument 100 to respective first input drive shaft 224a, second input drive shaft 226a, and third drive shaft 228.

In use, during a calibration of surgical instrument 100, each of drive connectors 118, 120, 122 of surgical instrument 100 is rotated and the bias on connector sleeve(s) 218, 220 and 222 properly seats connector sleeve(s) 218, 220 and 222 over the respective drive connectors 118, 120, 122 of surgical instrument 100 when the proper alignment is reached.

Shaft assembly 200 includes a first and a second gear train system 240, 250, respectively, disposed within transmission housing 212 and tubular body 210, and adjacent coupling assembly 214. As mentioned above, each gear train system 240, 250 is configured and adapted to vary a speed/force of rotation (e.g., increase or decrease) of first and second rotatable drive connectors 118 and 120 of surgical instrument 100 before transmission of such rotational speed/force to end effector 400.

Figure 6:
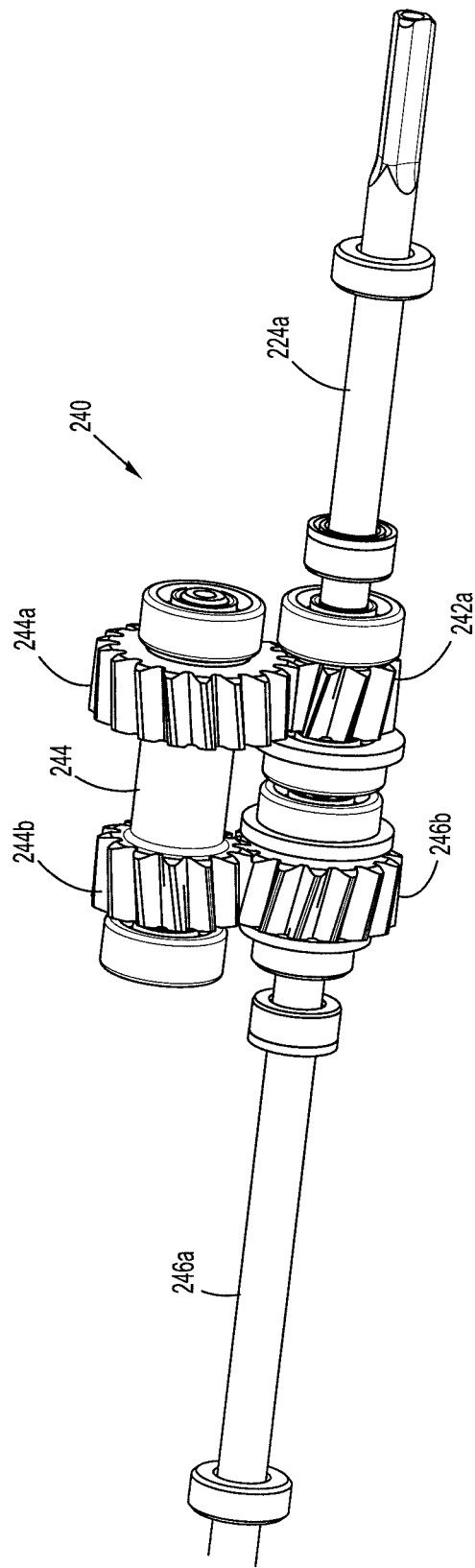
FIG. 6 is a perspective view of a first gear train system that is supported in the transmission housing.

As seen in FIGS. 5 and 6, first gear train system 240 includes first input drive shaft 224a, and a first input drive shaft spur gear 242a keyed to first input drive shaft 224a. First gear train system 240 also includes a first transmission shaft 244 rotatably supported in transmission housing 212, a first input transmission spur gear 244a keyed to first transmission shaft 244 and engaged with first input drive shaft spur gear 242a, and a first output transmission spur gear 244b keyed to first transmission shaft 244. First gear train system 240 further includes a first output drive shaft 246a rotatably supported in transmission housing 212 and tubular body 110, and a first output drive shaft spur gear 246b keyed to first output drive shaft 246a and engaged with first output transmission spur gear 244b.

In accordance with the present disclosure, first input drive shaft spur gear 242a includes 10 teeth; first input transmission spur gear 244a includes 18 teeth; first output transmission spur gear 244b includes 13 teeth; and first output drive shaft spur gear 246b includes 15 teeth. As so configured, an input rotation of first input drive shaft 224a is converted to an output rotation of first output drive shaft 246a by a ratio of 1:2.08.

As mentioned above, a proximal end of first input drive shaft 224a is configured to support first connector sleeve 218.

In operation, as first input drive shaft spur gear 242a is rotated, due to a rotation of first connector sleeve 258 and first input drive shaft 224a, as a result of the rotation of the first respective drive connector 118 of surgical instrument 100, first input drive shaft spur gear 242a engages first input transmission spur gear 244a causing first input transmission spur gear 244a to rotate. As first input transmission spur gear 244a rotates, first transmission shaft 244 is rotated and thus causes first output drive shaft spur gear 246b, that is keyed to first transmission shaft 244, to rotate. As first output drive shaft spur gear 246b rotates, since first output drive shaft spur gear 246b is engaged therewith, first output drive shaft spur gear 246b is also rotated. As first output drive shaft spur gear 246b rotates, since first output drive shaft spur gear 246b is keyed to first output drive shaft 246a, first output drive shaft 246a is rotated.

As will be discussed in greater detail below, shaft assembly 200, including first gear system 240, functions to transmit operative forces from surgical instrument 100 to end effector 400 in order to operate, actuate and/or fire end effector 400.

Figure 7:
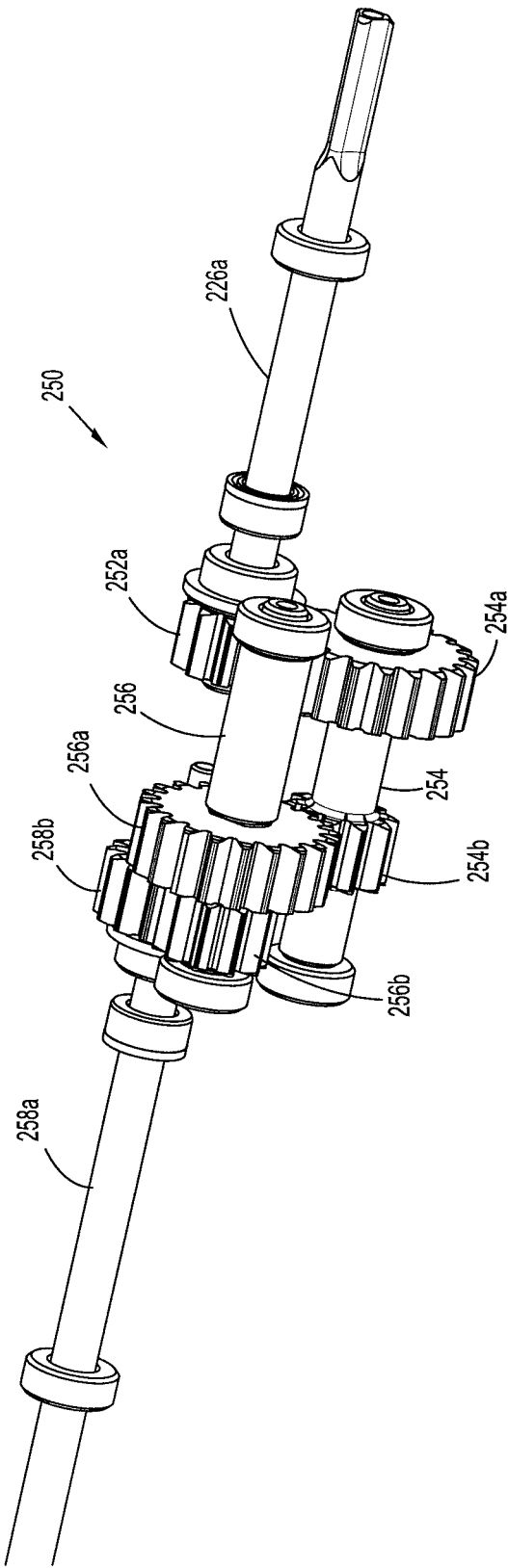
FIG. 7 is a perspective view of a second gear train system that is supported in the transmission housing.
Figure 8:
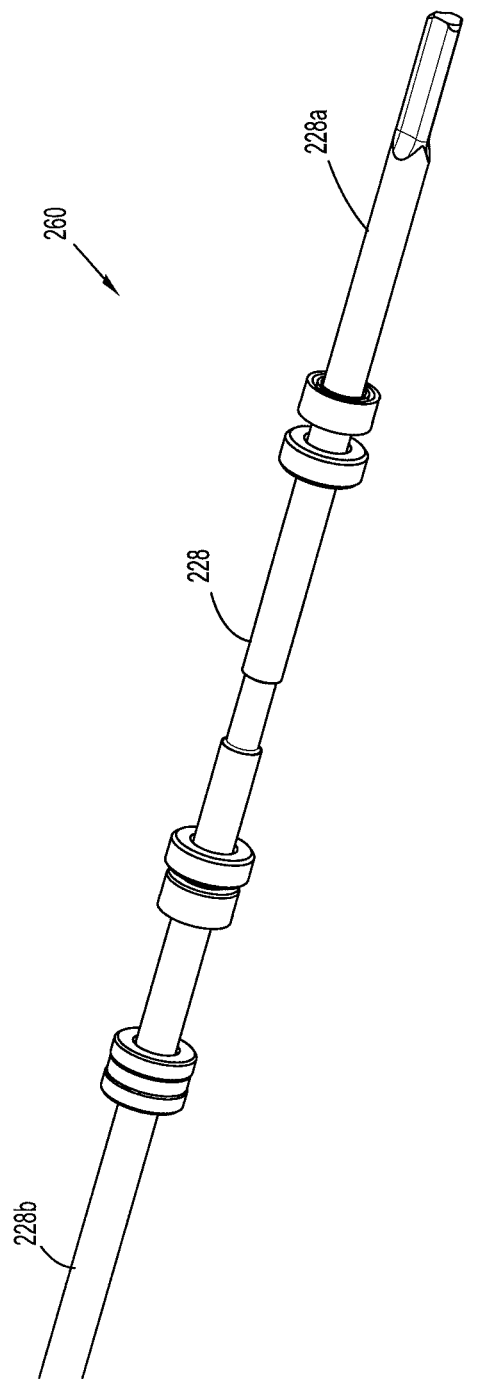
FIG. 8 is a perspective view of a third drive shaft that is supported in the transmission housing.
Figure 11:
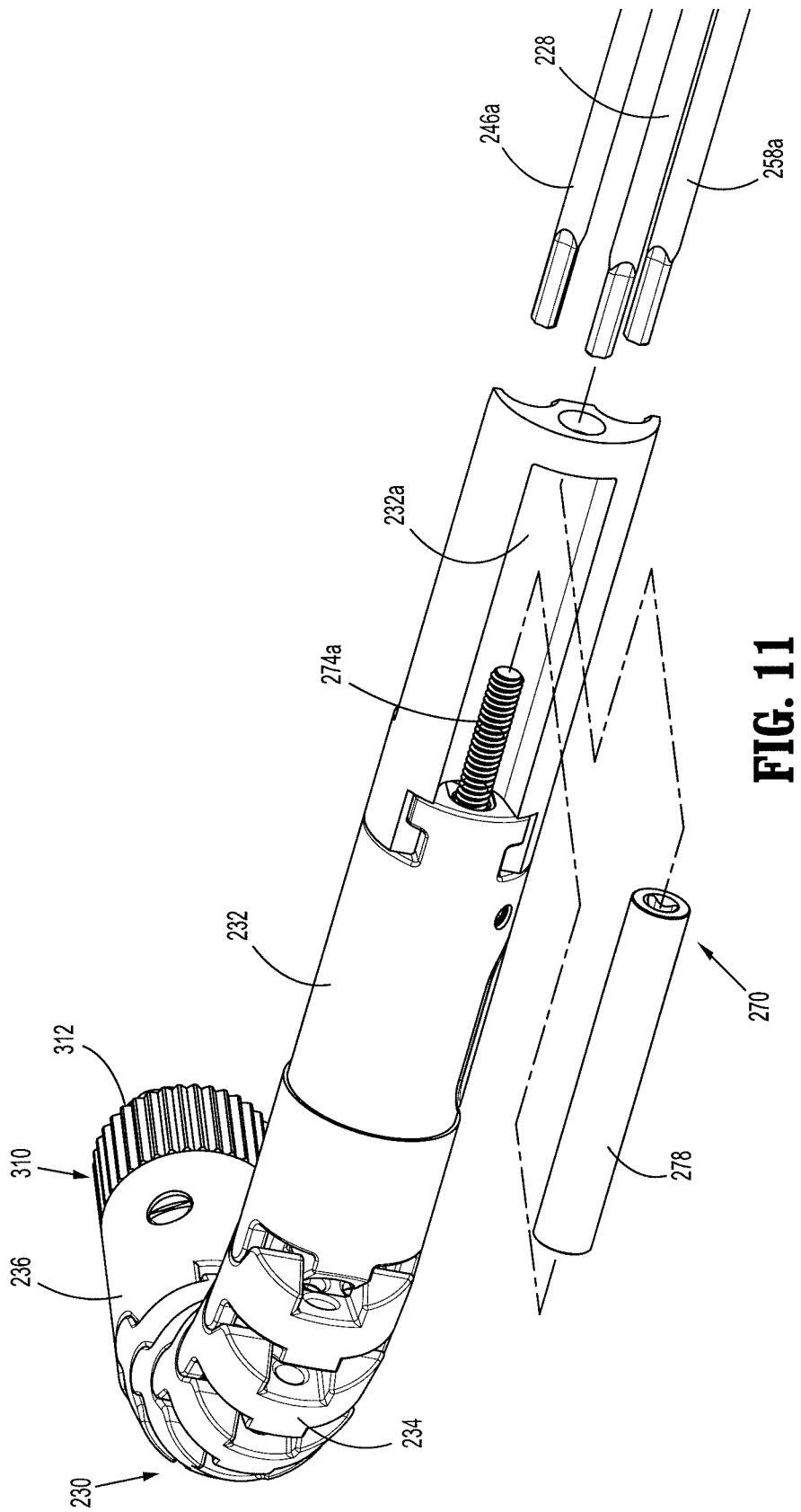
FIG. 11 is a perspective view of the neck assembly of FIGS. 9 and 10, with a threaded nut separated therefrom.

As seen in FIGS. 5 and 7, second gear train system 250 includes second input drive shaft 226a, and a second input drive shaft spur gear 252a keyed to second input drive shaft 226a. Second gear train system 250 also includes a first transmission shaft 254 rotatably supported in transmission housing 212, a first input transmission spur gear 254a keyed to first transmission shaft 254 and engaged with second input drive shaft spur gear 252a, and a first output transmission spur gear 254b keyed to first transmission shaft 254.

Second gear train system 250 further includes a second transmission shaft 256 rotatably supported in transmission housing 212, a second input transmission spur gear 256a keyed to second transmission shaft 256 and engaged with first output transmission spur gear 254b that is keyed to first transmission shaft 254, and a second output transmission spur gear 256b keyed to second transmission shaft 256.

Second gear train system 250 additionally includes a second output drive shaft 258a rotatably supported in transmission housing 212 and tubular body 210, and a second output drive shaft spur gear 258b keyed to second output drive shaft 258a and engaged with second output transmission spur gear 256b.

In accordance with the present disclosure, second input drive shaft spur gear 252a includes 10 teeth; first input transmission spur gear 254a includes 20 teeth; first output transmission spur gear 254b includes 10 teeth; second input transmission spur gear 256a includes 20 teeth; second output transmission spur gear 256b includes 10 teeth; and second output drive shaft spur gear 258b includes 15 teeth. As so configured, an input rotation of second input drive shaft 226a is converted to an output rotation of second output drive shaft 258a by a ratio of 1:6.

As mentioned above, a proximal end of second input drive shaft 226a is configured to support second connector sleeve 220.

In operation, as second input drive shaft spur gear 252a is rotated, due to a rotation of second connector sleeve 260 and second input drive shaft 226a, as a result of the rotation of the second respective drive connector 120 of surgical instrument 100, second input drive shaft spur gear 252a engages first input transmission spur gear 254a causing first input transmission spur gear 254a to rotate. As first input transmission spur gear 254a rotates, first transmission shaft 254 is rotated and thus causes first output transmission spur gear 254b, that is keyed to first transmission shaft 254, to rotate. As first output transmission spur gear 254b rotates, since second input transmission spur gear 256a is engaged therewith, second input transmission spur gear 256a is also rotated. As second input transmission spur gear 256a rotates, second transmission shaft 256 is rotated and thus causes second output transmission spur gear 256b, that is keyed to second transmission shaft 256, to rotate. As second output transmission spur gear 256b rotates, since second output drive shaft spur gear 258b is engaged therewith, second output drive shaft spur gear 258b is rotated. As second output drive shaft spur gear 258b rotates, since second output drive shaft spur gear 258b is keyed to second output drive shaft 258a, second output drive shaft 258a is rotated.

As will be discussed in greater detail below, shaft assembly 200, including second gear train system 250, functions to transmit operative forces from surgical instrument 100 to end effector 400 in order rotate shaft assembly 200 and/or end effector 400 relative to surgical instrument 100.

As mentioned above and as seen in FIGS. 5 and 8, transmission housing 212 and shaft coupling assembly 214 rotatably support a third drive shaft 228. Third drive shaft 228 includes a proximal end 228a configured to support third connector sleeve 222, and a distal end 228b extending to and operatively connected to an articulation assembly 270 as will be discussed in greater detail below.

As seen in FIG. 4, elongate, outer tubular body 210 of shaft assembly 200 includes a first half section 211a and a second half section 211b defining at least three longitudinally extending channels through outer tubular body 210 when half sections 211a, 211b are mated with one another. The channels are configured and dimensioned to rotatably receive and support first output drive shaft 246a, second output drive shaft 258a, and third drive shaft 228 as first output drive shaft 246a, second output drive shaft 258a, and third drive shaft 228 extend from transmission housing 212 to articulating neck assembly 230. Each of first output drive shaft 246a, second output drive shaft 258a, and third drive shaft 228 are elongate and sufficiently rigid to transmit rotational forces from transmission housing 220 to articulating neck assembly 230.

Turning now to FIGS. 4 and 9-16, articulating neck assembly 230 is shown and described. Articulating neck assembly 230 includes a proximal neck housing 232, a plurality of links 234 connected to and extending in series from proximal neck housing 232; and a distal neck housing 236 connected to and extending from a distal-most link of the plurality of links 234. It is contemplated that, in any of the embodiments disclosed herein, that the shaft assembly may have a single link or pivot member for allowing the articulation of the end effector. It is contemplated that, in any of the embodiments disclosed herein, that the distal neck housing can be incorporated with the distal most link.

Each link 234 includes cooperating knuckles and clevises formed on each of a proximal surface 234a and a distal surface 234b thereof. Proximal neck housing 232 includes knuckles and/or clevises that operatively engage with the knuckles and/or clevises of a proximal-most link. Distal neck housing 236 includes knuckles and/or clevises that operatively engage with the knuckles and/or clevises of a distal-most link. The knuckles and clevises of adjacent neck housings 232, 236 and links 234 operatively engage with one another to define a direction and a degree of articulation of neck assembly 230.

Neck assembly 230 is configured to enable end effector 400 to move between a substantially linear configuration and a substantially angled, off-axis or articulated configuration. In accordance with the present disclosure, it is contemplated that neck assembly 230 is capable of articulating in a single plane and is capable of articulating approximately 90°, and even greater than 90°.

Figure 12:
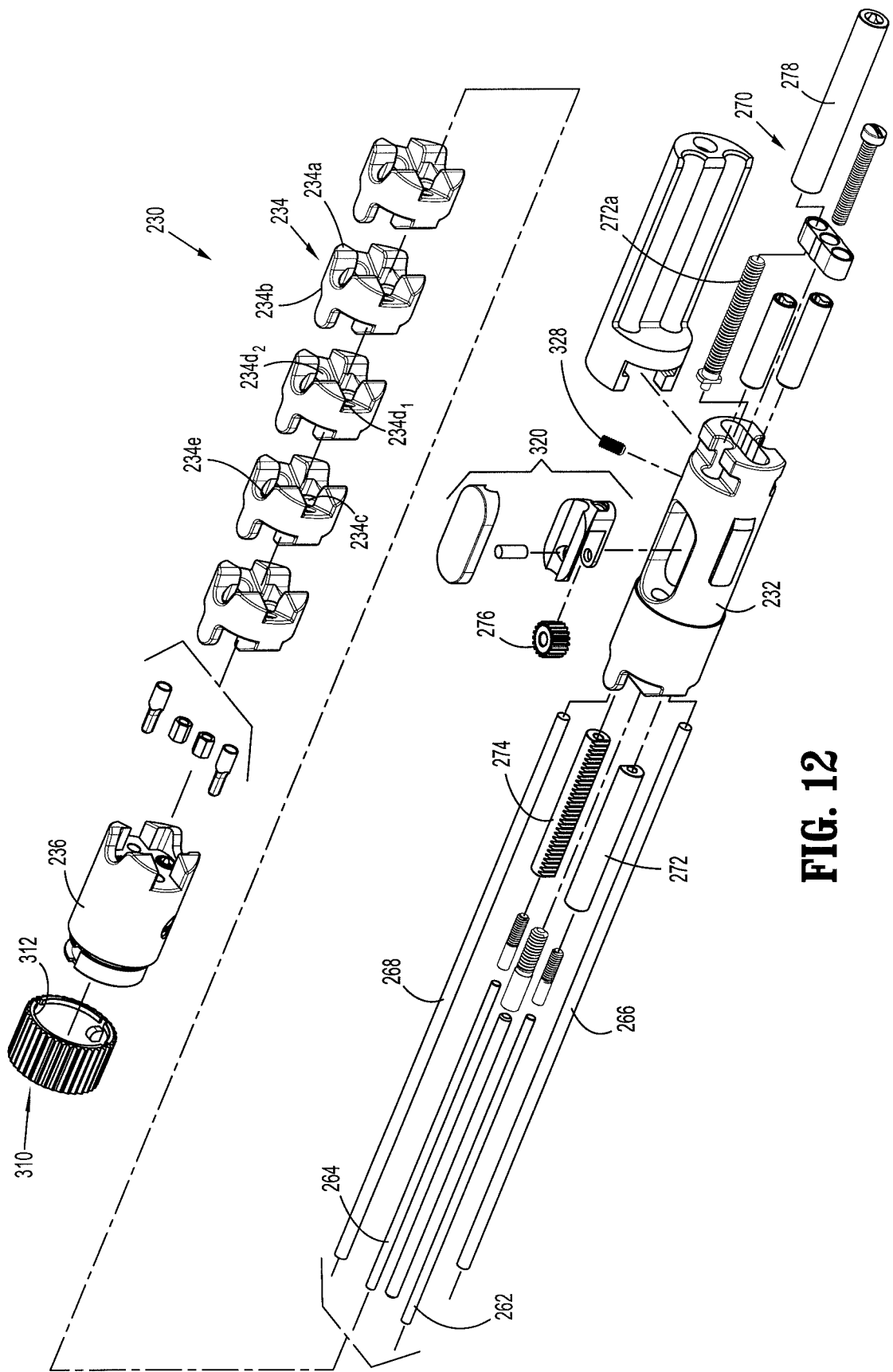
FIG. 12 is a perspective view, with parts separated, of the neck assembly of FIGS. 9-11.

Each link 234 defines a first lumen 234c (see FIG. 12) therein for passage of a first drive cable or member 266 therethrough; a first pair of opposed lumens $234d_1$, $234d_2$, for passage of a pair of articulation cables 262, 264 therethrough; and a second lumen 234e for passage of a second drive cable or member 268 therethrough. As seen in FIG. 12, first and second lumens 234c, 234e are diametrically opposed to one another and offset 90° relative to lumens $234d_1$, $234d_2$. Each of first drive cable or member 266 and second drive cable or member 268 includes a proximal end keyed to a distal end of respective first output drive shaft 246a and second output drive shaft 258a. Each of first and second drive cables 266, 268 is fabricated from a material that is both flexible and torsionally stiff (capable of transmitting rotational forces or torque), such as, for example, stainless steel and the like.

As seen in FIGS. 13-16, proximal neck housing 232 of neck assembly 230 supports an articulation assembly 270 configured and adapted to impart articulation to neck assembly 230 and/or end effector 400. Articulation assembly 270 includes a pair of opposed gear racks 272, 274 engaged with and on opposed sides of a pinion gear 276. Racks 272, 274 are axially slidably supported in proximal neck housing 232 and pinion gear 276 is rotatably supported in proximal neck housing 232.

Figure 13:
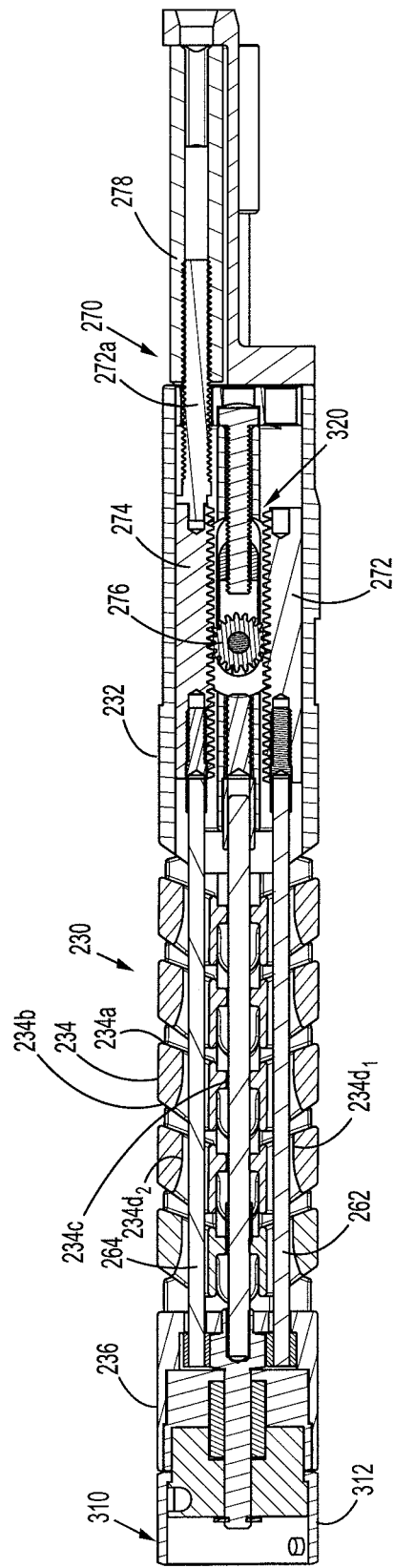
FIG. 13 is a cross-sectional view of the neck assembly of FIGS. 9-12, as taken through 13-13 of FIG. 9.
Figure 17:
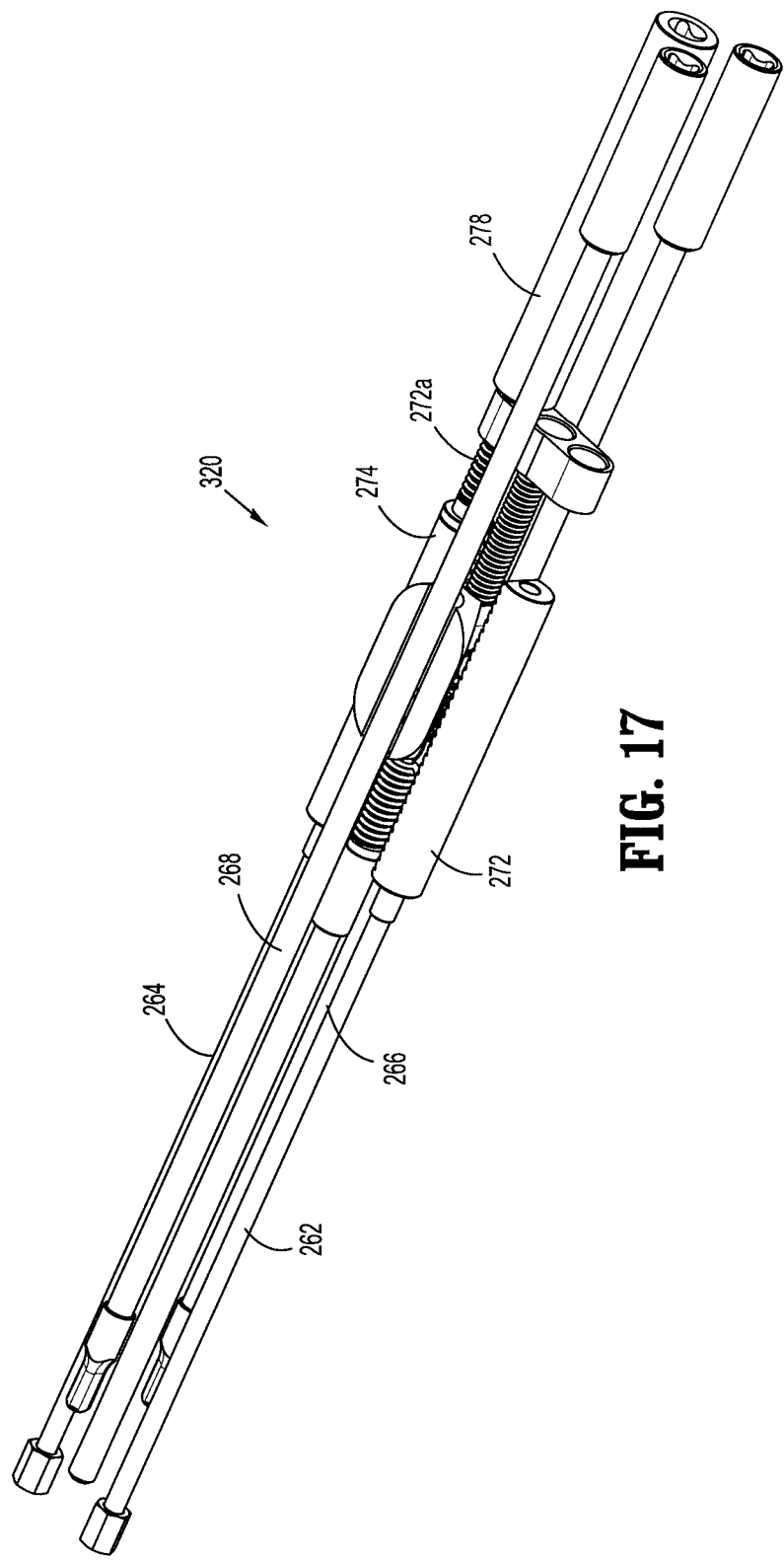
FIG. 17 is a perspective view of an articulation assembly.
Figure 18:
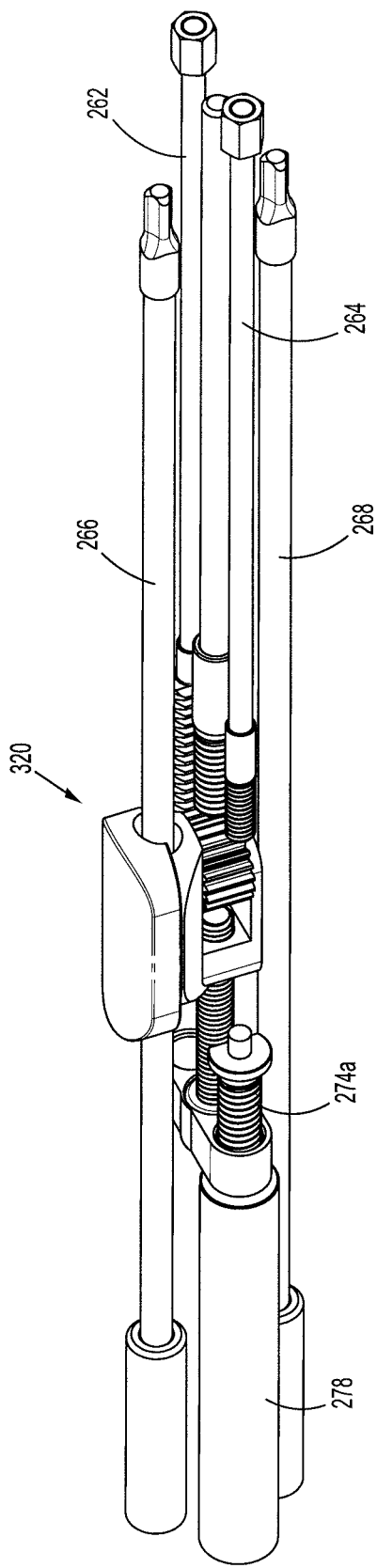
FIG. 18 is a further perspective view of the articulation assembly of FIG. 17.
Figure 19:
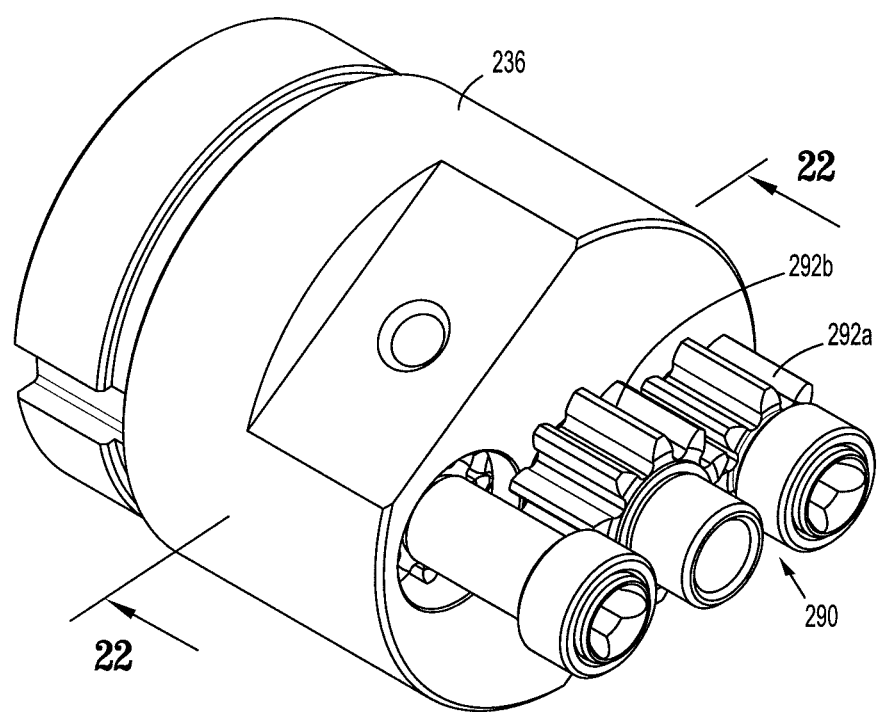
FIG. 19 is a perspective view of a second gear train that is supported in a distal neck housing of the neck assembly.
Figure 20:
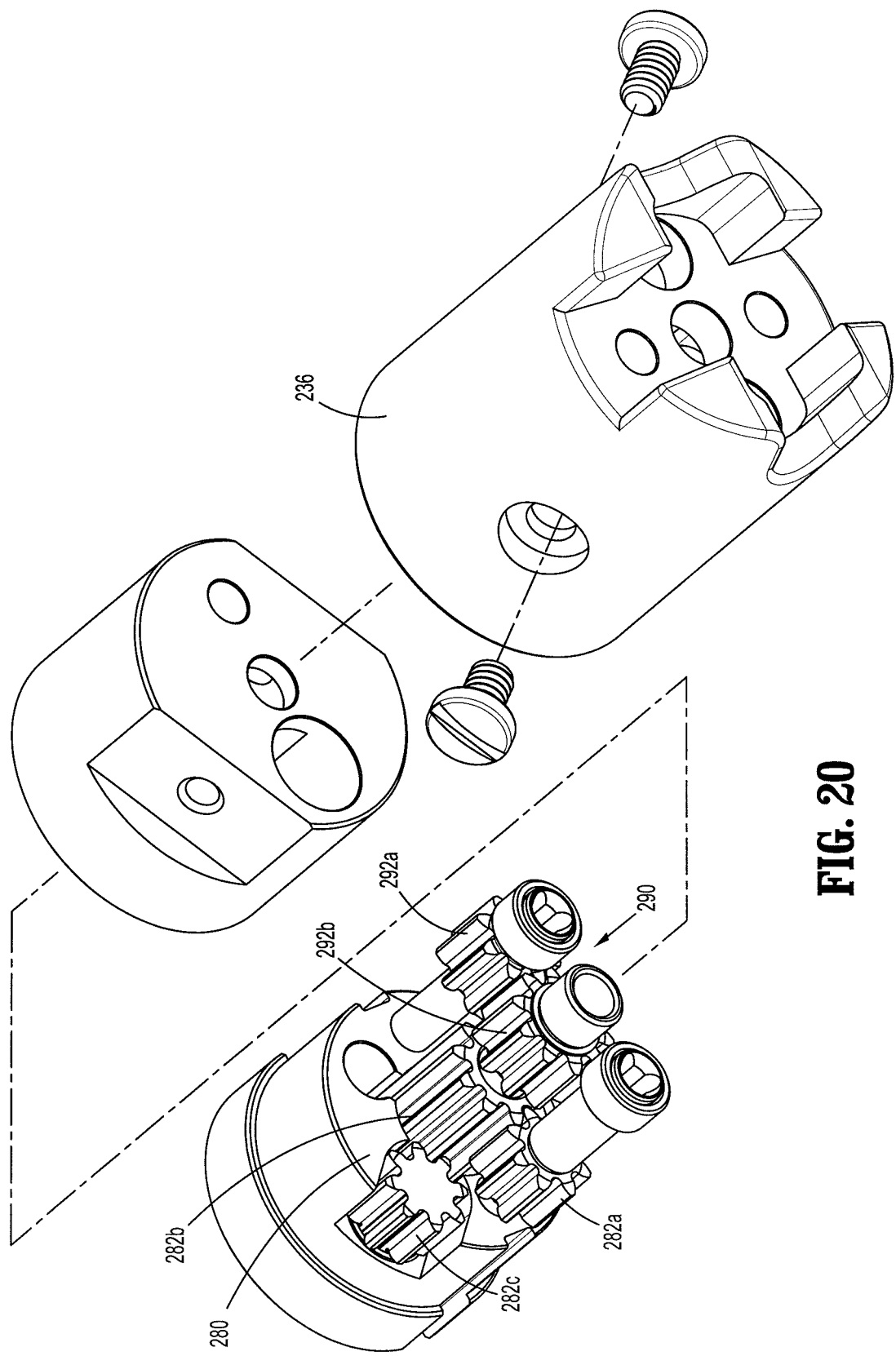
FIG. 20 is a perspective view, with parts partially separated, of a first gear train and the second gear train that are supported in a distal neck housing of the neck assembly.
Figure 21:
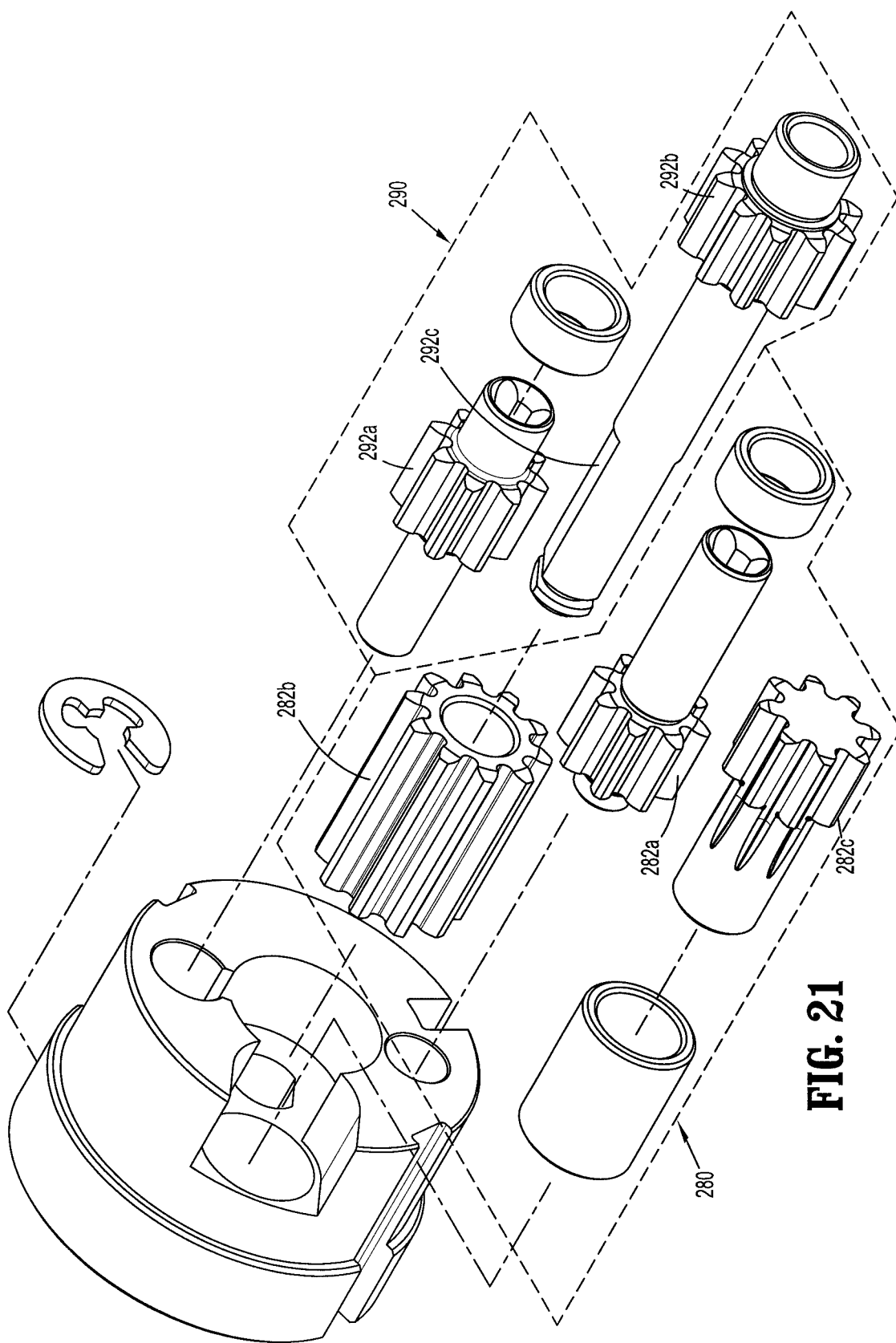
FIG. 21 is a perspective view, with parts partially separated, of the first gear train and the second gear train that are supported in a distal neck housing of the neck assembly.
Figure 24:
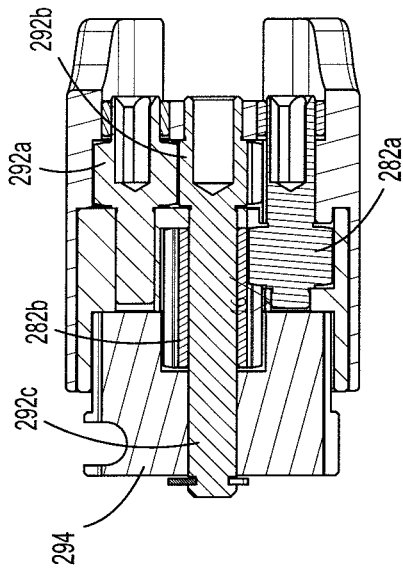
FIG. 24 is a cross-sectional view of the distal neck housing, as taken through 24-24 of FIG. 22.
Figure 25:
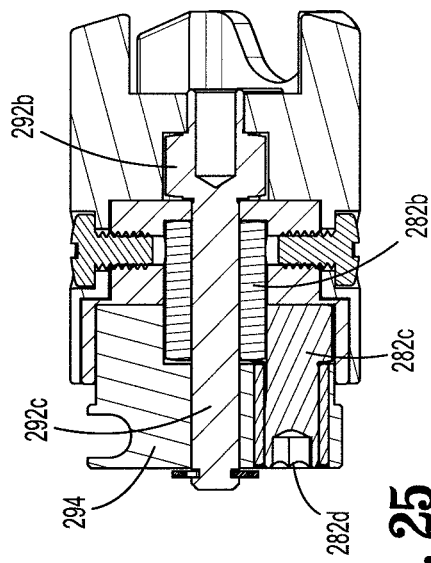
FIG. 25 is a cross-sectional view of the distal neck housing, as taken through 25-25 of FIG. 22.
Figure 23:
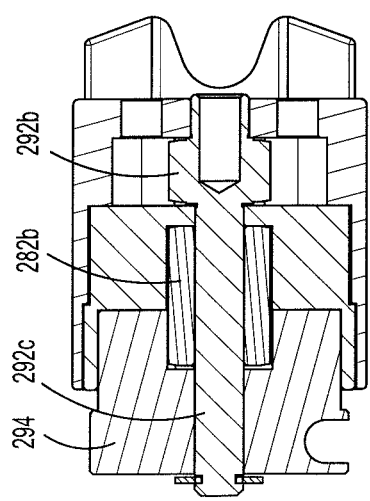
FIG. 23 is a cross-sectional view of the distal neck housing, as taken through 23-23 of FIG. 22.
Figure 22:
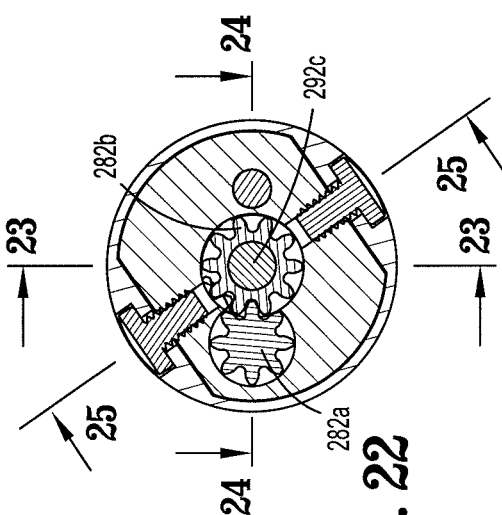
FIG. 22 is a cross-sectional view of the distal neck housing, as taken through 22-22 of FIG. 19.

As seen in FIGS. 12, 13 and 17, rack 274 is attached to a threaded shaft 272a extending proximally therefrom and that is in threaded engagement with a distal end of an internally threaded nut 278. Threaded nut 278 is rotatably supported and axially fixed within a pocket 232a formed in proximal neck housing 232. A proximal end of threaded nut 278 is keyed to a distal end of third drive shaft 228. While threaded shaft 272a is shown extending from rack 274, it is understood, and within the scope of the present disclosure, that the threaded shaft may extend from rack 272 without departing from the principles of the present disclosure.

Articulation cables 262, 264 include proximal ends that are secured to and extend from a respective distal end of racks 272, 274. Each articulation cable 262, 264 includes a distal end that extends through respective opposed lumens $234d_1$, $234d_2$ of links 234 and that is secured to or anchored in distal neck housing 234 or the distal most link.

Figure 16:
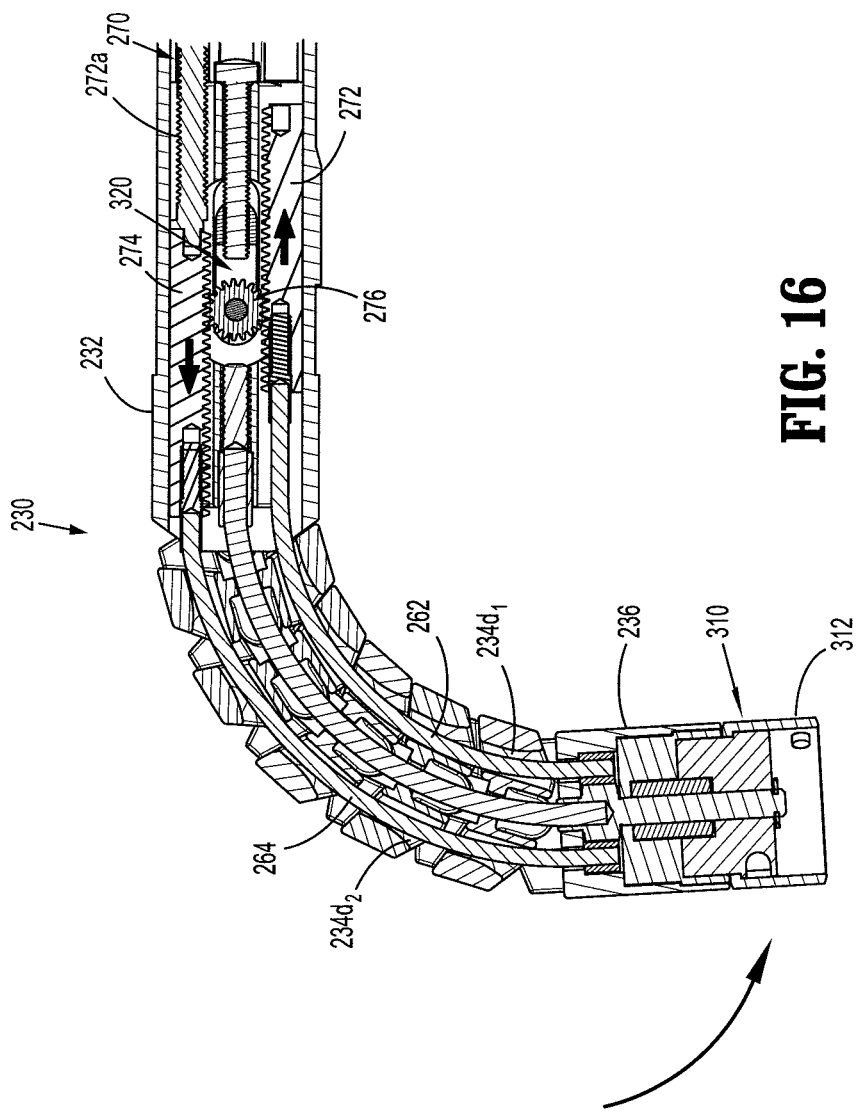
FIG. 16 is an illustration of the neck assembly of FIG. 13, shown in an articulated condition.

In operation, to articulate neck assembly 230 in a first direction, third drive shaft 228 is rotated in a first direction, as described above, to rotate threaded nut 278 and axially displace threaded shaft 272a distally to axially displace rack 274 distally (see FIG. 16). As rack 274 is displaced axially, in a distal direction, rack 274 causes pinion gear 276 to be rotated and to thus act on rack 272, to axially displace rack 272 in a proximal direction. As rack 272 is axially displaced in a proximal direction, rack 272 causes articulation cable 262 to be drawn in a proximal direction and thereby articulate neck assembly 230, as illustrated in FIG. 16. Neck assembly 230 is permitted to articulate since axially displacement of rack 274, in a distal direction, results in axial, distal displacement of articulation cable 264.

Distal neck housing 236 supports a first gear train 280 and a second gear train 290. First gear train 280 functions to transmit a rotation of first drive cable or member 266 to end effector 400. Second gear train 290 functions to transmit a rotation of second drive cable or member 268 to end effector 400.

As seen in FIGS. 20-25, first gear train 280 of distal neck housing 236 includes a first spur gear 282a rotatably supported in distal neck housing 236 and keyed to a distal end of first drive cable 266 of shaft assembly 200. First gear train 280 of distal neck housing 236 further includes a second spur gear 282b rotatably supported in distal neck housing 236 and engaged with first spur gear 282a. First gear train 280 of distal neck housing 236 also includes a third spur gear 282c rotatably supported in distal neck housing 236 and engaged with second spur gear 282b.

Figure 26:
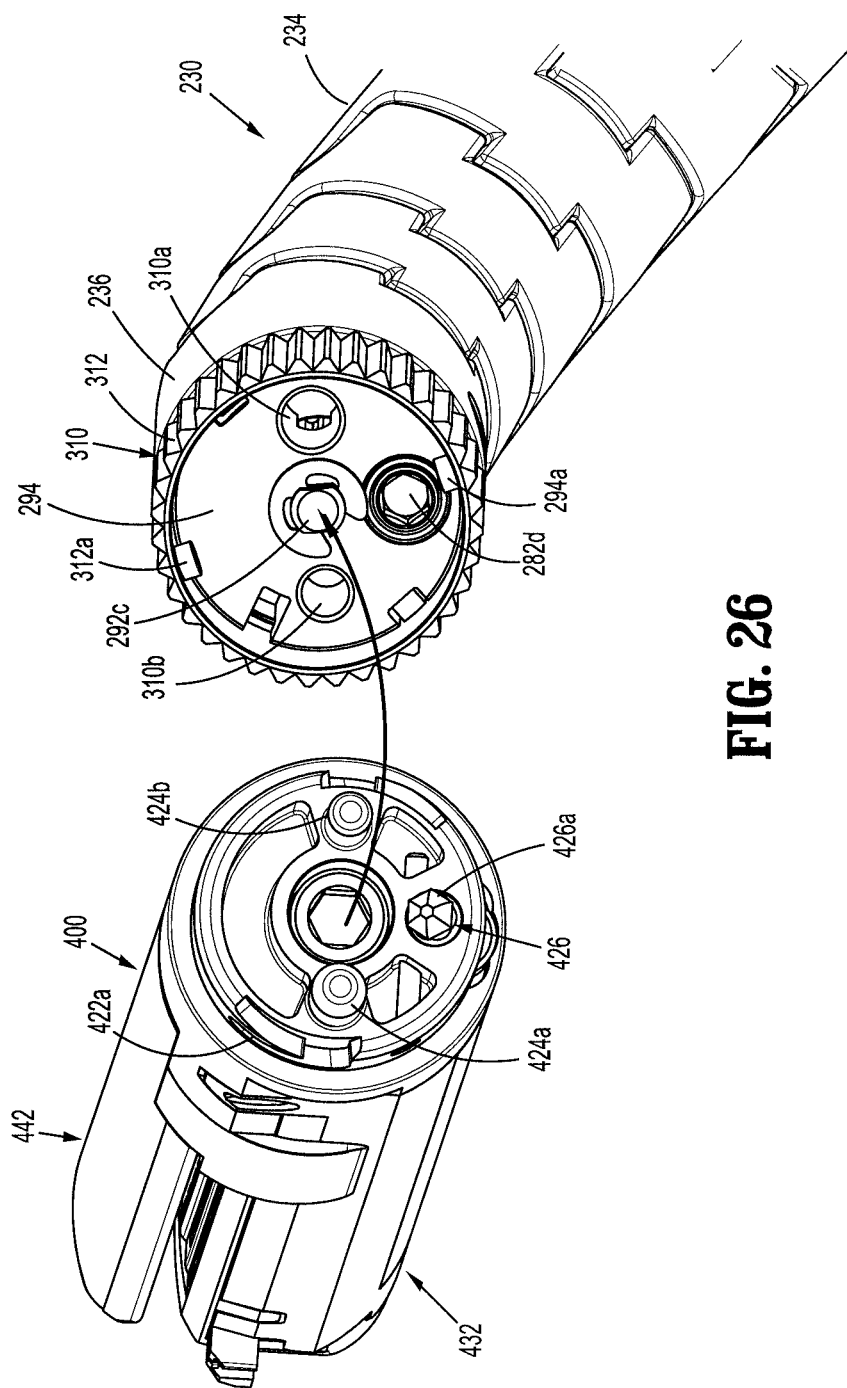
FIG. 26 is a rear, perspective view of the shaft assembly and an end effector, of the electromechanical surgical system of FIGS. 1 and 2, illustrating a connection therebetween.

Third spur gear 282c includes a bore 282d formed along a central axis thereof that is configured for mating receipt of a drive axle 426 of end effector 400 (see FIG. 26).

In accordance with the present disclosure, first spur gear 282a includes 8 teeth; second spur gear 282b includes 10 teeth; and third spur gear 282c includes 8 teeth. As so configured, an input rotation of first drive cable 266 is converted to an output rotation of third spur gear 282c of distal neck housing 236 by a ratio of 1:1. Additionally, first gear train 280 is provided to rotatably and mechanically connect first drive cable 266 to drive axle 426 of end effector 400.

In operation, as first drive cable 266 is rotated, due to a rotation of first output drive shaft 246a (as described above), said rotation is transmitted to first spur gear 282a of first gear train 280. As first spur gear 282a is rotated, third spur gear 282c is rotated due to the inter-engagement of first spur gear 282a and third spur gear 282c by second spur gear 282b. As third spur gear 282c is rotated, when end effector 400 is connected to shaft assembly 200, and specifically, third spur gear 282c is connected to drive axle 426 of end effector 400, a rotation of third spur gear 282c results in rotation of drive axle 426 of end effector 400 and actuation of end effector 400.

As seen in FIGS. 20-25, second gear train 290 of distal neck housing 236 includes a first spur gear 292a rotatably supported in distal neck housing 236 and keyed to a distal end of second drive cable 268 of shaft assembly 200. Second gear train 290 of distal neck housing 236 further includes a second spur gear 292b rotatably supported in distal neck housing 236 and engaged with first spur gear 292a. Second gear train 290 of distal neck housing 236 also includes a non-circular shaft 292c extending from second spur gear 292b (see FIG. 21). Non-circular shaft 292c is keyed to a rotation hub 294 such that rotation of non-circular shaft 292c results in rotation of rotation hub 294.

Rotation hub 294 is provided between a shaft of third spur gear 282c, of first gear train 280, that defines the bore 282d thereof and rotation hub 294 transmitting relative rotation of third spur gear 282c of first gear train 280 to rotation hub 294 of second gear train 290.

In accordance with the present disclosure, first spur gear 292a includes 8 teeth (which functions as the input); and second spur gear 292b includes 10 teeth. As so configured, an input rotation of second drive cable 268 is converted to an output rotation of rotation hub 294. The gear ratio for this is 1:0.8. Additionally, second gear train 290 is provided to rotatably and mechanically connect second drive cable 268 to rotation hub 294 of distal neck housing 236 of neck assembly 230.

In operation, as second drive cable 268 of shaft assembly 200 is rotated, due to a rotation of second output drive shaft 258a (as described above), said rotation is transmitted to first spur gear 292a of first gear train 290. As first spur gear 292a is rotated, non-circular shaft 292c is rotated due to its connection with second spur gear 292b. As non-circular shaft 292c is rotated, when end effector 400 is connected to shaft assembly 200, and specifically, rotation hub 294 is connected to alignment stems 424a, 424b of end effector 400, a rotation of rotation hub 294 results in rotation of end effector 400.

Shaft assembly 200 further includes an end effector coupling assembly 310 supported at a distal end of distal neck housing 236 of articulating neck assembly 230. End effector coupling assembly 310 includes a collar 312 rotatably supported on and extending distally from distal neck housing 236 and being biased to a first radial portion. Collar 312 is rotatable from a first radial position to a second radial position, wherein end effector 400 is matable to end effector coupling assembly 310, and returns, by way of the bias, to the first radial position, to lock end effector 400 to shaft assembly 200.

It is contemplated that collar 312 includes at least one nub 312a extending radially inward from inner surface thereof for receipt in a respective complementary structure 422a formed in an outer surface of end effector 400 to connect end effector 400 to shaft assembly 200 in the manner of a bayonet-type connection. Other forms of connection are contemplated, such as, detents, threaded connections, etc.

As seen in FIGS. 12-14, 17 and 18, shaft assembly 200 includes a cable tensioning assembly 320. Cable tensioning assembly 320 includes a clevis 322 slidably supported in proximal neck housing 232, for axial displacement therewithin. Clevis 322 rotatably supports pinion gear 276 of articulation assembly 270. Cable tensioning assembly 320 includes an adjustment screw 324, rotatably supported in proximal neck housing 232 and retained against axial displacement. Adjustment screw 324 is threadably connected to clevis 322 such that rotation of adjustment screw 324 results in axial displacement of clevis 322.

In operation, during an assembly of shaft assembly 200, an operator rotates adjustment screw 324 in a direction so as to axially displace clevis 322 in a proximal direction. As clevis 322 is axially displaced, in a proximal direction, clevis 322 pulls on pinion gear 276 of articulation assembly 270. As pinion gear 276 is axially displaced, in a proximal direction, pinion gear 276 acts on racks 272, 274 to draw racks 272, 274 in a proximal direction. As racks 272, 274 are drawn in a proximal direction, with articulation cables 262, 264 respectively connected thereto, and with distal ends of articulation cables 262, 264 fixed or anchored in place, articulation cables 262, 264 are caused to be tensioned. It is contemplated that a set screw 328 (see FIG. 12) may be provided to fix the position of adjustment screw 324 and help to maintain articulation cables 262, 264 tensioned.

It is contemplated that over time and/or following a number of uses, that an end user of shaft assembly 200 may be able to access adjustment screw 324 and re-tension articulation cables 262, 264 as needed or necessary.

Turning now to FIGS. 26-49, end effector 400 is shown and described. End effector 400 is configured and adapted to apply a plurality of linear rows of fasteners 433. In certain embodiments, the fasteners are of various sizes, and, in certain embodiments, the fasteners have various lengths or rows, e.g., about 30, 45 and 60 mm in length.

Figure 27:
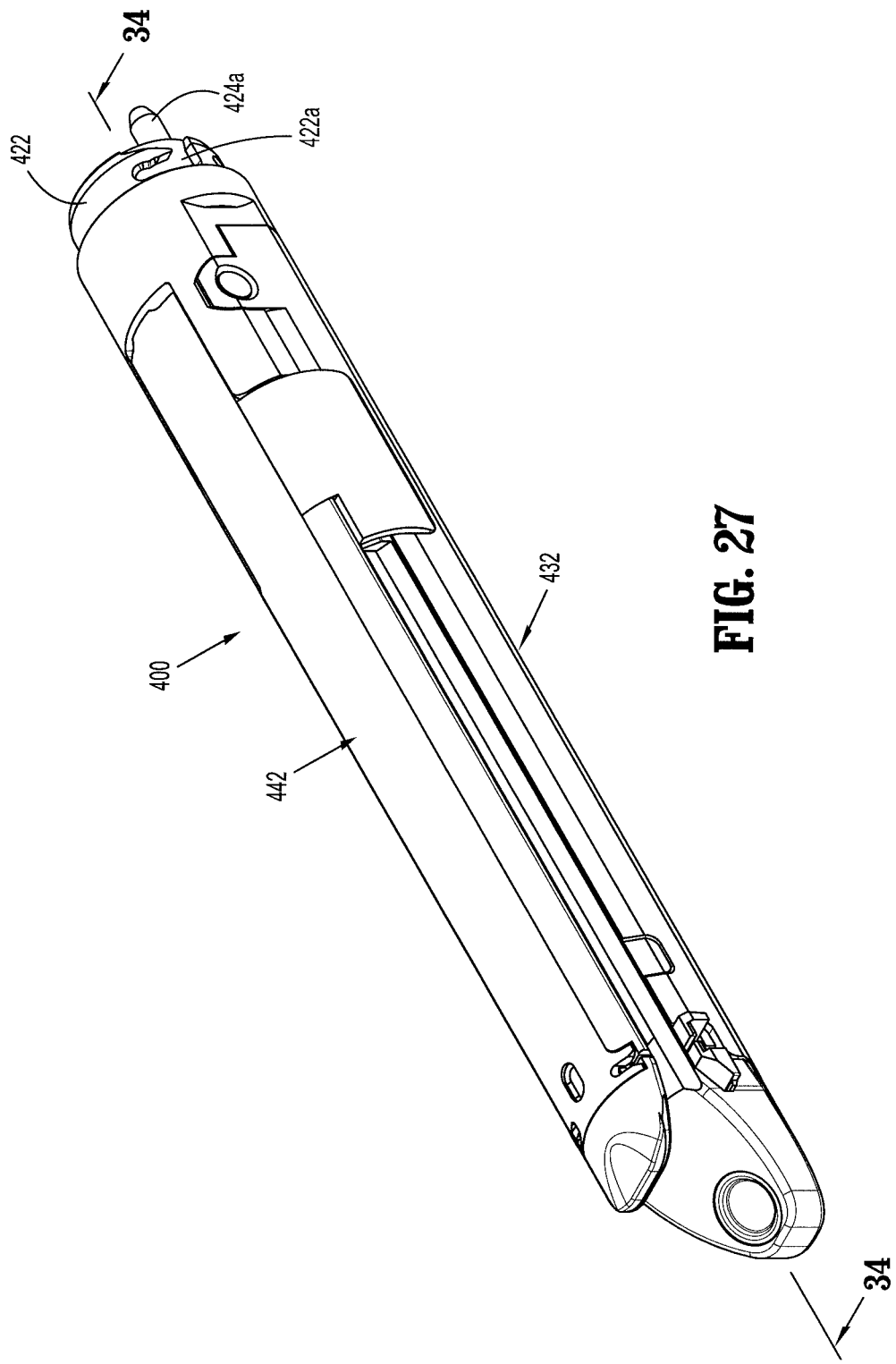
FIG. 27 is a perspective view of the end effector, shown in a closed condition.
Figure 28:
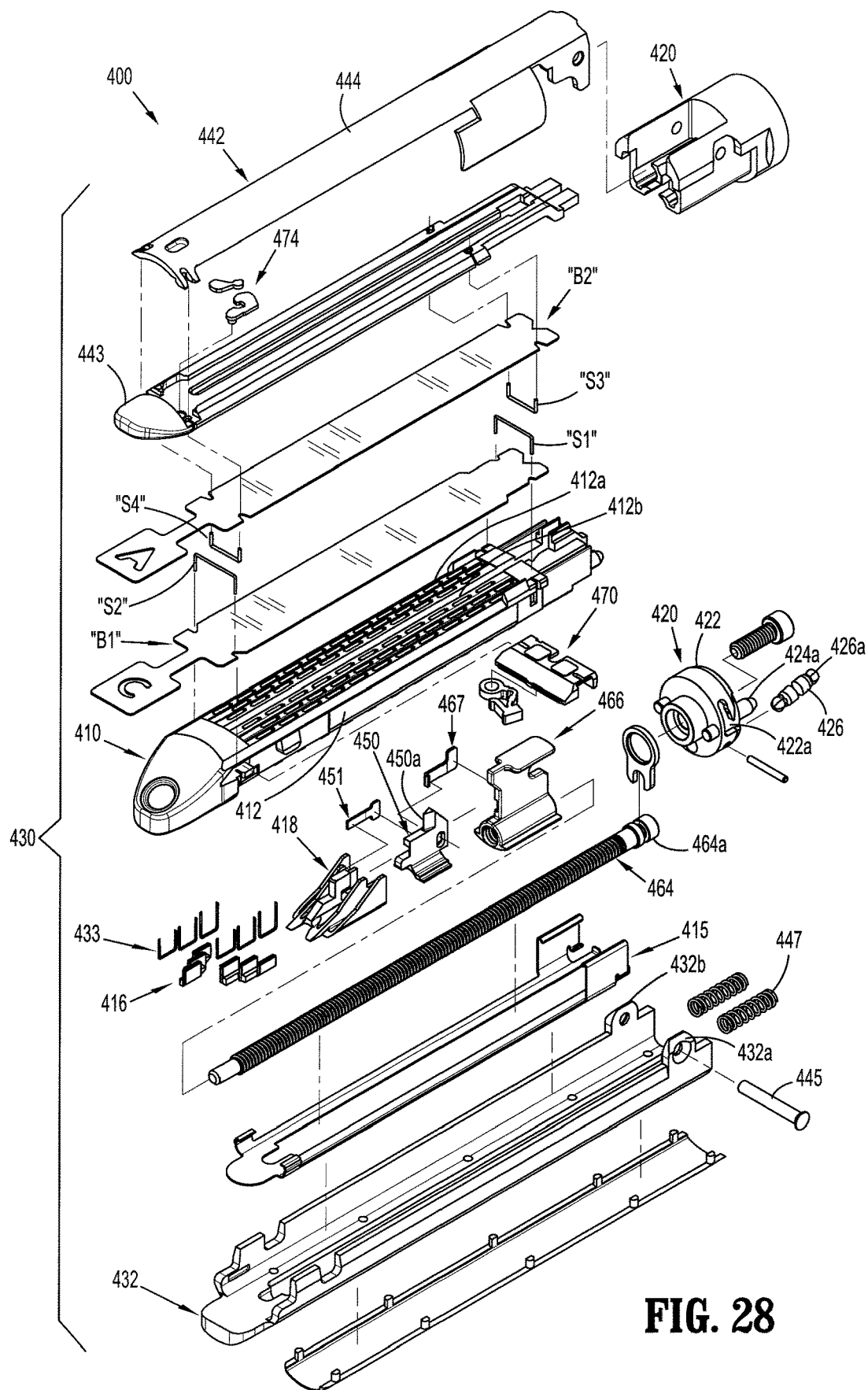
FIG. 28 is a perspective view, with parts separated, of the end effector of FIG. 27.
Figure 29:
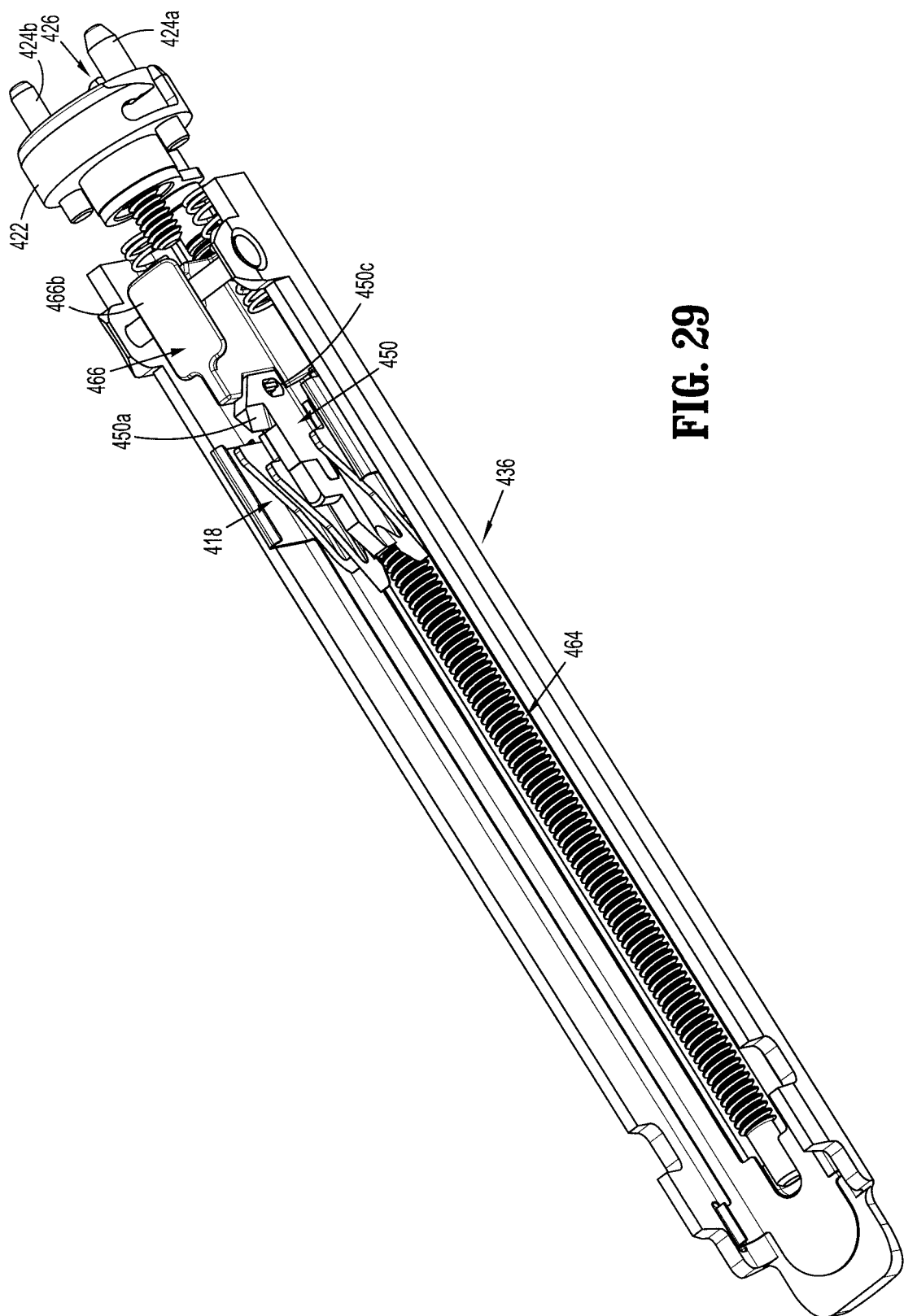
FIG. 29 is a perspective view of a lower jaw of the end effector of FIGS. 27 and 28.
Figure 30:
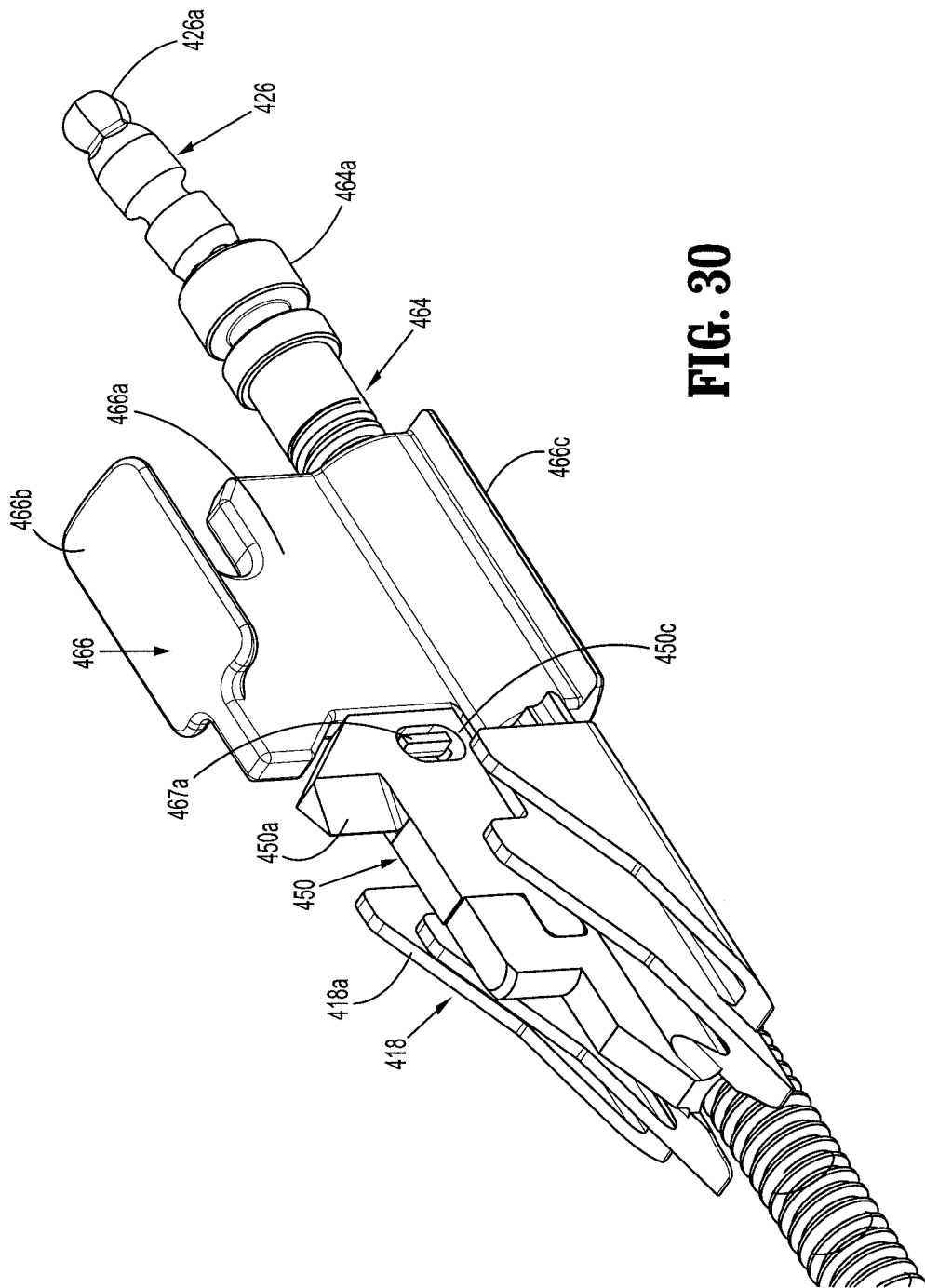
FIG. 30 is a perspective view of a drive beam, a knife sled and an actuation sled of the end effector of FIGS. 27-29.

As seen in FIGS. 26-28, end effector 400 includes a mounting portion 420 (FIG. 28) configured for selective connection to end effector coupling assembly 310 of shaft assembly 200. End effector 400 further includes a jaw assembly 430 connected to and extending distally from mounting portion 420. Jaw assembly 430, as will be discussed in greater detail below, includes a lower jaw 432 pivotally connected to mounting portion 420 and being configured to selectively support a cartridge assembly 410 therein, and an upper jaw 442 secured to mounting portion 420 and being movable, relative to lower jaw 432, between approximated and spaced apart positions.

As seen in FIGS. 26-28, mounting portion 420 includes a coupling member 422 secured to a proximal end thereof. Coupling member 422 defines a substantially J-shaped channel 422a (see FIGS. 26-28) formed in a radial outer surface thereof that is configured and dimensioned for selective connection with complementary structure formed on or extending radially inward from collar 312 of end effector coupling assembly 310, as described above. Coupling member 422 further includes a pair of spaced apart alignment stems 424a, 424b projecting proximally therefrom, for receipt in respective alignment bores 310a, 310b formed in a distal surface of end effector coupling assembly 310.

The alignment stems 424a, 424b along with the alignment bores 310a, 310b are used to align and couple end effector 400 to end effector coupling assembly 310 of shaft assembly 200. The nub 312a of collar 312 and the J-shaped channel 422a of coupling member 422 may define a conventional bayonet-type coupling which facilitates quick and easy engagement and removal of end effector 400 from shaft assembly 200 before, during or after a surgical procedure.

Mounting portion 420 further includes, as seen in FIGS. 26, 28-31, 34 and 35 a drive axle 426 rotatably supported therein. Drive axle 426 includes a multi-faceted, proximal head 426a projecting proximally from coupling member 422 and being configured for mating engagement with third spur gear 282c of first gear train 280 of distal neck housing 236 and first gear train system 240 of shaft assembly 200, when end effector 400 is coupled to shaft assembly 200. Drive axle 426 further includes multi-faceted, a distal head 426b projecting distally from coupling member 422 and being configured for mating engagement with a threaded drive shaft 464 supported in lower jaw 432 of jaw assembly 430. Drive axle 426 functions to transmit rotational drive forces from third spur gear 282c of first gear train 280 of distal neck housing 236 and first gear train system 240 of shaft assembly 200, which defines an axis of rotation, to drive screw 464 of lower jaw 432 of jaw assembly 430, which defines an axis of rotation that is different than the axis of rotation of third spur gear 282c.

As seen in FIGS. 28-31, 34-36 and 39-43, lower jaw 432 of jaw assembly 430 includes a drive screw 464 rotatably supported therein and extending substantially an entire length thereof. Drive screw 464 includes a female coupling member 464a supported on a proximal end thereof and being configured for receipt of multi-faceted, distal head 426b of drive axle 426. Drive screw 464 is axially and laterally fixed within lower jaw 432 of jaw assembly 430 by a thrust plate 465, or the like, which is secured to jaw assembly 430 and at least partially extends into an annular channel 464a formed in drive screw 464. In operation, rotation of drive axle 426 results in concomitant rotation of drive screw 464.

Figure 33:
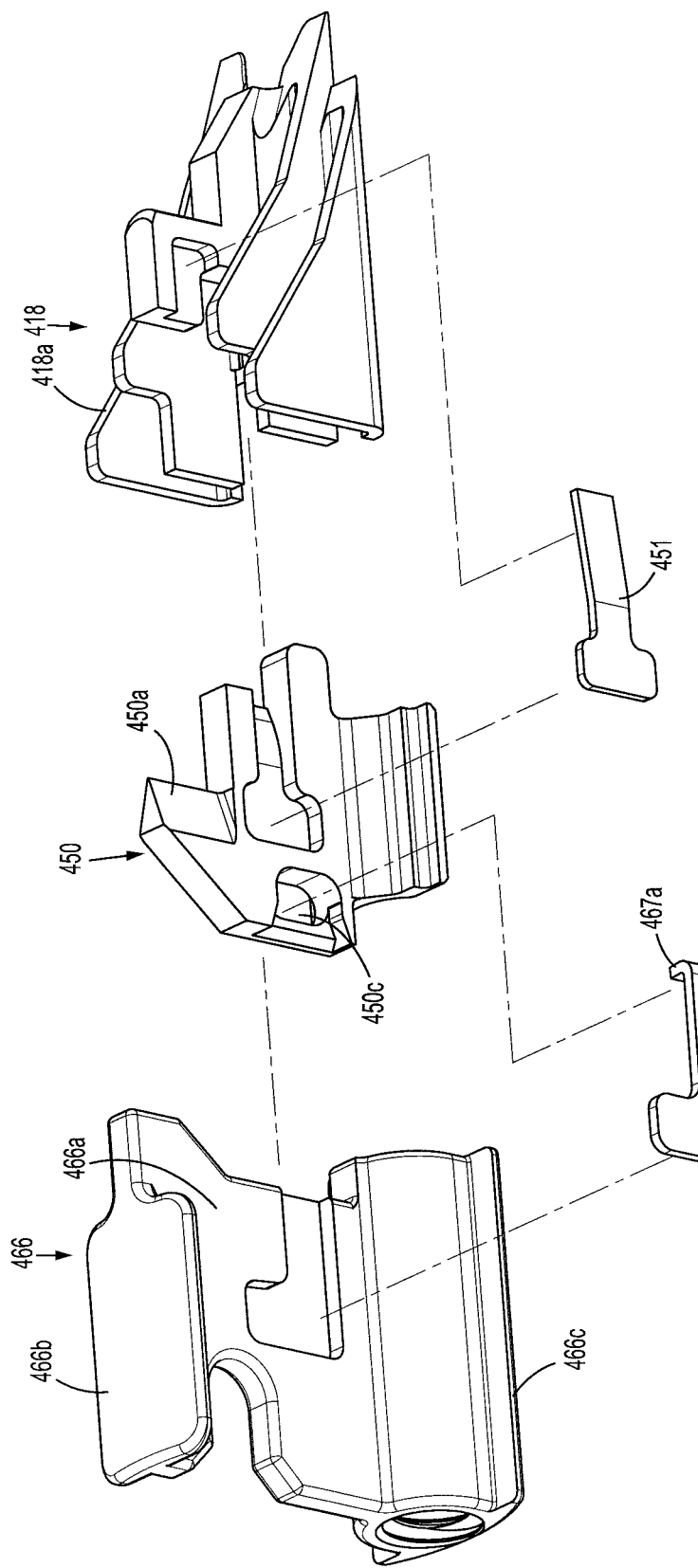
FIG. 33 is a perspective view, with parts separated, of the drive beam, the knife sled and the actuation sled of the end effector of FIGS. 27-29.

As seen in FIGS. 28-43, end effector 400 includes a drive beam 466 slidably supported in lower jaw 432 of jaw assembly 430. Drive beam 466 includes a substantially I-shaped cross-sectional profile and is configured to approximate lower jaw 432 and upper jaw 442, and to axially displace an actuation sled 468 through lower jaw 432. As seen in FIG. 33, drive beam 466 includes a vertically oriented support strut 466a; a lateral projecting member 466b formed atop support strut 466a and being configured to engage and translate with respect to an exterior camming surface of upper jaw 442 to progressively close jaw assembly 430; and a retention foot 466c having an internally threaded bore for threadable connection to threaded drive shaft 464. Since drive beam 466 is prevented from rotation by the engagement of strut 466a and/or cam member 466b with upper jaw 442, as drive screw 464 is rotated, retention foot 466c, and in turn, drive beam 466 is axially translated relative to lower jaw 432.

Drive beam 466 includes a lock clip 467 extending distally from strut 466a. Lock clip 467 defines a hook 467a configured to engage a window 450c formed in a knife sled 450, as will be discussed in greater detail below. Hook 467a of lock clip 467 is biased to extend away from knife sled 450. Prior to firing the cartridge assembly 410, the drive beam 466 is at a proximal-most position in lower jaw 432 and actuation sled 418 and knife sled 450 are at a proximal-most position in cartridge body 412, as seen in FIGS. 36 and 37. Lock clip 467, prior to firing, is disengaged from window 450c of knife sled 450 and extends into a relief 412e defined in a wall of knife slot 412b.

Lower jaw 432 is in the form of a channel and is configured and adapted to selectively receive a disposable staple cartridge assembly 410 therein. Staple cartridge assembly 410 includes a cartridge body 412 defining a plurality of rows of staple retaining slots 412a and a longitudinally extending knife slot 412b disposed between pairs of rows of staple retaining slots 412a. Staple cartridge assembly 410 also includes a plurality of staples 433 disposed, one each, in the plurality of retaining slots 412a. Staple cartridge assembly 410 further includes a plurality of staple pushers 416 supported therein, wherein the staple pushers 416 are aligned one each within retaining slots 412a such that a single staple pusher 416 is positioned under a respective staple 433 which is retained within slot 412a. Staple pushers 416 may be formed such that they are attached to each other in a pusher member having groups of two or three pushers, wherein the pusher member may have offset oriented pushers. One or more actuating surfaces is provided on a lower surface of the pusher member (not shown).

Staple cartridge assembly 410 includes an actuation sled 418 slidably supported against a lower surface of cartridge body 412 and being engageable by drive beam 466. Actuation sled 418 includes upstanding cam wedges 418a configured to exert a driving force on staple pushers 416, by contacting the actuating surfaces, which drives staples 414 from staple cartridge assembly 410, as described in greater detail below.

Cartridge body 412 defines a plurality of spaced apart longitudinal channels 412c (see FIG. 36) extending therethrough to accommodate the upstanding cam wedges 418a of actuation sled 418. Channels 412c communicate with the plurality of retaining slots 412a within which the plurality of staples 433 and pushers 416 are respectively supported.

As seen in FIGS. 28-43, staple cartridge assembly 410 further includes a knife sled 450 slidably supported within knife slot 412b of cartridge body 412 and being interposed between drive beam 466 and actuation sled 468. As seen in FIG. 33, knife sled 450 defines a knife blade 450a extending from an upper surface thereof and oriented distally, wherein knife blade 450a extends through knife slot 412b of cartridge body 412. Knife sled 450 includes a lock-out spring 451 extending distally therefrom for engaging a lock-out notch 412d formed in a surface of cartridge body 412 (see FIG. 37), as will be discussed in greater detail below. Lock-out spring 451 is biased toward lock-out notch 412d. Prior to firing of cartridge assembly 410, with actuation sled 418 and knife sled 450 at a proximal-most position in cartridge body 412, as seen in FIG. 34-37, lock-out spring 451 is blocked by actuation sled 418 from entering lock-out notch 412d of cartridge body 412.

Staple cartridge assembly 410 includes a bottom cover or retainer 415 configured to maintain the plurality of staple pushers 416, actuation sled 418 and knife sled 450 within cartridge body 412. Retainer 415 supports and aligns the plurality of pushers 416 prior to engagement thereof by the actuation sled 418. During operation, as actuation sled 418 translates through staple cartridge assembly 410, the angled leading edges of cam wedges 418a of actuation sled 418 sequentially contact pushers 416, causing the pushers 416 to translate vertically within retaining slots 412a, urging the staples 433 therefrom. Also, as knife sled 450 translates through knife slot 412b of cartridge body 412, knife blade 450a severs tissue and retaining sutures that extend across knife slot 412b of cartridge body 412.

In operation, as drive screw 464 is rotated, in a first direction, to advance drive beam 466, as described above, drive beam 466 is advanced into contact with knife sled 450 and actuation sled 418 to distally advance or push knife sled 450 and actuation sled 418 through cartridge body 412 and lower jaw 432. As drive beam 466 is continually driven in the distal direction, drive beam 466 maintains contact with knife sled 450 and actuation sled 418, thereby pushing knife sled 450 and actuation sled 418 in the distal direction and to approximate lower jaw 430 and upper jaw 440, as laterally projecting member 466b of drive beam 466 pushes down on the exterior camming surface of upper jaw 440, to eject the staples 414 and fasten tissue, and to simultaneously dissect tissue with knife blade 450a. Knife sled 450, actuation sled 418 and drive beam 466 travel through cartridge body 412 thereby fastening and severing tissue.

Figure 38:
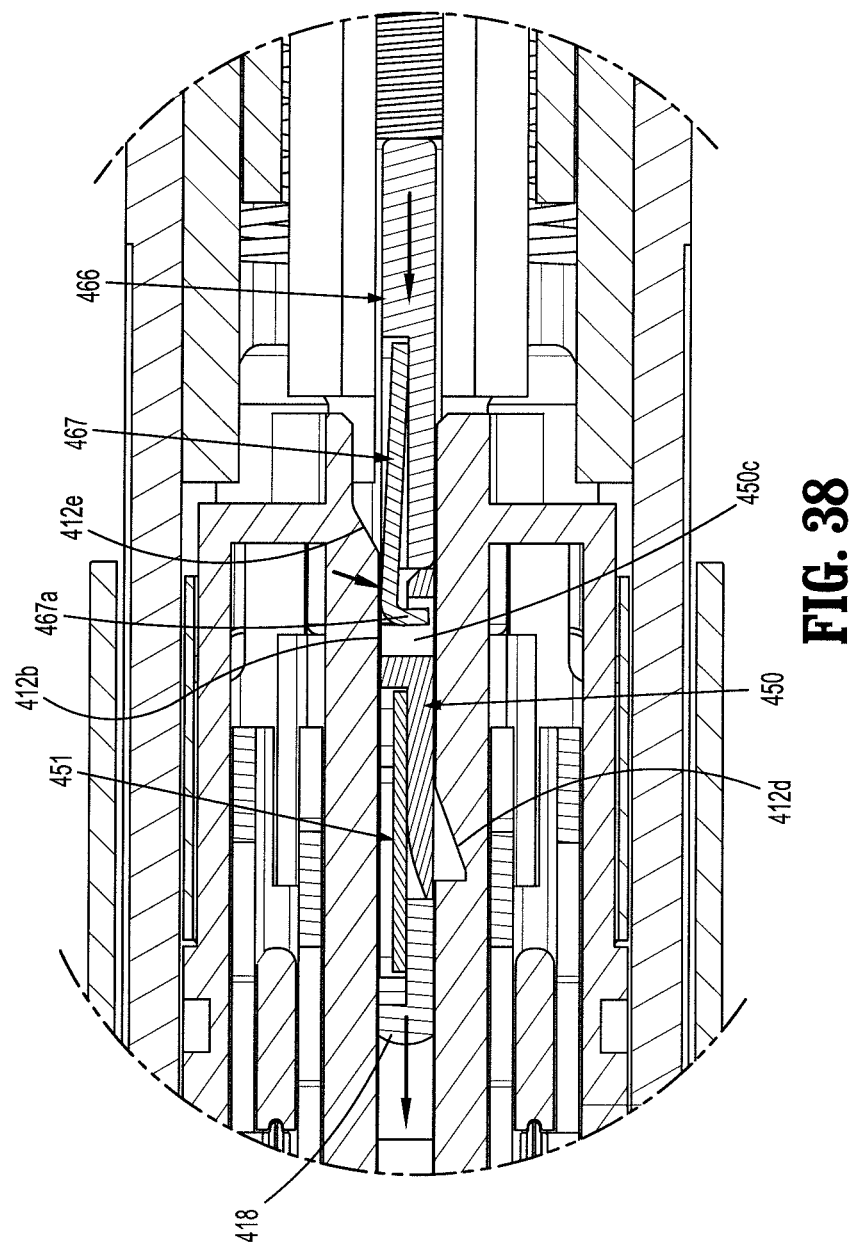
FIG. 38 is a further enlarged view illustrating the drive beam, the knife sled and the actuation sled in a distally advanced position.
Figure 41:
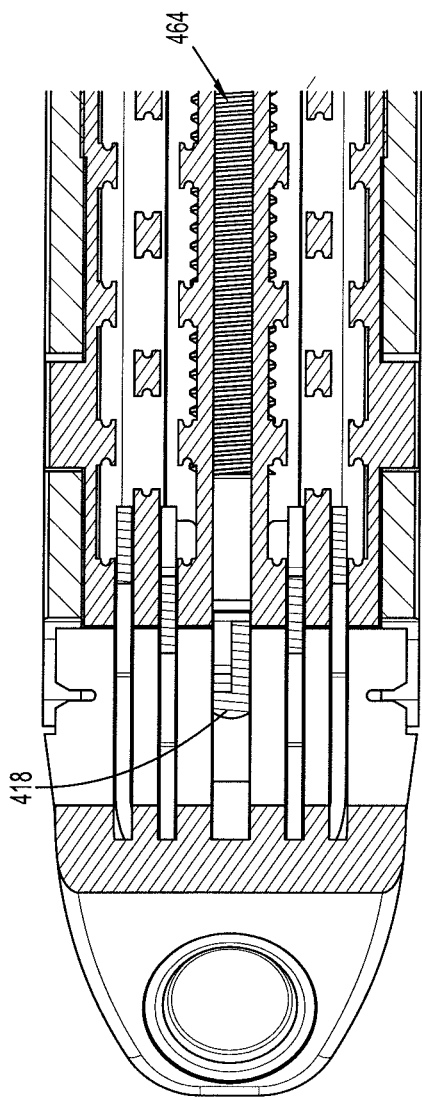
FIG. 41 is a cross-sectional view of a distal end of the end effector of FIG. 27, as taken through 34-34 of FIG. 27, illustrating the actuation sled in a distal-most position.
Figure 42:
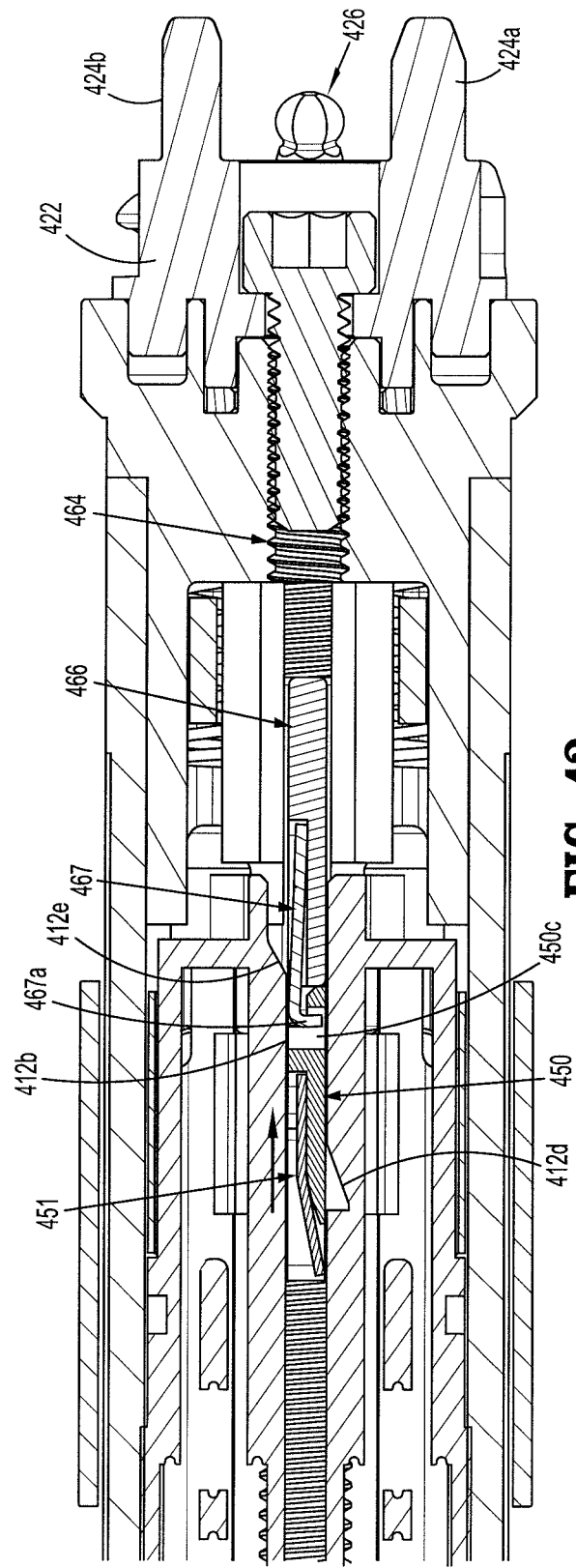
FIG. 42 is a cross-sectional view of a proximal end of the end effector of FIG. 27, as taken through 34-34 of FIG. 27, illustrating the drive beam and the knife sled in a proximal position.

As seen in FIGS. 37 and 38, as drive beam 466 is advanced distally, hook 467a of lock clip 467 exits relief 412e and is cammed into window 450c of knife sled 450 as hook 467a enters knife slot 412b of cartridge body 412. Drive screw 464 is rotated until actuation sled 418, knife sled 450 and drive beam 466 reach a distal-most end of cartridge body 412 and/or lower jaw 432, for a complete firing.

Following a complete or partial firing, drive screw 464 is rotated in an opposite direction to retract drive beam 466. Since and knife sled 450 is connected to drive beam 466 by lock clip 467, as described above, as drive beam 466 is retracted, knife sled 450 is also retracted. Actuation sled 418 will tend to remain at a distal or distal-most position due to its frictional engagement in channels 412c of cartridge body 412 (see FIG. 40). Drive screw 464 is rotated until drive beam 466 and knife sled 450 are returned to the proximal-most position. Once drive beam 466 and knife sled 450 are returned to the proximal-most position, hook 467a of lock clip 467 is permitted to re-enter relief 412e, due to its own resiliency, and disengage from window 450c of knife sled 450. As such, drive beam 466 is disengaged from knife sled 450, and staple cartridge assembly 410 is free to be removed from lower jaw 432.

Figure 43:
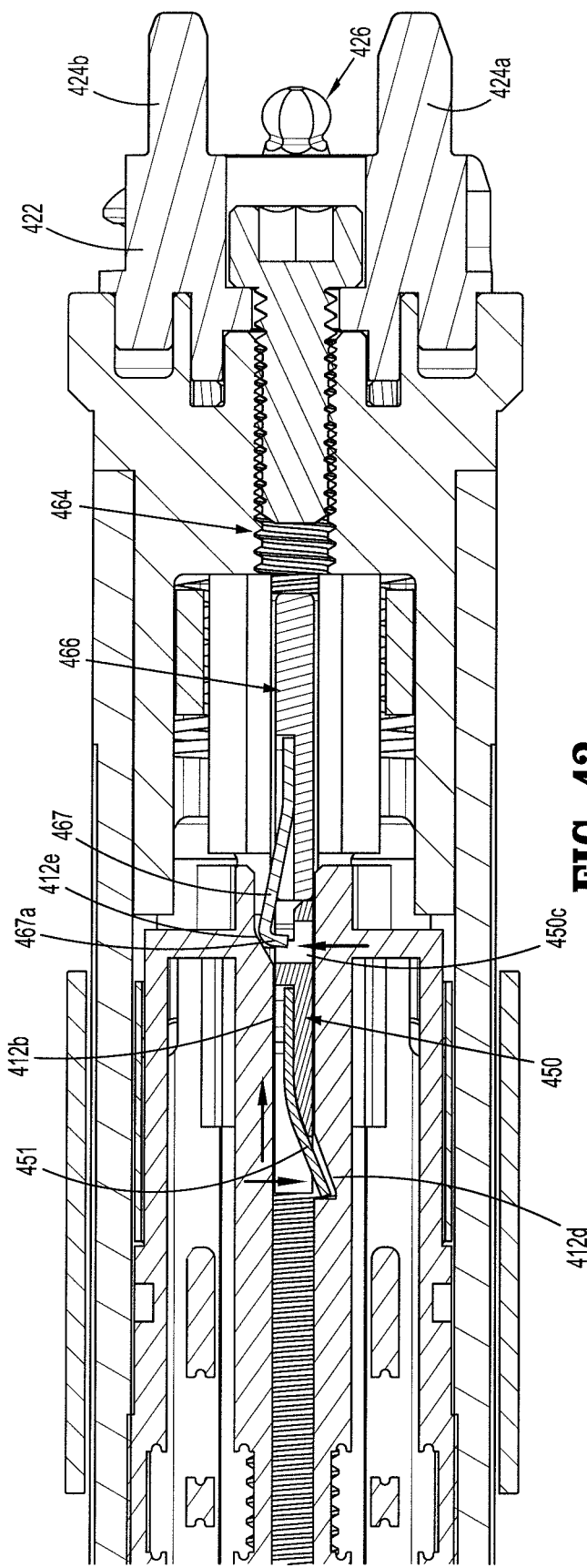
FIG. 43 is a cross-sectional view of a proximal end of the end effector of FIG. 27, as taken through 34-34 of FIG. 27, illustrating the drive beam and the knife sled in a proximal-most position.
Figures 44, 45:
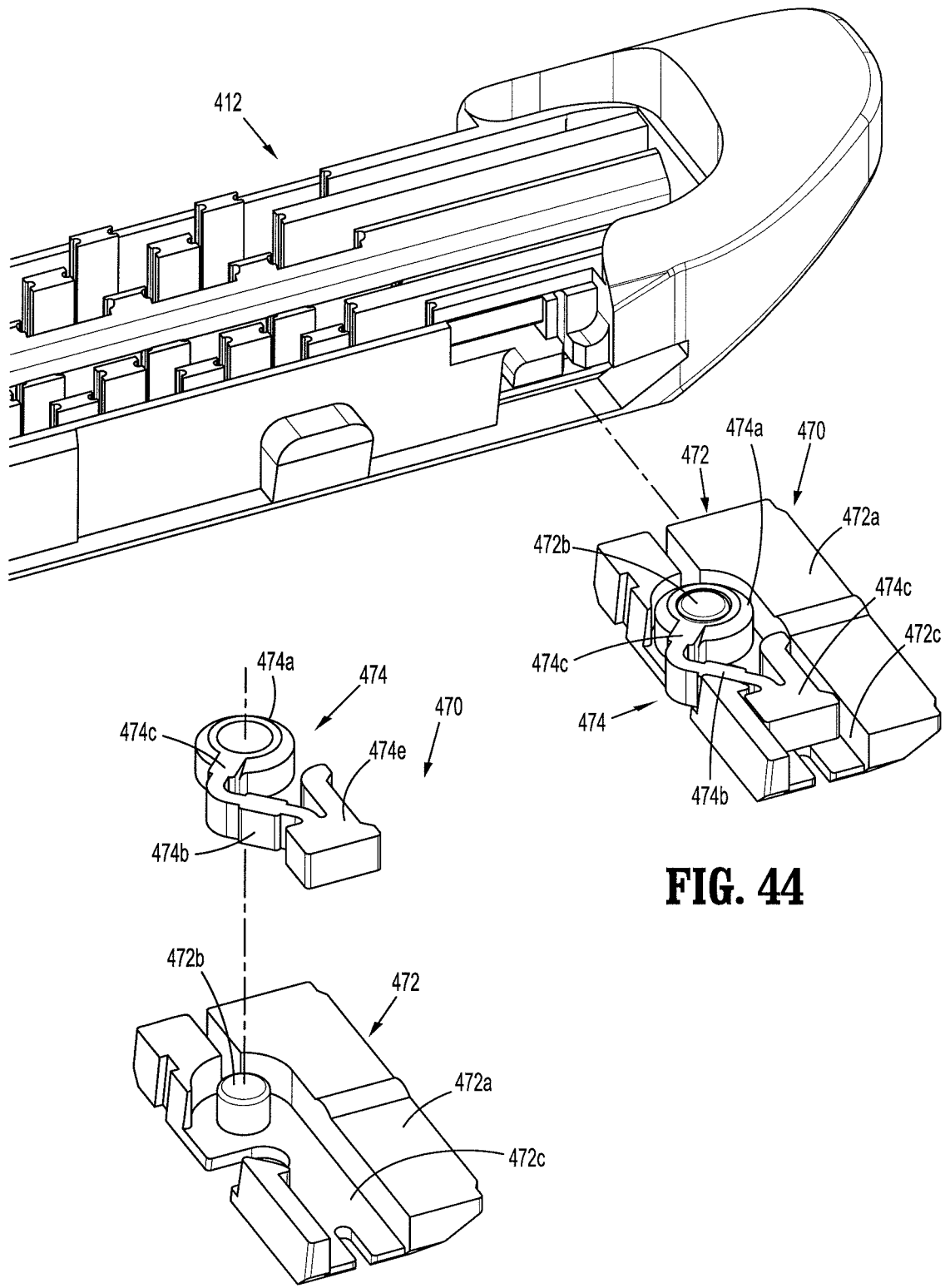
FIG. 44 is a perspective view, with parts partially separated, of a release assembly supported in a distal end of a cartridge assembly of the end effector.
FIG. 45 is a perspective view, with parts separated, of the release assembly of FIG. 44.

Also, when drive beam 466 and knife sled 450 are returned to the proximal-most position, with actuation sled 418 now separated from knife sled 450, since lock-out spring 451 is biased toward lock-out notch 412d, as seen in FIG. 43, lock-out spring 451, which is attached to knife sled 450, is now free to enter lock-out notch 412d and prevent knife sled 450 and/or drive beam 466 being re-advanced, thereby locking-out staple cartridge assembly 410.

In order for drive beam 466 to be re-advanced, a new, un-fired staple cartridge assembly 410 needs to be loaded into lower jaw 432.

Upper jaw 442 of jaw assembly 430 functions as an anvil against which the staples 433 form when actuation sled 418 is advanced during a firing of surgical instrument 100. In particular, upper jaw 442 includes an anvil plate 443, secured to a cover housing 444, in juxtaposed relation to staple cartridge assembly 410. Anvil plate 443 defines a plurality of staple forming pockets (not shown), arranged in longitudinally extending rows that cooperate with the rows of staple retaining slots 412a of staple cartridge assembly 410, when staple cartridge assembly 410 is disposed in lower jaw 432.

Lower jaw 432 is pivotably connected to mounting portion 420 by way of appropriate pivot pins 445 or the like extending through a pair of spaced apart shoulders 432a, 432b disposed near a proximal end thereof. Shoulders 432a, 432b of lower jaw 432 extend into reliefs or the like formed in mounting portion 420.

As seen in FIG. 28, jaw assembly 430 includes at least one biasing member 447, in the form of a compression spring or the like, disposed between each shoulder 432a, 432b of lover jaw 432 and a bearing surface of mounting portion 420 such that lower jaw 432 is spaced from upper jaw 442, until closed, to maintain jaw assembly 430 in an open position. In use, as jaw assembly 430 is closed, by approximating upper jaw 442 and lower jaw 432, biasing members 447 are biased (i.e., compressed) between shoulders 432a, 432b of lower jaw 432 and the bearing surface of mounting portion 420.

Following firing of staple cartridge assembly 410, drive screw 464 is rotated, in a second direction that is opposite the first direction, to withdraw drive beam 466 and knife sled 450, as described above. As drive beam 466 is withdrawn in a proximal direction, biasing members 447 begin to expand to press apart shoulders 432a, 432b of lower jaw 432 from the bearing surface of mounting portion 420 to separate the upper jaw 442 from the lower jaw 432 to open jaw assembly 430.

In accordance with the present disclosure, cartridge body 412 of staple cartridge assembly 410 may be configured and adapted to selectively support a surgical buttress on a tissue contact surface thereof. With reference to FIG. 28, cartridge body 412 of staple cartridge assembly 410 defines a proximal pair of recesses formed near a proximal end thereof and disposed, one each, on opposed sides of longitudinally extending knife slot 412b. Cartridge body 412 further defines a distal pair of recesses 412e formed near a distal end thereof and disposed, one each, on opposed sides of longitudinally extending knife slot 412b. In one embodiment, the distal pair of recesses 412e is preferably non-circular and constricting or otherwise arranged so as to frictionally engage and/or pinch an anchor "S".

As seen in FIG. 28, cartridge body 412 further includes a surgical cartridge buttress "B1", pledget or the like operatively secured to an upper surface or tissue contacting surface thereof, by suture anchors "S1" and "S2", to overlie at least some of the plurality of staple retaining slots 412a and/or at least a portion of a length of longitudinally extending knife slot 412b. In particular, an anchor "S1" is cinched around a proximal portion of surgical cartridge buttress "B1" and each of the proximal pair of recesses and an anchor "S2" is cinched around a distal portion of the surgical cartridge buttress "B1" and each of the distal pair of recesses 412e. The anchors may comprise a surgical suture.

In one particular embodiment, a first end of suture anchor "S1" includes a knot, stop or the like (not shown) sized so as to not pass through one recess of the proximal pair of recesses and a second end of suture anchor "S1" passes over, and transversely across, surgical cartridge buttress "B1", at least once, and back through the other recess of the proximal pair of recesses. For example, the second end of suture anchor "S1" may be pinched or cinched in the other recess of the proximal pair of recesses so as to anchor the second end of the suture anchor "S1" and secure the surgical cartridge buttress "B1" against the tissue contacting surface of cartridge body 412. Similarly, a suture anchor "S2" is used to extend transversely across surgical cartridge buttress "B1" and into engagement with the distal pair of recesses 412e.

Surgical cartridge buttress "B1" includes a proximal pair of notches formed in side edges aligned with the proximal pair of recesses of cartridge body 412, a distal pair of notches formed in side edges thereof aligned with the distal pair of recesses 412e of cartridge body 412, and a proximal notch formed in a proximal edge thereof aligned with longitudinally extending knife slot 412b when cartridge buttress "B1" is secured to cartridge body 412. Cartridge buttress "B1" further includes a tongue or tab extending from a distal edge thereof to facilitate with the attachment of cartridge buttress "B1" to cartridge body 412 during the assembly process. It is contemplated that a width of cartridge buttress "B1" may be reduced in a proximal portion thereof. It is further contemplated that the tongue is removed from cartridge buttress "B1" following securement of cartridge buttress "B1" to cartridge body 412 and prior to packaging or shipment.

As seen in FIGS. 28 and 44-47, cartridge body 412 of staple cartridge assembly 410 includes a cartridge buttress release assembly 470 supported in and near a distal end of cartridge body 412. Release assembly 470 includes a retainer 472 supported in a distal end of cartridge body 412 at a location near a distal end of longitudinally extending knife slot 412b and at least partially extending thereacross. Retainer 472 includes a body portion 472a, a boss 472b extending from a surface thereof, and defines a channel or recess 427c formed in a surface thereof and extending through a side thereof. When supported in cartridge body 412, recess 472c of retainer 472 is in registration with one of the pair of distal recesses 412e of cartridge body 412.

Release assembly 470 further includes a pusher member 474 having a head portion 474a pivotally connected to boss 472b of retainer 472. Pusher member 474 further includes a first leg member 474b extending from head portion 474a and a second leg member 474c connected to a free end of first leg member 474b via a living hinge connection. Pusher member 474 further includes piston 474e connected to a free end of second leg member 474c via a living hinge connection. Piston 474e is slidably disposed and translatable within recess 472c of retainer 472. In certain other embodiments, the pusher is a linkage assembly having a first link pivotally connected to the cartridge body at one end. The other end of the first link is pivotally connected to a first end of a second link. The opposite, second, end of the second link is confined in the recess of the retainer.

Figure 46:
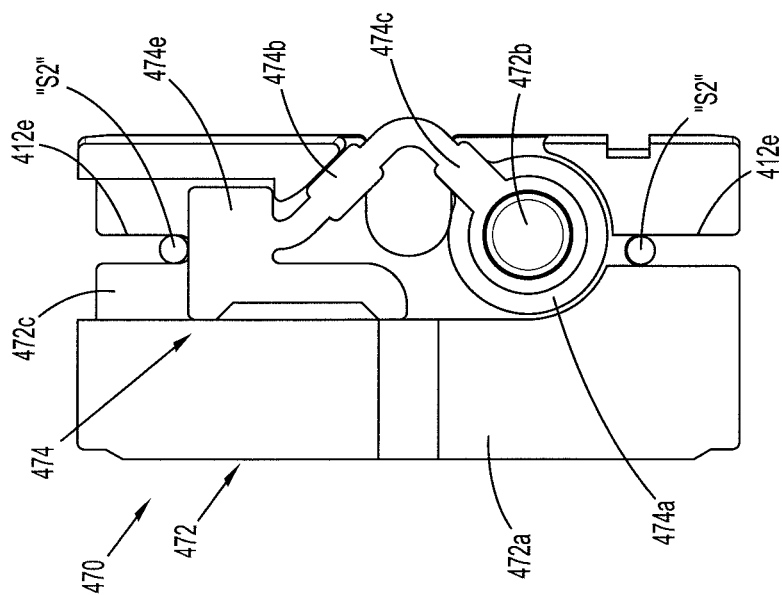
FIG. 46 is a plan view of the release assembly of FIGS. 44 and 45, shown in an unactuated condition.

As seen in FIG. 46, release assembly 470 includes an unactuated configuration wherein piston 474e does not extend into or overlie the respective one of the pair of distal recesses 412e of cartridge body 412, and first leg member 474b and second leg member 474c are angled with respect to one another and project proximally along longitudinally extending knife slot 412b of cartridge body 412. It is contemplated that release assembly 470 may include a friction fit or snap fit feature for maintaining and/or retaining release assembly 470 in the locking or anchoring configuration at all times following the manufacturing/assembly process and prior to a complete firing of surgical instrument 100.

Figure 47:
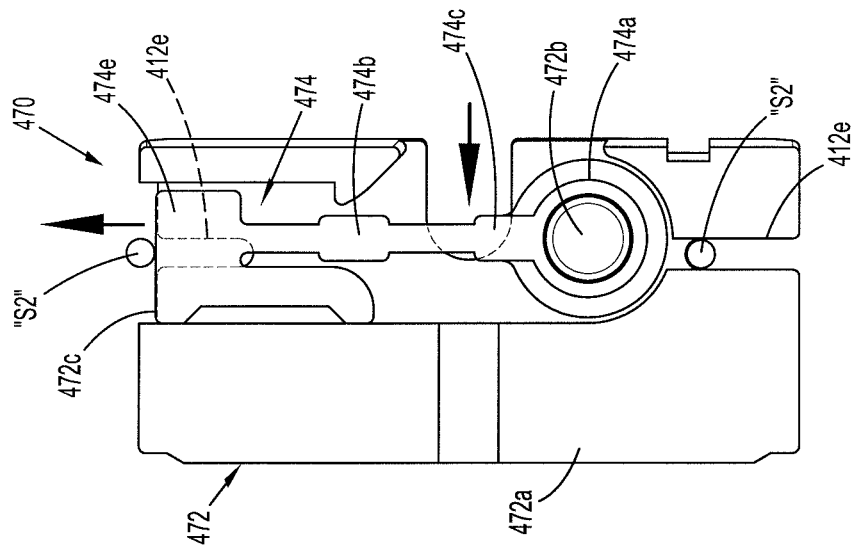
FIG. 47 is a plan view of the release assembly of FIGS. 44 and 45, shown in an actuated condition.

As seen in FIG. 47, release assembly 470 includes an actuated configuration wherein piston 474e extends into or overlies the respective one of the pair of distal recesses 412d of cartridge body 412 in operative registration therewith, and first leg member 474b and second leg member 474c are extended substantially along a common axis.

In operation, with surgical cartridge buttress "B1" secured against the tissue contacting surface of cartridge body 412, during firing of surgical instrument 100, as drive beam 466 is advanced (i.e., moved from a proximal-most position to a distal-most position), knife blade 450a of knife sled 450 slices through a central section of proximal suture anchor "S1", thereby freeing the proximal end of the surgical cartridge buttress "B1" from cartridge body 412. During use, as the firing stroke of surgical instrument 100 is nearing completion and as actuation sled 418 approaches a distal end of longitudinally extending knife slot 412bc of cartridge body 412, actuation sled 418 contacts the living hinge connection between first leg member 474b and second leg member 474c. As actuation sled 418 is further advanced distally, actuation sled 418 presses against the living hinge connection, causing first leg member 474b and second leg member 474c to extend. As first leg member 474b and second leg member 474c extend, piston 474e is translated through recess 472c of retainer 472. As piston 474e is translated through recess 472c of retainer 472, piston 474e engages the second end of suture anchor "S2" and urges the second end of suture anchor "S2" out of the distal recess 412d of cartridge body 412 that is in registration therewith to release the second end of suture anchor "S2" therefrom. With the second end of suture anchor "S2" released or free from distal recess 412d of cartridge body 412, the distal end of the surgical cartridge buttress "B1" is free to separate from the tissue contacting surface of cartridge body 412.

As seen in FIG. 28, upper jaw 442 further includes a surgical anvil buttress "B2", pledget or the like operatively secured to an upper surface or tissue contacting surface thereof, by anchors "S3" and "S4", to overlie at least some of the plurality of staple forming pockets and/or at least a portion of a length of a longitudinally extending knife slot of anvil plate 443. The anchors may comprise surgical sutures. In particular, a suture anchor "S3" is cinched around a proximal portion of surgical anvil buttress "B2" and each of the proximal pair of recesses and a suture anchor "S4" is cinched around a distal portion of the surgical anvil buttress "B2" and each of a distal pair of recesses 443a formed in opposed side edges of anvil plate 443.

In one particular embodiment, a first end of suture anchor "S3" includes a knot, stop or the like (not shown) sized so as to not pass through one recess of the proximal pair of recesses and a second end of suture anchor "S3" passes over, and transversely across, surgical anvil buttress "B2", at least once, and back through the other recess of the proximal pair of recesses. For example, the second end of suture anchor "S3" may be pinched or cinched in the other recess of the proximal pair of recesses so as to anchor the second end of the suture anchor "S3" and secure the surgical anvil buttress "B2" against the tissue contacting surface of anvil plate 443. Similarly, a suture anchor "S4" is used to extend transversely across surgical anvil buttress "B2" and into engagement with the distal pair of recesses 443a.

Surgical anvil buttress "B2" includes a proximal pair of notches formed in side edges aligned with the proximal pair of recesses of anvil plate 443, a distal pair of notches formed in side edges thereof aligned with the distal pair of recesses 443a of anvil plate 443, and a proximal notch formed in a proximal edge thereof aligned with longitudinally extending knife slot when anvil buttress "B2" is secured to anvil plate 443. Anvil buttress "B2" further includes a tongue or tab extending from a distal edge thereof to facilitate with the attachment of anvil buttress "B2" to anvil plate 443 during the assembly process. It is contemplated that the tongue is removed from anvil buttress "B2" following securement of anvil buttress "B2" to anvil plate 443 and prior to packaging or shipment.

Figure 48:
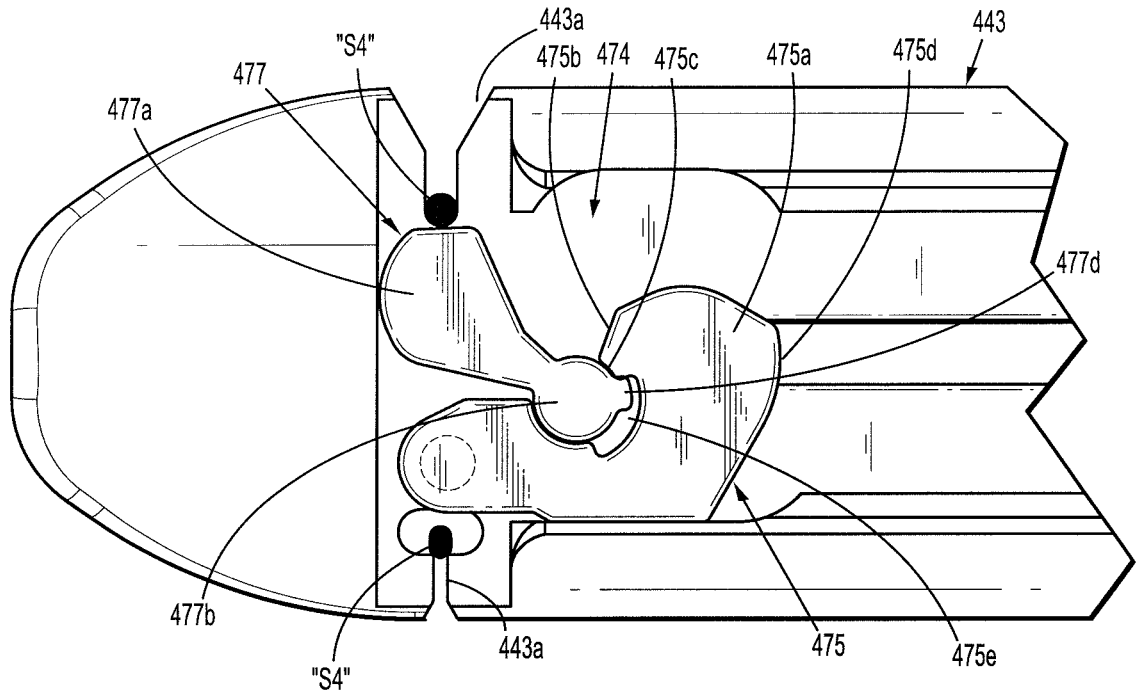
FIG. 48 is a plan view of a release assembly supported in a distal end of an upper jaw of the end effector, illustrated in an unactuated condition.
Figure 49:
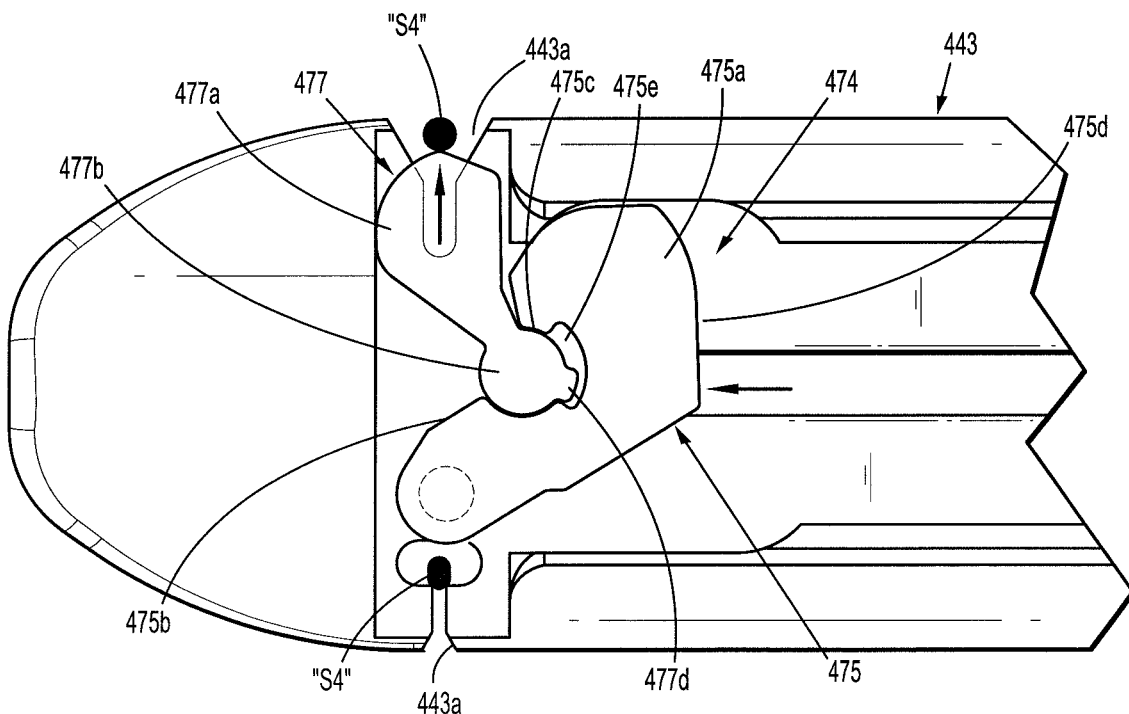
FIG. 49 is a plan view of the release assembly of FIG. 48, illustrated in an actuated condition.
Figure 50:
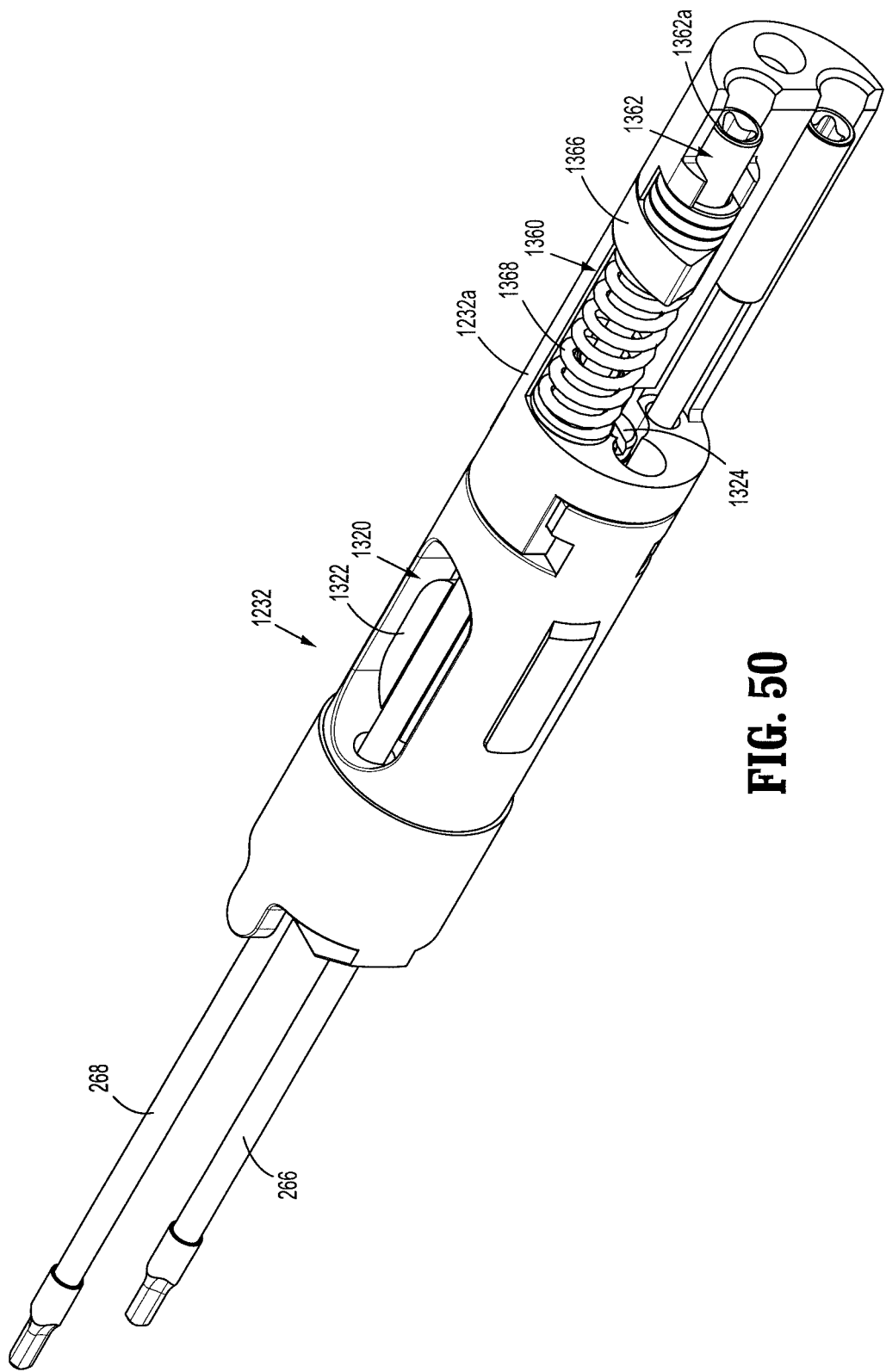
FIG. 50 is a perspective view of a proximal portion of a neck assembly of the shaft assembly, according to another embodiment of the present disclosure.
Figure 51:
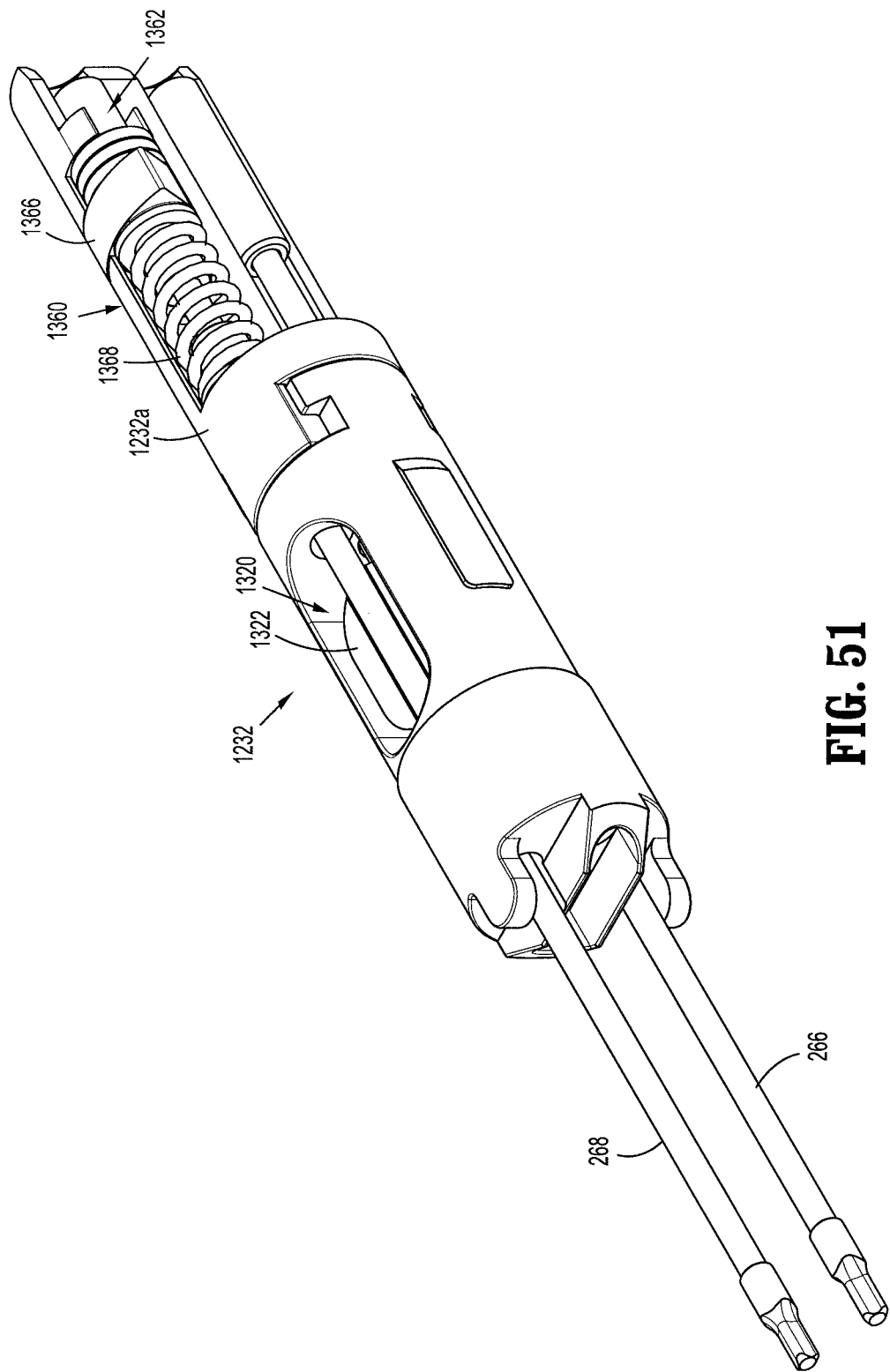
FIG. 51 is another perspective view of the proximal portion of the neck assembly of the shaft assembly of FIG. 50.
Figure 54:
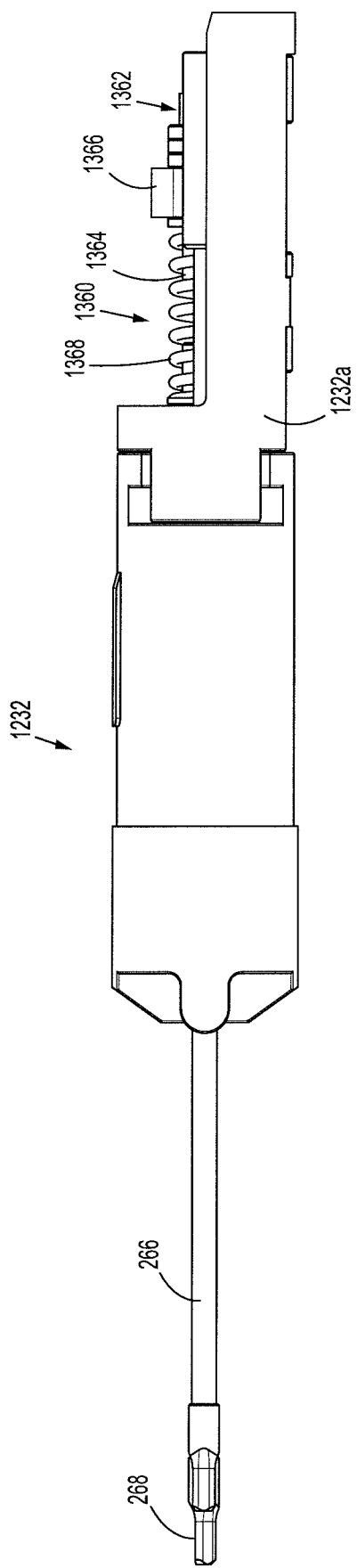
FIG. 54 is a bottom, plan view of the proximal portion of the neck assembly of FIGS. 50 and 51.

As seen in FIGS. 28 and 48-49, upper jaw 442 of jaw assembly 430 includes a suture release assembly 474 disposed between anvil plate 443 and cover housing 444 at a location in operative registration with a distal pair of side recesses 443a. Suture release assembly 474 includes a link arm 475 pivotally connected to anvil plate 443 and/or optionally cover housing 444. Link arm 475 includes a body portion 475a defining a pocket or recess 475c formed in a first side edge 475b thereof and a camming surface 475d defined substantially along an adjacent side or proximal edge thereof. Pocket 475c has a substantially arcuate, circular or rounded profile and defines an arcuate relief 475e in a side wall thereof. Link arm 475 includes a pivot pin extending from body portion 475a for pivotally connecting link arm 475 to upper jaw 442.

Release assembly 474 further includes a pusher bar 477 pivotally connected to link arm 475 and slidably disposed between anvil plate 443 and cover housing 444. Pusher bar 477 includes a body portion 477a having a substantially rectangular configuration and a head 477b, extending from a corner of body portion 477a, and having a substantially circular or rounded configuration. Head 477b of pusher bar 477 is configured and dimensioned for pivotable and/or rotatable connection in pocket 475c of link arm 475. Head 477b of pusher bar 477 includes a stop member 477d projecting from a side edge thereof and into arcuate relief 475e of pocket 475c of link arm 475. A relative distance of rotation of pusher bar 477 relative to link arm 475 is determined by a relative length of arcuate relief 475e and a relative width of stop member 477d.

As seen in FIG. 48, suture release assembly 474 includes an unactuated configuration wherein pusher bar 477 does not extend into or overlie the respective one of the pair of distal recesses 443a in operative registration therewith, and a longitudinal axis of link arm 475 is oriented substantially parallel with a longitudinal axis of upper jaw 442. It is contemplated that suture release assembly 474 may include a friction fit or snap fit feature for maintaining and/or retaining suture release assembly 474 in the locking or anchoring configuration at all times following the manufacturing/assembly process and prior to a complete firing of the surgical stapling apparatus.

As seen in FIG. 49, suture release assembly 474 includes an actuated configuration wherein pusher bar 477 extends into or overlies the respective one of the pair of distal recesses 443a in operative registration therewith, and a longitudinal axis of link arm 475 is oriented substantially transverse to the longitudinal axis of upper jaw 442.

With reference to FIGS. 28 and 34-43, in operation, with a surgical anvil buttress (not shown) secured against the lower surface of anvil plate 443, during firing of the surgical stapling apparatus, as drive beam 466 is advanced (i.e., moved from a proximal-most position to a distal-most position), knife blade 450a slices through a central section of the proximal suture (not shown), thereby freeing the proximal end of the surgical anvil buttress (not shown) from upper jaw 442. During use, as the firing stroke of the surgical instrument is nearing completion and as drive beam 466 approaches a distal-most end of the knife slot of anvil plate 443, as seen in FIG. 49, actuation sled 418 contacts camming surface 475d of link arm 475, thus urging link arm 475 to rotate or pivot around the pivot pin and, in turn, urging pusher bar 477 to translate in the direction of the slot. As pusher bar 477 is translated, pusher bar 477 comes into contact with and urges the second end of suture "S4" out of the distal recess 443a that is registration therewith to release the second end of suture "S4" therefrom. With the second end of surgical suture "S4" released or free from distal recess 443a, the distal end of the surgical anvil buttress "B2" is free to separate from the tissue contacting surface of anvil plate 443.

Exemplary surgical buttresses "B" for use with the staple cartridge assembly 410 and/or anvil plate 443 disclosed herein are shown and described in commonly assigned U.S. Pat. Nos. 5,542,594, 5,908,427, 5,964,774, 6,045,560, and 7,823,592; commonly assigned U.S. application Ser. No. 12/579,605, filed on Oct. 15, 2009 (now U.S. Pat. No. 8,157,151); commonly assigned U.S. application Ser. No. 11/241,267, filed on Sep. 30, 2005 (now U.S. Pat. No. 7,938,307); and U.S. application Ser. No. 13/097,194, filed on Apr. 29, 2011 (now U.S. Pat. No. 8,365,972), the entire contents of each of which are incorporated by reference herein.

Surgical buttresses "B" may be fabricated from a suitable biocompatible and bioabsorbable material. Surgical buttresses "B" may be fabricated from a non-absorbent material which does not retain fluid. Surgical buttresses "B" may be fabricated from "BIOSYN" made from GLYCOMER 631 (a block copolymer), a synthetic polyester composed of glycolide, dioxanone and trimethylene carbonate.

One block of the resulting copolymer contains randomly combined units derived from p-dioxanone (1,4-dioxan-2-one) and trimethylene carbonate (1,3-dioxan-2-one). The second block of the copolymer contains randomly combined units derived from glycolide and p-dioxanone. The resulting polyester is an ABA triblock terpolymer possessing about 60% glycolide, about 14% dioxanone, and about 26% trimethylene carbonate.

The surgical buttress may comprise polymers or copolymers of glycolide, lactide, poly caprolactone, trimethylene carbonate, dioxanone, caprolactone, and may be molded, extruded, etc. into a desired shape, or formed into a knitted, woven, braided, non-woven or felted material.

In a further embodiment, an electromechanical, handheld, powered surgical system 10 as discussed above has an alternative neck assembly. Electromechanical surgical system 10 is an electromechanical, hand-held, powered surgical instrument 100 that is configured for selective attachment to of a plurality of different end effectors, via the shaft assembly 200, as discussed above. FIGS. 50-66, show the alternative proximal neck assembly 230, according to certain embodiments of the present disclosure, is generally designated as 1232. Otherwise, the system 10 is as discussed above.

As seen in FIGS. 55, 56, 61, 65 and 66, proximal neck housing 1232 of neck assembly 230 supports an articulation assembly 1270 configured and adapted to impart articulation to neck assembly 230 and the end effector 400. Articulation assembly 1270 includes a pair of opposed gear racks 1272, 1274 engaged with and on opposed sides of a pinion gear 1276. See FIG. 55. Racks 1272, 1274 are axially and movably supported in proximal neck housing 1232 and the pinion gear 1276 is rotatably supported in proximal neck housing 1232.

Figure 55:
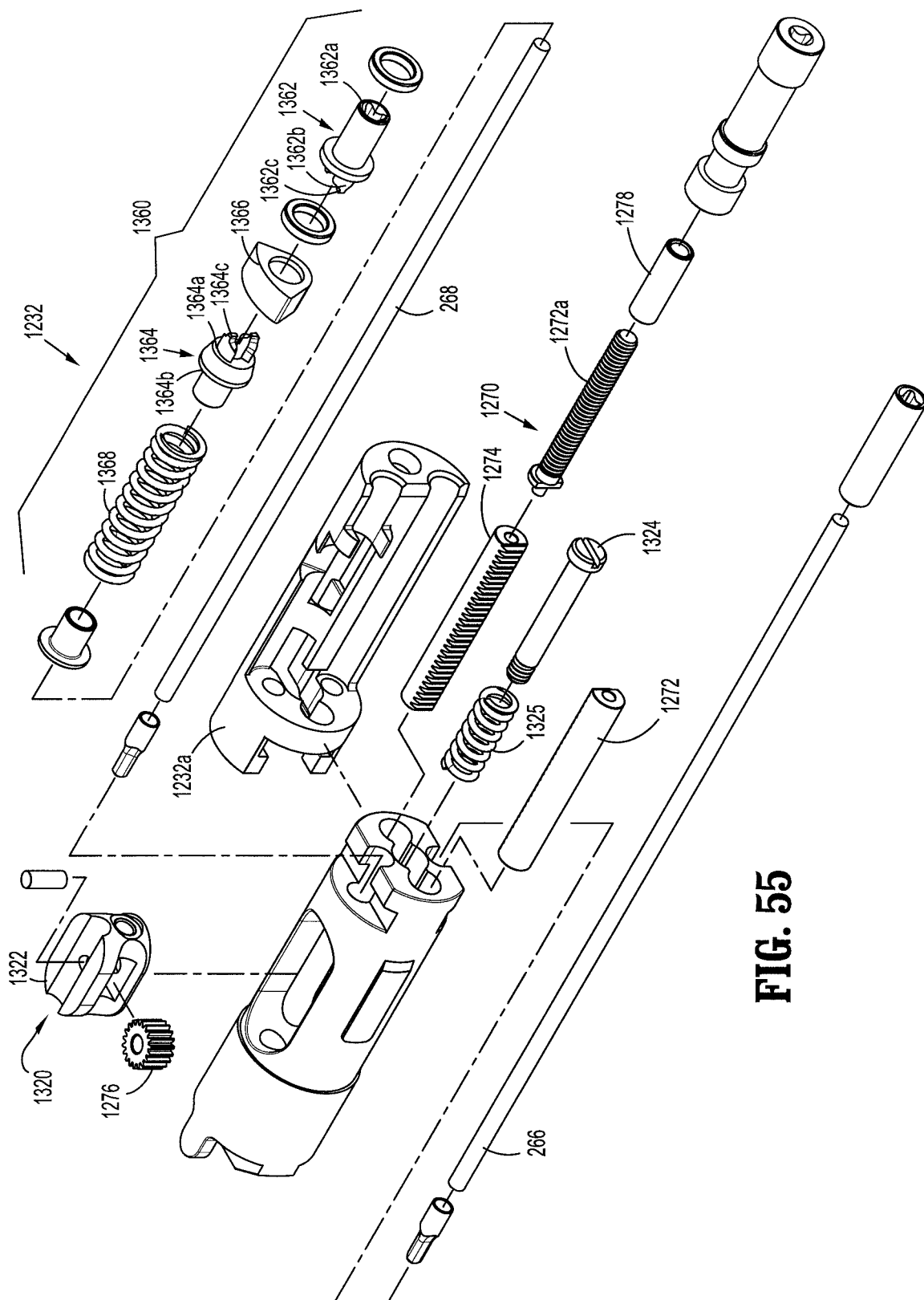
FIG. 55 is a perspective view, with parts separated, of the proximal portion of the neck assembly of FIGS. 50 and 51.
Figure 56:
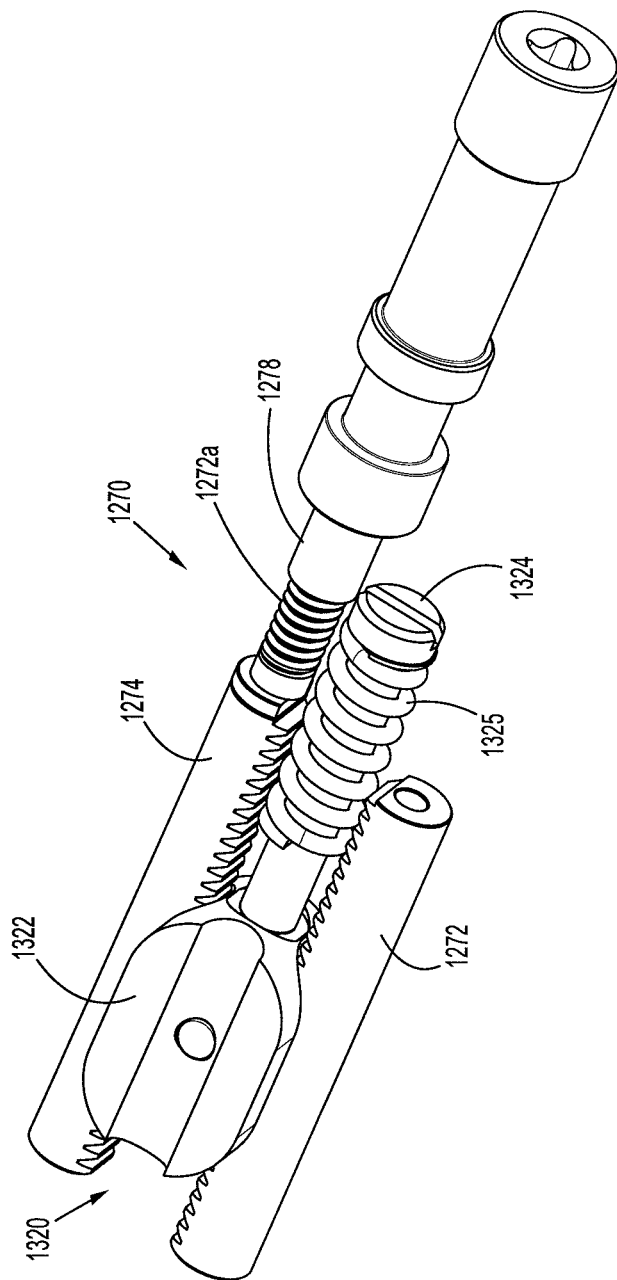
FIG. 56 is a perspective view of a cable tensioning assembly of the neck assembly of FIGS. 50 and 51.
Figure 59:
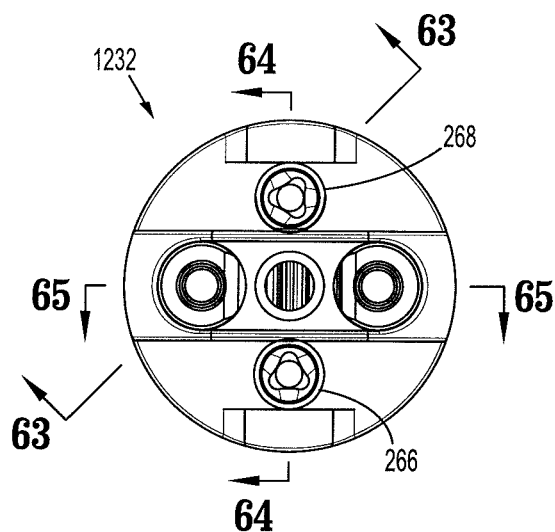
FIG. 59 is an end view of the proximal portion of the neck assembly of FIGS. 50 and 51, as seen from 59-59 of FIG. 53.
Figure 60:
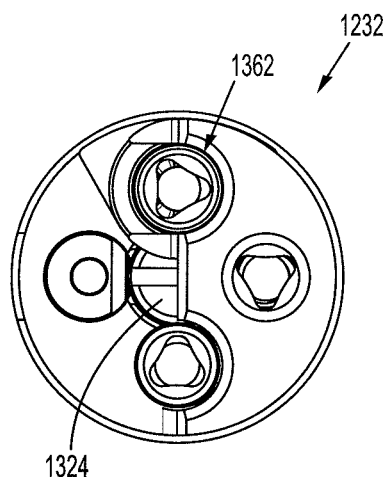
FIG. 60 is an end view of the proximal portion of the neck assembly of FIGS. 50 and 51, as seen from 60-60 of FIG. 53.
Figure 61:
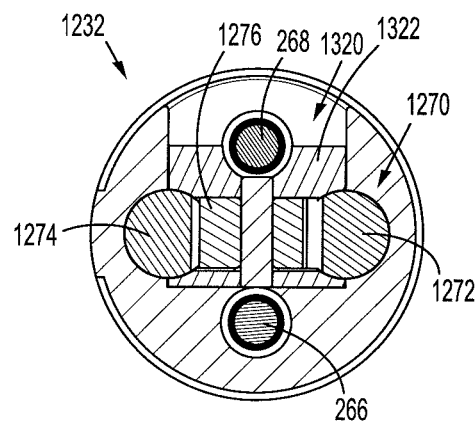
FIG. 61 is a cross-sectional view of the proximal portion of the neck assembly of FIGS. 50 and 51, as taken through 61-61 of FIG. 53.
Figure 62:
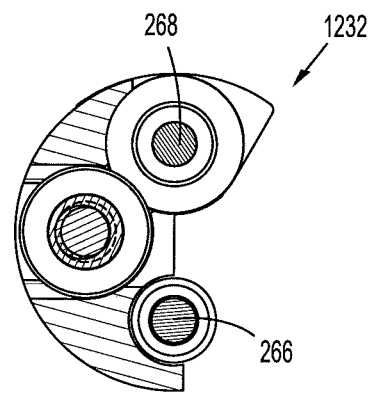
FIG. 62 is a cross-sectional view of the proximal portion of the neck assembly of FIGS. 50 and 51, as taken through 62-62 of FIG. 53.

As seen in FIG. 55, rack 1274 is attached to a threaded shaft 1272a extending proximally therefrom and threaded shaft 1272a is in threaded engagement with a distal end of an internally threaded nut 1278. Threaded nut 1278 is rotatably supported and axially fixed within a pocket 1232a (FIGS. 65 and 66) formed in proximal neck housing 1232. A proximal end of threaded nut 1278 is keyed to a distal end of third drive shaft 228 (see FIG. 5). While threaded shaft 1272a is shown extending from rack 1274, it is understood, and within the scope of the present disclosure, that the threaded shaft may extend from rack 1272 without departing from the principles of the present disclosure.

Articulation cables 262, 264 (see FIG. 12) include proximal ends that are secured to and extend from a respective distal end of racks 1272, 1274. Each articulation cable 262, 264 includes a distal end that extends through respective opposed lumens of links 234, and that are secured to or anchored in distal neck housing 234, as described above.

In operation, to articulate neck assembly 230 in a first direction, the third drive shaft 228 is rotated in a first direction, as described above, to rotate threaded nut 1278 and axially displace threaded shaft 1272a distally to axially displace rack 1274 distally. As rack 1274 is displaced axially in a distal direction, rack 1274 causes pinion gear 1276 to be rotated and to thus act on rack 1272, to axially displace rack 1272 in a proximal direction. As rack 1272 is axially displaced in a proximal direction, rack 1272 causes articulation cable 262 to be drawn in a proximal direction and thereby articulate neck assembly 230, in a manner similar to or identical to that which is shown in FIG. 16. Neck assembly 230 is articulated since axial displacement of rack 1274, in a distal direction, results in axial, distal displacement of articulation cable 264.

As seen in FIGS. 50-52, 55, 56, 61, and 63-66, neck assembly 230 of shaft assembly 200 includes a cable tensioning assembly 1320. Cable tensioning assembly 1320 includes a clevis 1322 slidably supported in proximal neck housing 1232, for axial displacement therewithin. Clevis 1322 rotatably supports pinion gear 1276 of articulation assembly 1270. Cable tensioning assembly 1320 includes an adjustment screw 1324, rotatably supported in proximal neck housing 1232 and retained against axial displacement. Adjustment screw 1324 is threadably connected to clevis 1322 such that rotation of adjustment screw 1324 results in axial displacement of clevis 1322.

Cable tensioning assembly 1320 also includes a biasing member 1325 interposed between a head of adjustment screw 1324 and a surface of proximal neck housing 1232 to ensure a continuous tensioning load is exerted on articulation cables 262, 264.

During an assembly of shaft assembly 200, an operator rotates adjustment screw 1324 in a direction so as to axially displace clevis 1322 in a direction, such as a proximal direction. As clevis 1322 is axially displaced in a proximal direction, clevis 1322 pulls on pinion gear 1276 of articulation assembly 1270. The pinion gear 1276 is engaged with each of rack 1274 and rack 1272. As pinion gear 1276 is axially displaced, in a proximal direction, pinion gear 1276 acts on racks 1272, 1274 to draw racks 1272, 1274 in a proximal direction. As racks 1272, 1274 are drawn in a proximal direction, with articulation cables 262, 264 respectively connected thereto, and with distal ends of articulation cables 262, 264 fixed or anchored in place, articulation cables 262, 264 are caused to be tensioned. It is contemplated that a set screw 328 (see FIG. 12) may be provided to fix the position of adjustment screw 1324 and help to maintain articulation cables 262, 264 tensioned.

It is contemplated that over time and/or following a number of uses, as articulation cables 262, 264 may become slack or stretched, biasing member 1325 functions to maintain an acceptable tension on articulation cables 262, 264, thus reducing a need for an end user of shaft assembly 200 to access adjustment screw 1324 and re-tension articulation cables 262, 264. Thus, the spring or biasing member continues to provide a load on the articulation cables.

As seen in FIGS. 50-55, 57, 58, and 63-64, neck assembly 230 of shaft assembly 200 includes a clutch mechanism 1360. Clutch mechanism 1360 is operatively connected to second drive cable 268 such that rotation of clutch mechanism 1360 results in rotation of second drive cable 268. The clutch prevents unwanted slippage of the drive cable.

Clutch mechanism 1360 includes a rotatable coupling member 1362 rotatably supported in a proximal hub 1232a of proximal neck housing 1232. See FIG. 64. Coupling member 1362 includes a first end 1362a configured to receive and mate with first output drive shaft 246a of transmission housing 212 of shaft assembly 200. Coupling member 1362 includes a second end 1362b having a pair of distally extending arms 1362c, each defining a pair of camming surfaces.

Clutch mechanism 1360 includes a plunger member 1364 rotatably and slidably supported in proximal hub 1232a of proximal neck housing 1232. Plunger member 1364 includes a first end 1364a having a pair of proximally extending arms 1364c, each defining a pair of camming surfaces. The camming surfaces of the plunger member 1364 complementing and being in cooperative engagement with the camming surfaces of coupling member 1362. Plunger member 1364 includes a second end 1364b secured to second drive cable 268.

Clutch mechanism 1360 includes a coupler 1366 axially fixed relative to proximal hub 1232a of proximal neck housing 1232. Coupler 1366 is configured to receive second end 1362b of coupling member 1362 and first end 1364a of plunger member 1364 and maintain second end 1362b of coupling member 1362 and first end 1364*a* of plunger member 1364 in operative association with one another. Coupler 1366 defines an angled inner-annular surface 1366*a* for mating with an angled outer annular profile of first end 1364*a* of plunger member 1364.

Clutch mechanism 1360 includes a biasing member 1368 interposed between a surface of proximal hub 1232*a* of proximal neck housing 1232 and plunger member 1364, tending to urge plunger member 1364 toward coupling member 1362 and tending to maintain second end 1362*b* of coupling member 1362 and first end 1364*a* of plunger member 1364 in operative association with one another. The biasing member presses the plunger member against the coupling member so that the camming surfaces of the plunger member in engagement with the camming surfaces of the coupling member.

In operation, clutch mechanism 1360 functions to transmit a rotation from surgical instrument 100 to end effector 400 to effectuate a rotation of end effector 400, as described above. The second drive cable or member 268 is rotated by the motor of the instrument housing 102. The clutch applies pressure between the coupling member and plunger to prevent slippage. The rotation of the second drive cable 268 is transmitted to the end effector, more specifically the rotation hub 294 of the end effector, to rotate the end effector.

Although FIG. 1 shows a handle assembly with an electromechanical driver, it is contemplated that the system can include a manually actuated handle assembly in any of the embodiments disclosed herein. Furthermore, the surgical instrument may comprise a stapler, electrosurgical instrument, grasper, or other type of surgical instrument. In any of the embodiments disclosed herein, the articulating shaft assembly may include a neck assembly or a pivot for articulation around a single pivot.

It will be understood that various modifications may be made to the embodiments disclosed herein. For example, surgical instrument 100 and/or cartridge assembly 410 need not apply staples but rather may apply two part fasteners as is known in the art. Further, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of preferred embodiments. Those skilled in the art will envision other modifications within the scope and spirit of the claims appended thereto.

What is claimed is:

1. A surgical instrument, comprising:
   a first jaw member including a proximal end, a distal end, and a channel extending from the proximal end to the distal end, the channel being configured to receive a staple cartridge assembly;
   a second jaw member including an anvil plate having a plurality of staple forming pockets, the first and second jaw members supported in relation to each other for movement between approximated and spaced positions; and
   a drive beam movable between the proximal end and the distal end of the first jaw member and having a substantially I-shaped cross-sectional profile, the drive beam having a first strut, a second strut, and a support beam extending between and connecting the first strut and the second strut along a first axis, wherein the first strut protrudes from the support beam along a second axis that is substantially perpendicular to the first axis, wherein the second strut protrudes from the support beam along a third axis that is substantially perpendicular to the first axis, and wherein the first strut is configured to engage with the first jaw member and the second strut is configured to engage with the second jaw member to progressively move the first and second jaw members from the spaced position to the approximated position as the drive beam moves from the proximal end of the first jaw toward the distal end of the first jaw;
   wherein the staple cartridge assembly includes a knife, a sled, and a plurality of staples, the knife having a knife blade, and the sled having a plurality of wedge members and configured to engage a plurality of staple pushers;
   the knife and the sled positioned at least partially distal to the drive beam so that distal movement of the drive beam moves the knife and the sled toward the distal end of the first jaw member, the sled configured to drive the plurality of staple pushers during distal movement and configured to be moved by the drive beam to a distal sled position or a distal-most sled position and remain at the distal sled position or the distal-most sled position when the drive beam moves proximally, the knife is configured to withdraw the knife blade from a position at or near the distal end of the first jaw member to a position at or near the proximal end of the first jaw member after ejection of staples;
   wherein the drive beam further includes a lock clip having a hook extending distally from the support beam.

2. The surgical instrument according to claim 1, wherein the drive beam includes a bore in at least one of the support beam, the first strut, or the second strut.

3. The surgical instrument according to claim 2, wherein a drive shaft extends through the bore of the drive beam.

4. The surgical instrument according to claim 1, wherein the knife is a component of a knife sled.

5. A surgical instrument, comprising:
   a first jaw member including a proximal end, a distal end, and a channel extending from the proximal end to the distal end, the channel being configured to receive a staple cartridge assembly;
   a second jaw member including an anvil plate having a plurality of staple forming pockets, the first and second jaw members supported in relation to each other for movement between approximated and spaced positions; and
   a drive beam movable between the proximal end and the distal end of the first jaw member and having a substantially I-shaped cross-sectional profile, the drive beam having a first strut, a second strut, and a support beam extending between and connecting the first strut and the second strut along a first axis, wherein the first strut protrudes from the support beam along a second axis that is substantially perpendicular to the first axis, wherein the second strut protrudes from the support beam along a third axis that is substantially perpendicular to the first axis, and wherein the first strut is configured to engage with the first jaw member and the second strut is configured to engage with the second jaw member to progressively move the first and second jaw members from the spaced position to the approximated position as the drive beam moves from the proximal end of the first jaw toward the distal end of the first jaw;
   wherein the staple cartridge assembly includes a knife, a sled, and a plurality of staples, the knife having a knife blade, and the sled having a plurality of wedge members and configured to engage a plurality of staple pushers;

the knife and the sled positioned at least partially distal to the drive beam so that distal movement of the drive beam moves the knife and the sled toward the distal end of the first jaw member, the sled configured to drive the plurality of staple pushers during distal movement and configured to be moved by the drive beam to a distal sled position or a distal-most sled position and remain at the distal sled position or the distal-most sled position when the drive beam moves proximally, wherein the knife is configured to limit or prevent movement of the knife following proximal movement of the drive beam;

wherein the knife further includes a lockout spring extending distally, the lockout spring being configured to prevent distal movement of the knife when the lockout spring is engaged in a lockout notch.

6. The surgical instrument according to claim 5, wherein each of the plurality of wedge members of the sled have angled leading edges, and wherein the angled leading edges are configured to contact the staple pushers during distal movement of the sled and to cause the staple pushers to drive staples from the staple cartridge assembly toward the anvil plate of the second jaw member.

7. The surgical instrument according to claim 6, wherein the staples are driven toward the staple forming pockets of the anvil plate.

8. The surgical instrument according to claim 5, wherein the staple cartridge assembly has a cartridge body.

9. The surgical instrument according to claim 5, wherein the staple cartridge assembly is removable after distal movement of the drive beam.

10. The surgical instrument of claim 5, wherein the distal sled position is at a substantially distal-most position of the channel.

11. The surgical instrument of claim 5, wherein the sled remains in the distal sled position following any proximal movement of the drive beam due to frictional engagement of the sled with the channel.

12. The surgical instrument of claim 5, wherein the sled is configured to disengage from at least one of the drive beam or the knife upon proximal movement of the drive beam so that the sled remains in the distal sled position.

13. A surgical instrument, comprising:
a first jaw member including a proximal end, a distal end, and a channel extending from the proximal end to the distal end, the channel being configured to receive a staple cartridge assembly;
a second jaw member including an anvil plate having a plurality of staple forming pockets, the first and second jaw members supported in relation to each other for movement between approximated and spaced positions; and
a drive beam movable between the proximal end and the distal end of the first jaw member and having a substantially I-shaped cross-sectional profile, the drive beam having a first strut, a second strut, a support beam extending between and connecting the first strut and the second strut along a first axis, wherein the first strut protrudes from the support beam along a second axis that is substantially perpendicular to the first axis, wherein the second strut protrudes from the support beam along a third axis that is substantially perpendicular to the first axis, and wherein the first strut is configured to engage with the first jaw member and the second strut is configured to engage with the second jaw member to progressively move the first and second jaw members from the spaced position to the approximated position as the drive beam moves from the proximal end of the first jaw toward the distal end of the first jaw;

wherein the staple cartridge assembly includes a knife, a sled, and a plurality of staples, wherein the knife includes a knife blade, and wherein the sled includes a plurality of wedge members and is configured to engage a plurality of staple pushers, wherein the knife and the sled are positioned so that distal movement of the drive beam moves the knife and the sled toward the distal end of the first jaw member, wherein the sled is configured to drive the plurality of staple pushers during distal movement, and wherein the sled is configured to be moved by the drive beam to distal sled position or a distal-most sled position and remain at the distal sled position or the distal-most sled position when the drive beam moves proximally, the knife configured to withdraw the knife blade from a position at or near the distal end of the first jaw member to a position at or near the proximal end of the first jaw member after ejection of staples;

wherein the drive beam further includes a lock clip having a hook extending distally from the support beam, and wherein the hook is configured to engage a window in the knife so that proximal movement of the drive beam moves the knife proximally.

14. A surgical instrument, comprising:
a first jaw member including a proximal end, a distal end, and a channel extending from the proximal end to the distal end, the channel being configured to receive a staple cartridge assembly;
a second jaw member including an anvil plate having a plurality of staple forming pockets, the first and second jaw members supported in relation to each other for movement between approximated and spaced positions; and
a drive beam movable between the proximal end and the distal end of the first jaw member and having a substantially I-shaped cross-sectional profile, the drive beam having a first strut, a second strut, a support beam extending between and connecting the first strut and the second strut along a first axis, wherein the first strut protrudes from the support beam along a second axis that is substantially perpendicular to the first axis, wherein the second strut protrudes from the support beam along a third axis that is substantially perpendicular to the first axis, and wherein the first strut is configured to engage with the first jaw member and the second strut is configured to engage with the second jaw member to progressively move the first and second jaw members from the spaced position to the approximated position as the drive beam moves from the proximal end of the first jaw toward the distal end of the first jaw;

wherein the staple cartridge assembly includes a knife, a sled, and a plurality of staples, wherein the knife includes a knife blade, and wherein the sled includes a plurality of wedge members and is configured to engage a plurality of staple pushers, wherein the knife and the sled are positioned so that distal movement of the drive beam moves the knife and the sled toward the distal end of the first jaw member, wherein the sled is configured to drive the plurality of staple pushers during distal movement, and wherein the sled is configured to be moved by the drive beam to distal sled position or a distal-most sled position and remain at the distal sled position or the distal-most sled position when the drive beam moves proximally, wherein the knife is configured to limit or prevent movement of the knife following proximal movement of the drive beam, and wherein the knife further includes a lockout spring extending distally, the lockout spring being configured to prevent distal movement of the knife when the lockout spring is engaged in a lockout notch.

15. A surgical tool, comprising:
   a shaft extending along a longitudinal axis between a proximal end and a distal end; and
   the surgical instrument according to claim 14 connected to the distal end of the shaft.

16. The surgical tool according to claim 15, wherein the surgical instrument is configured to move between a linear configuration that is substantially parallel to the longitudinal axis of the shaft and an angled configuration that is pitched relative to the longitudinal axis of the shaft.

17. The surgical tool according to claim 15, wherein the surgical instrument is configured to rotate about the longitudinal axis of the shaft.

* * * * *